United States Patent
Price et al.

(10) Patent No.: US 9,834,823 B2
(45) Date of Patent: Dec. 5, 2017

(54) **PRIMERS, ASSAYS AND METHODS FOR DETECTING AN *E. COLI* SUBTYPE**

(71) Applicants: THE TRANSLATIONAL GENOMICS RESEARCH INSTITUTE, Phoenix, AZ (US); UNIVERSITY OF WASHINGTON, Seattle, WA (US); REGENTS OF THE UNIVERSITY OF MINNESOTA, Minneapolis, MN (US)

(72) Inventors: Lance B. Price, Baltimore, MD (US); Evgeni V. Sokurenko, Seattle, WA (US); James R. Johnson, St. Paul, MN (US)

( * ) Notice: Subject to any disclaimer, the term of this patent is extended or adjusted under 35 U.S.C. 154(b) by 372 days.

(21) Appl. No.: 14/412,667

(22) PCT Filed: Jul. 2, 2013

(86) PCT No.: PCT/US2013/049164
§ 371 (c)(1),
(2) Date: Jan. 2, 2015

(87) PCT Pub. No.: WO2014/008312
PCT Pub. Date: Jan. 9, 2014

(65) Prior Publication Data
US 2015/0126435 A1    May 7, 2015

Related U.S. Application Data

(60) Provisional application No. 61/667,402, filed on Jul. 2, 2012.

(51) Int. Cl.
*C12P 19/34* (2006.01)
*C12Q 1/68* (2006.01)

(52) U.S. Cl.
CPC ........ *C12Q 1/689* (2013.01); *C12Q 2600/112* (2013.01); *C12Q 2600/156* (2013.01)

(58) Field of Classification Search
USPC ........................................ 435/6.11, 6.12, 91.2
See application file for complete search history.

(56) References Cited

U.S. PATENT DOCUMENTS

| | | | | |
|---|---|---|---|---|
| 5,945,290 A | * | 8/1999 | Cowsert | C12N 15/1137 435/325 |
| 2002/0150587 A1 | | 10/2002 | Langermann et al. | |
| 2006/0094034 A1 | | 5/2006 | Brousseau et al. | |
| 2010/0112563 A1 | | 5/2010 | Liu et al. | |

FOREIGN PATENT DOCUMENTS

WO    2010/124085 A2    10/2010

OTHER PUBLICATIONS

Rychlik et al., Nucleic Acids Research 17(21), 8543-8551 (1989).*
Johnson, et al., "Epidemic Clonal Groups of *Escherichia coli* as a Cause of Antimicrobial-Resistant Urinary Tract Infections in Canada, 2002 to 2004", Antimicrobial Agents and Chemotherapy, 53(7):2733-2739 (Jul. 2009).
Johnson et al., "Abrupt Emergence of a Single Dominant Multidrug-Resistant Strain of *Escherichia coli*", Journal of Infectious Diseases, 207(6):919-928 (Jan. 3, 2013).
Leflon-Guibout et al., "Emergence and Spread of Three Clonally Related Virulent Isolates of CTX-M-15-Producing *Escherichia coli* with Variable Resistance to Aminoglycosides and Tetracycline in a French Geriatric Hospital", Antimicrobial Agents and Chemotherapy, 48(10):3736-3742 (Oct. 2004).
Peirano et al., "Molecular epidemiology of *Escherichia coli* producing CTX-M B-lactamases: the worldwide emergence of clone ST131 025:H4", International Journal of Antimicrobial Agents, 35:316-321 (2010).
Database EMBL "*Escherichia coli* isolate 166 malate dehydrogenase (mdh) gene, partial cds.", XP055256456, retrieved from EBI accession No. EM_STD:AY832980 Database accession No. AY832980 (Dec. 14, 2004).
Database EMBL "*Escherichia coli* strain 87-14 sbmA protein (ECs0427) gene, complete cds.", XP055256462, retrieved from EBI accession No. EM-STD:EU905417 Database accession No. EU905417 (May 1, 2009).
Banerjee, R. et al., "Molecular Epidemiology of *Escherichia coli* Sequence Type 131 and Its H30 and H30-Rx Subclones Among Extended-Spectrum-Beta_Lactamase-Positive and -Negative *E. coli* Clinical Isolates from the Chicago Region, 2007 to 2010", Antimicrobial Agents and Chemotherapy, 57(12:6385-6388 (Sep. 30, 2013).
Johnson, Jr. et al., "*Escherichia coli* Sequence Type ST131 as the Major Cause of Serious Multidrug-Resistant *E. coli* Infections in the United States", Clinical Infectious Diseases, 51(3):286-294 (2010).
Johnson, Jr. et al., "Molecular Epidemiological Analysis of *Escherichia coli* Sequence Type ST131 (O23:H4) and bla CTX-M-15 Among Extended-Spectrum-Beta-Lactamase-Producing *E. coli* from the United States, 2000 to 2009", Antimicrobial Agents and Chemotherapy, 56(5):2364-370 (Feb. 2012).
Kumagai, Y. et al., "Quinolone-Resistant Mutants of *Escherichia coli* DNA Topoisomerase IV parC Gene", Antimicrobial Agents and Chemotherapy, 40(3):710-714 (Mar. 1996).
International Search Report for PCT/US2013/049164 dated Dec. 16, 2013.
Written Opinion of the International Searching Authority for PCT/US2013/049164 dated Dec. 16, 2013.
International Preliminary Report on Patentability for PCT/US2013/049164 dated Feb. 24, 2015.
Donner, H. et al., "Biochip containing probes complementary with open reading frames in *Escherichia coli* K12, useful for detecting gene expression and expression patterns", "GSN:ACD81318", GSN, XP055330387 (Nov. 27, 2002).
Woodard, S. H. et al., "EM_TSA:JI022697", EM-TSA, XP055330400 (Mar. 6, 2011).
Teterin, H. et al., "Proteins and Nucleic Acids from Meningitis/Sepsis-Assocaited *Escherichia coli*", EM_PAT: DM050637, EM_Pat, XP055330392 (Mar. 30, 2009).

* cited by examiner

*Primary Examiner* — Kenneth Horlick

(57) ABSTRACT

Disclosed are primers, probes, and single nucleotide polymorphisms (SNP) specific to a distinct subclones of the *E. coli* sequence type 131 (ST131). Also disclosed are methods and assay kits useful in detecting the presence of the distinct subtype of *E. coli* and methods of treating a subject suffering from an infection from a subclone of ST131.

17 Claims, 56 Drawing Sheets

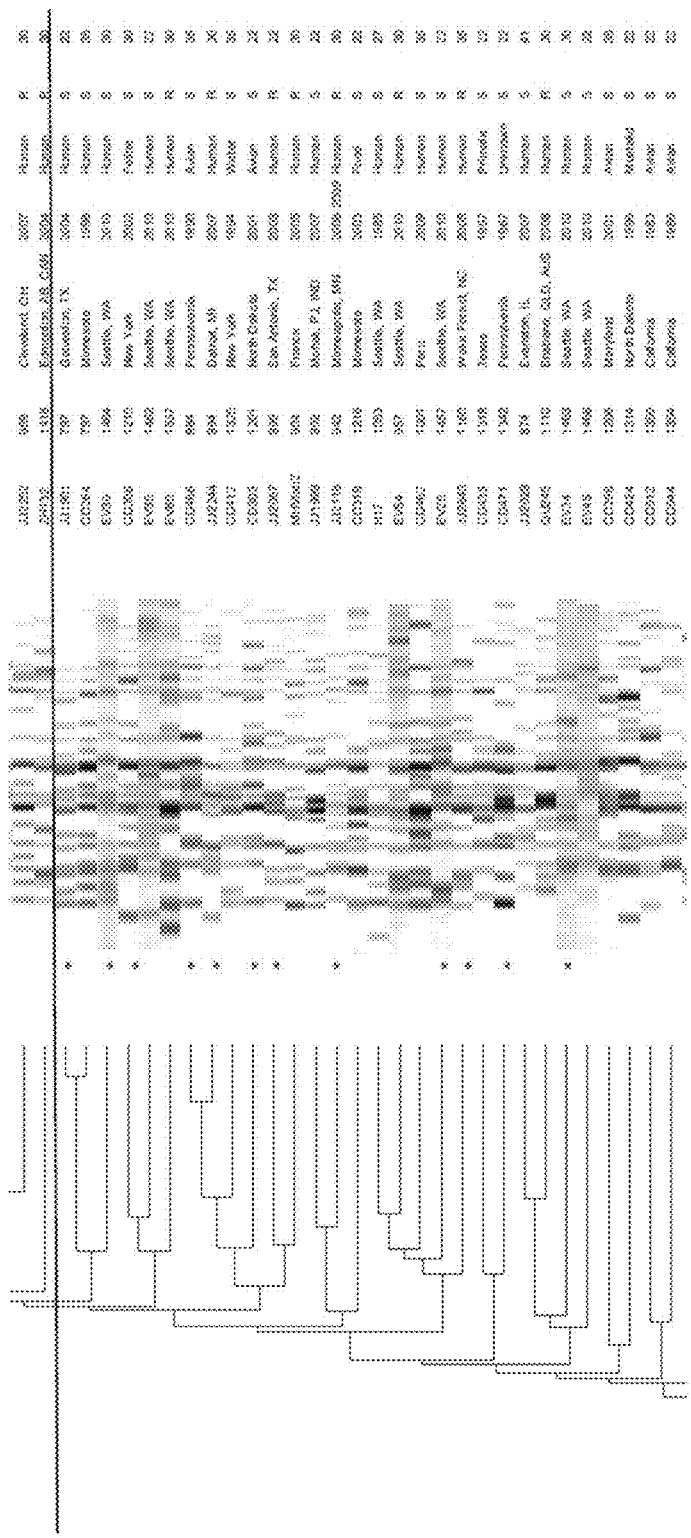
FIGURE 3 (cont.1)

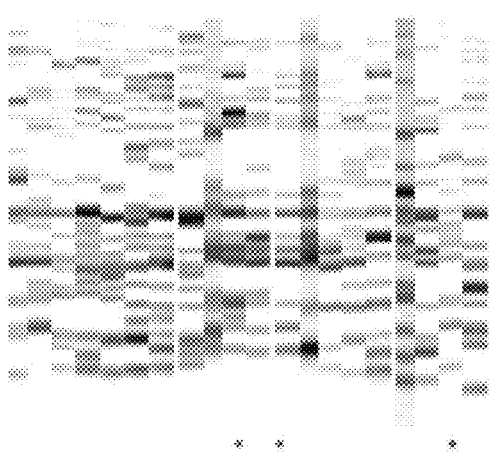
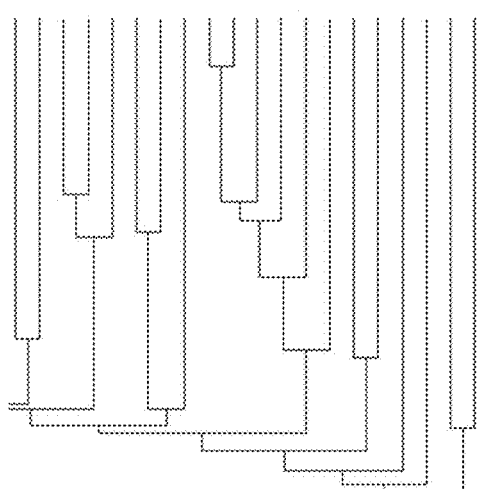
FIGURE 3 (cont.2)

FIGURE 5
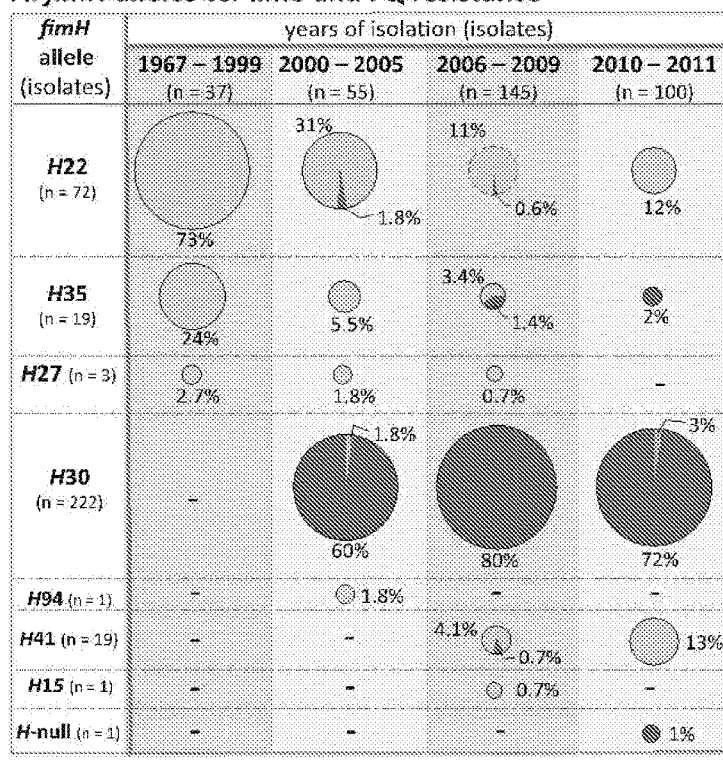
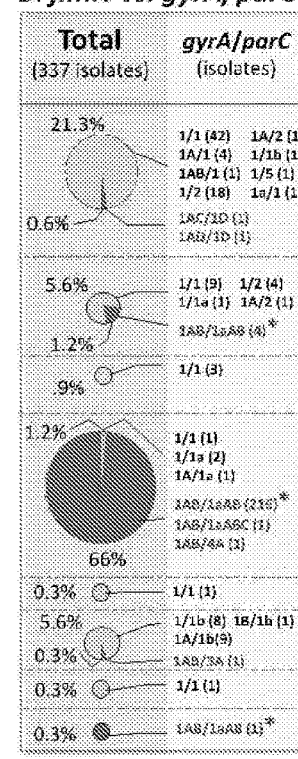

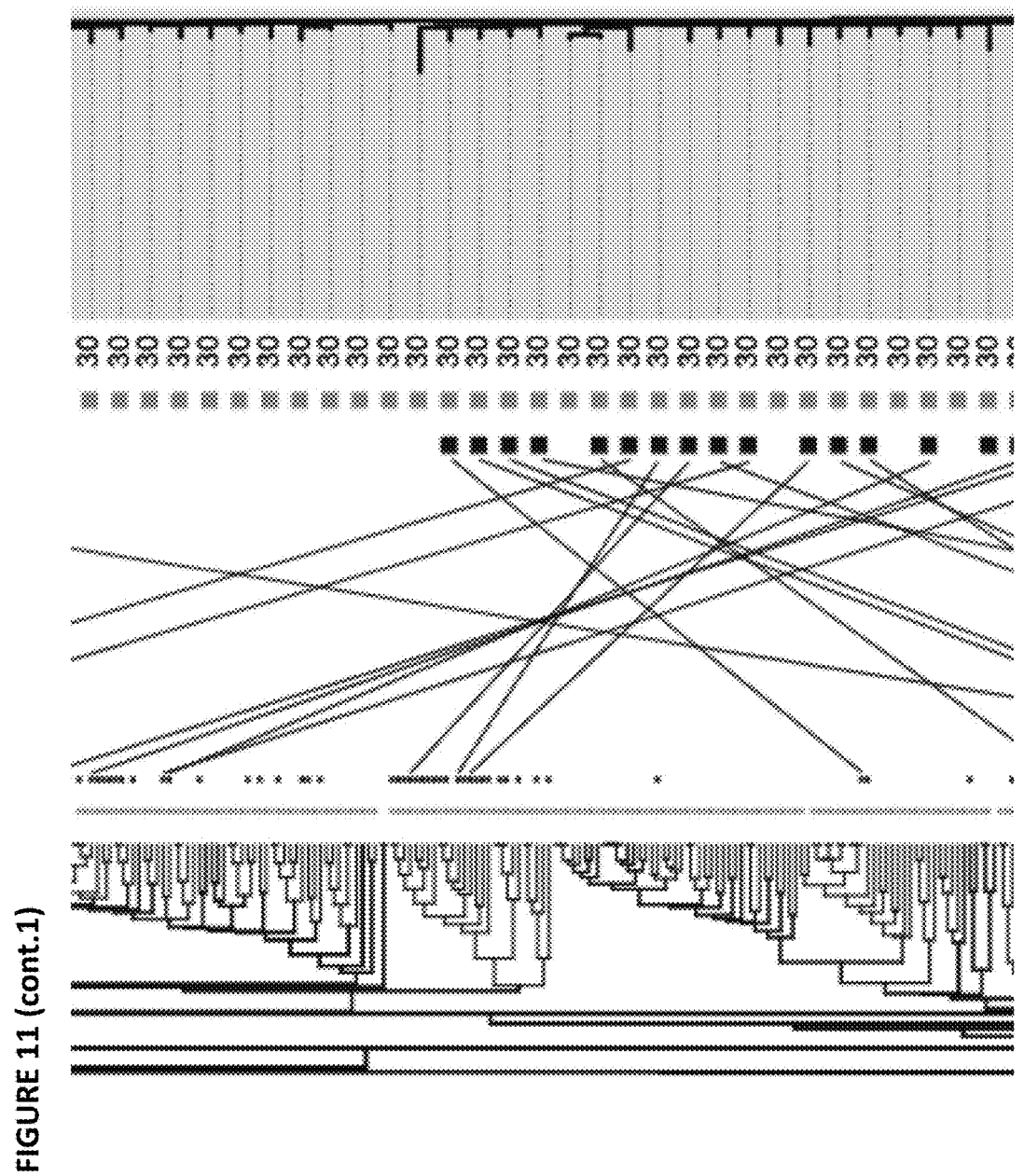
FIGURE 11 (cont.1)

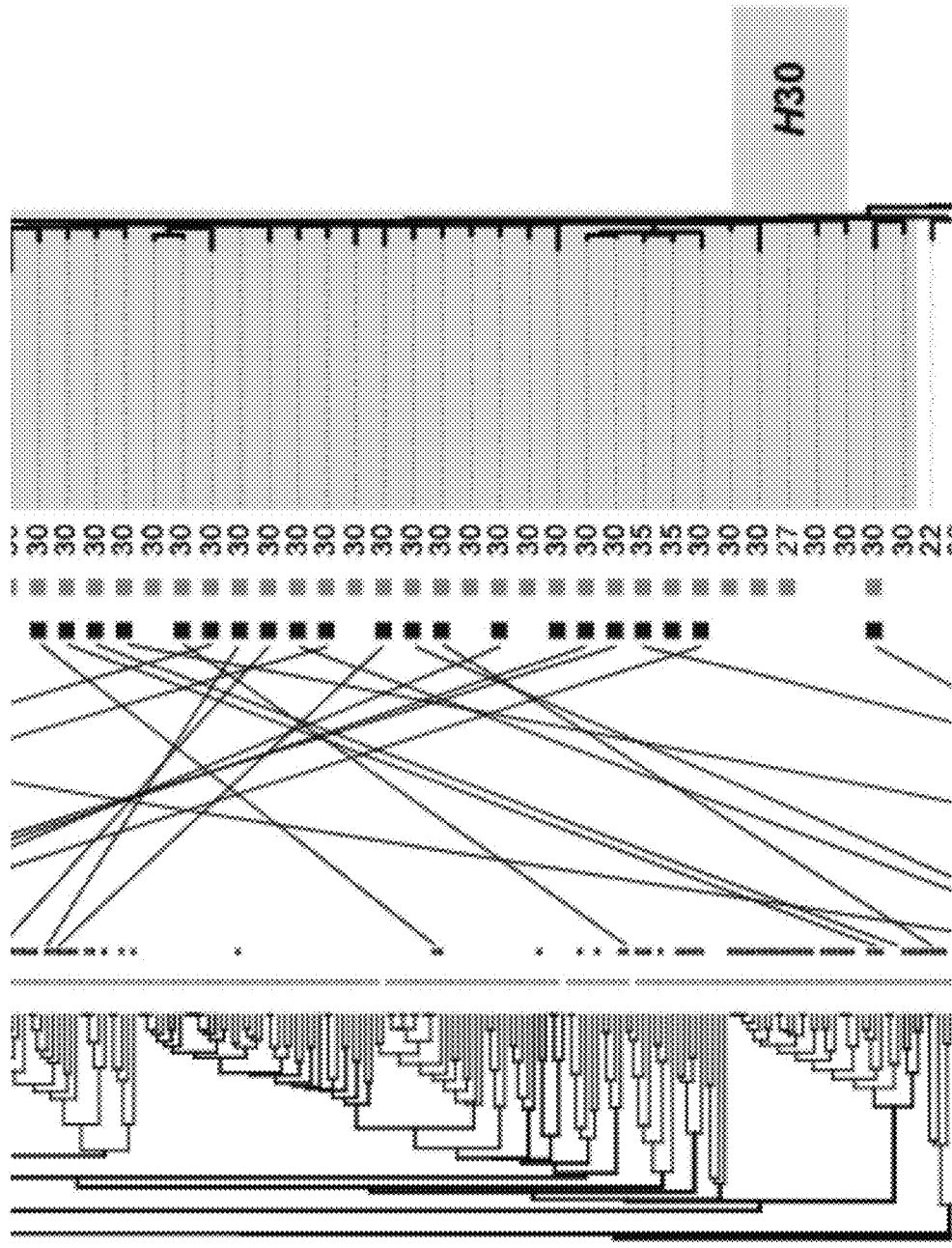
FIGURE 11 (cont.2)

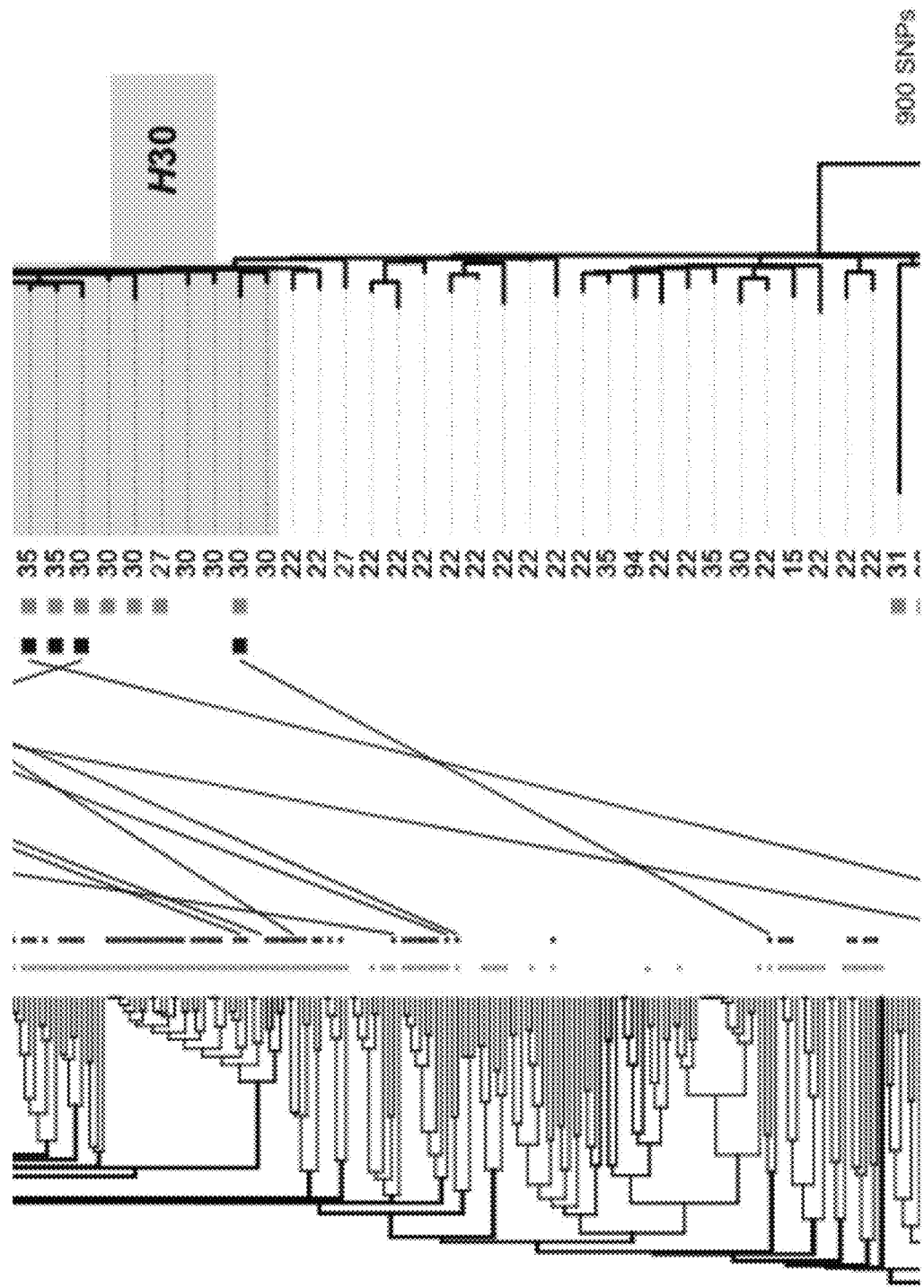
FIGURE 11 (cont.3)

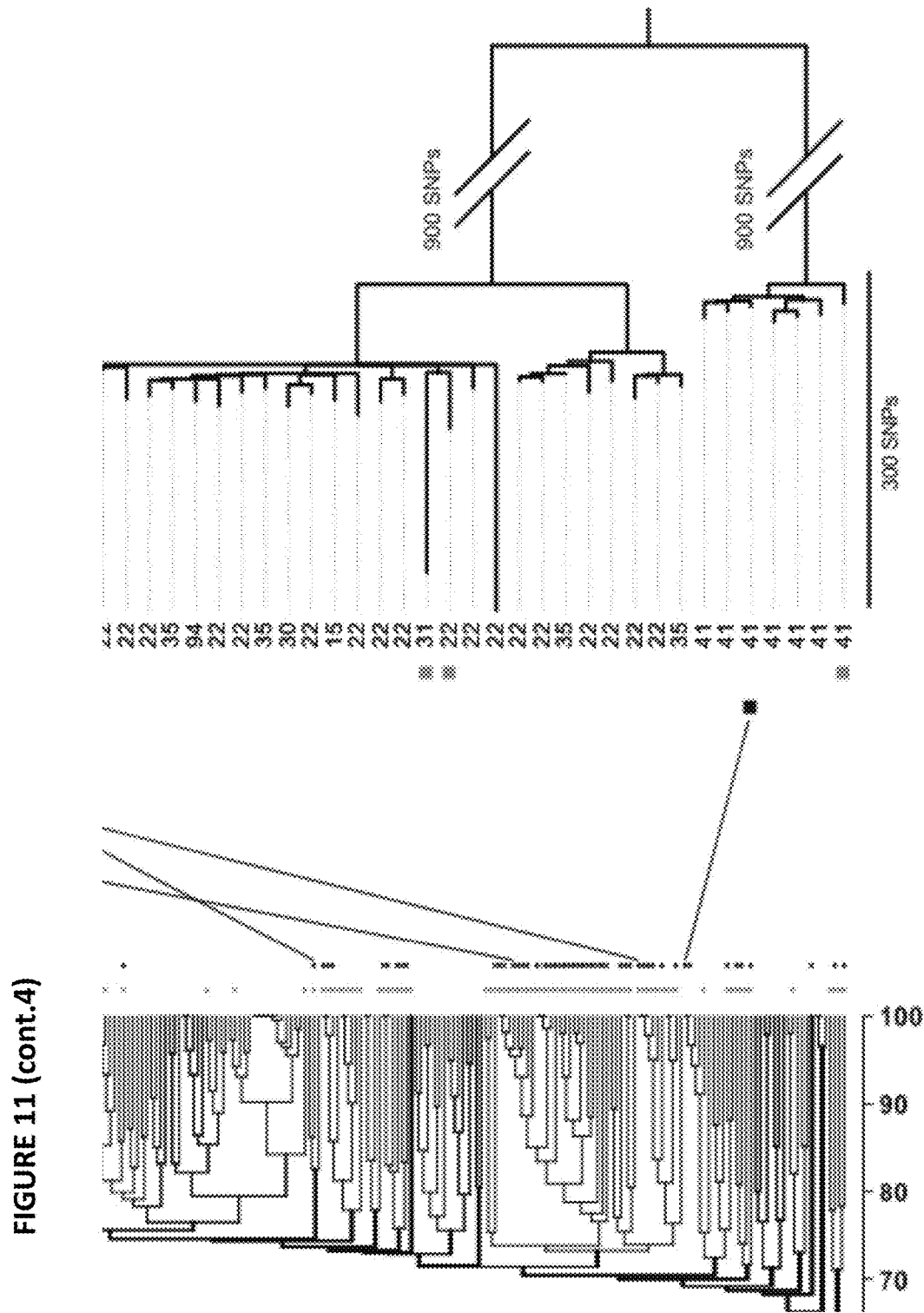
FIGURE 11 (cont.4)

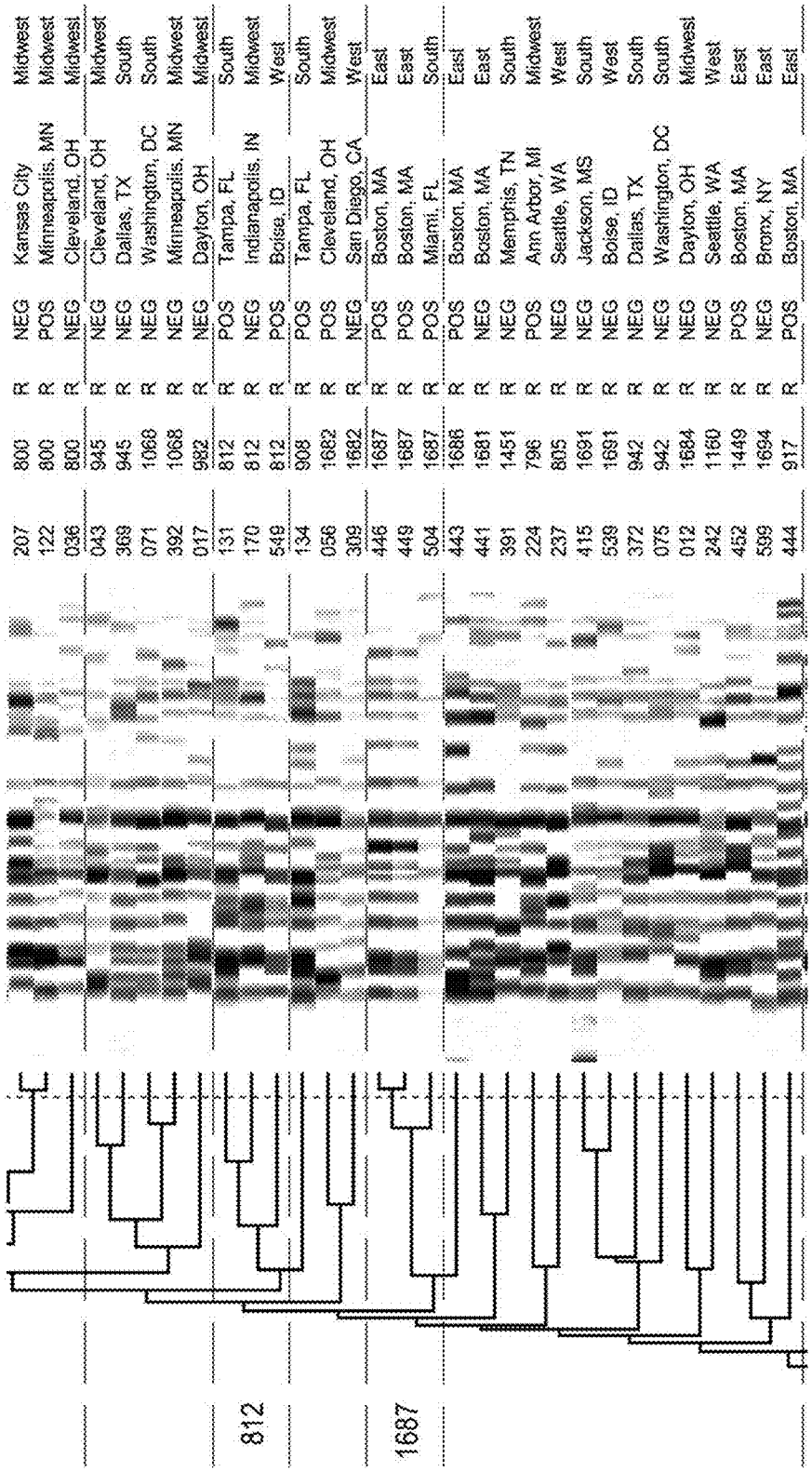
FIGURE 17 (cont.1)

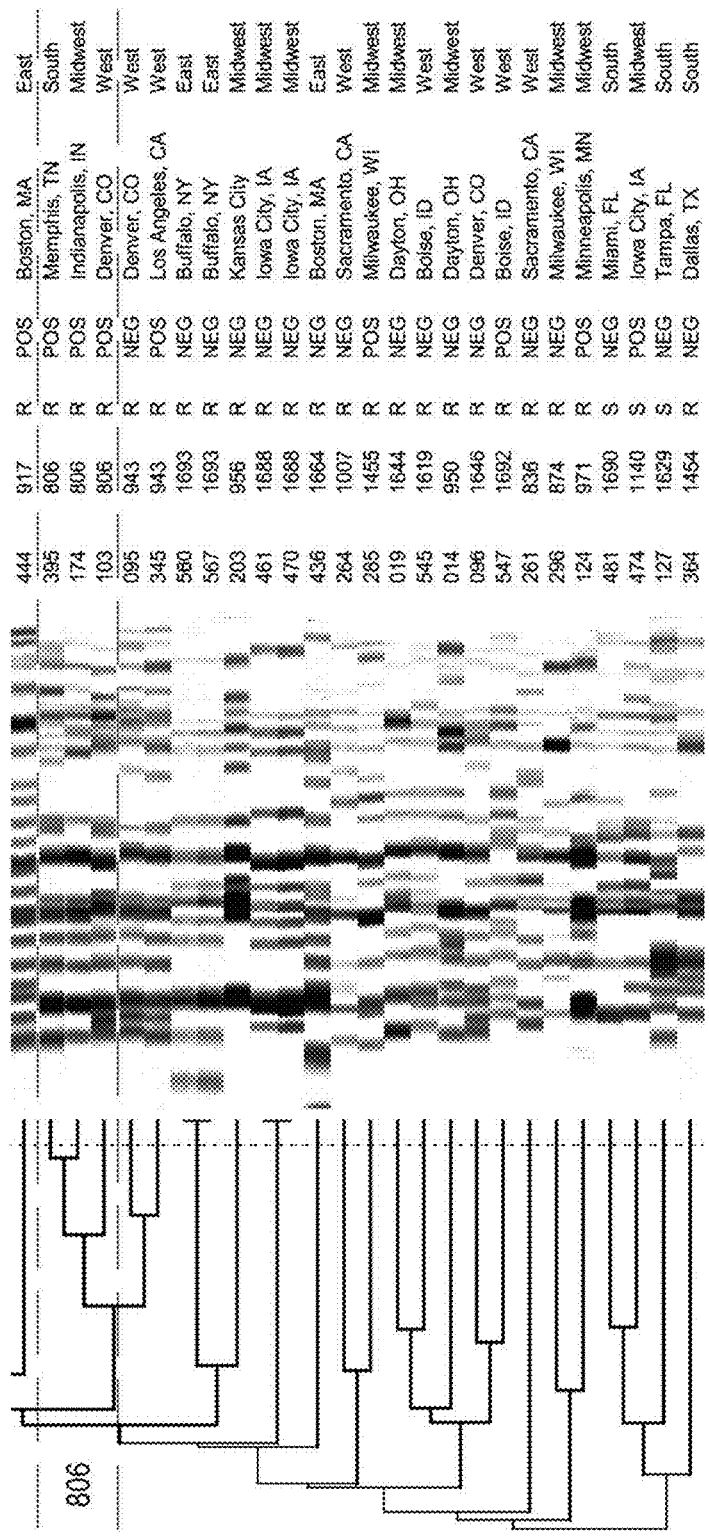
FIGURE 17 (cont.2)

FIGURE 18 (cont.1)
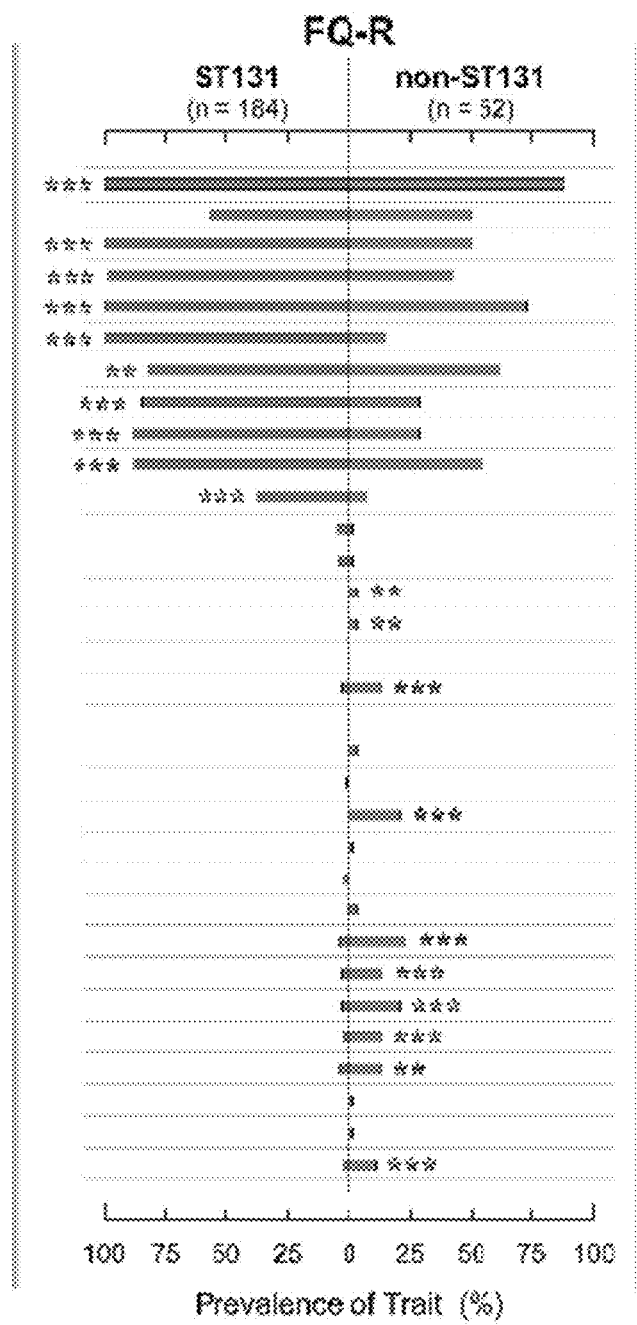

FIGURE 18 (cont.2)
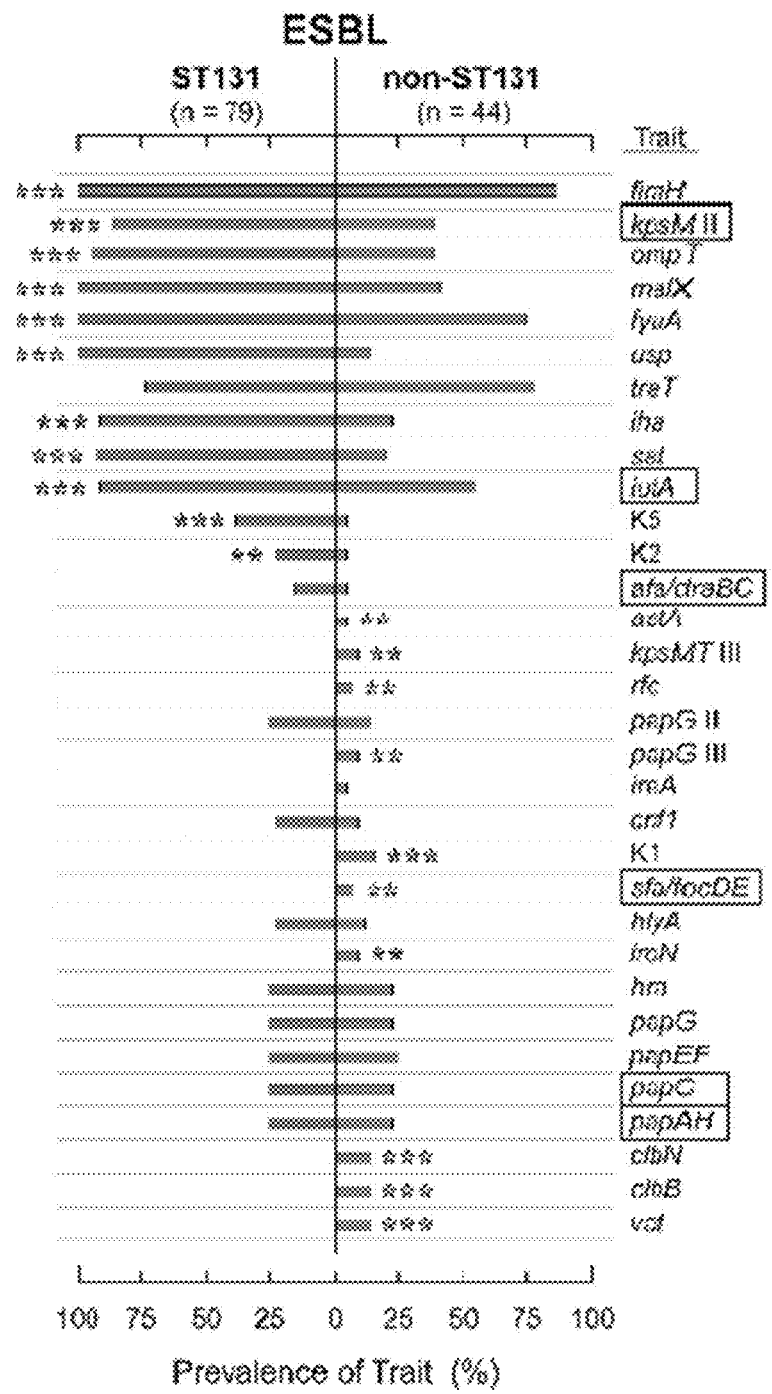

FIGURE 21
A
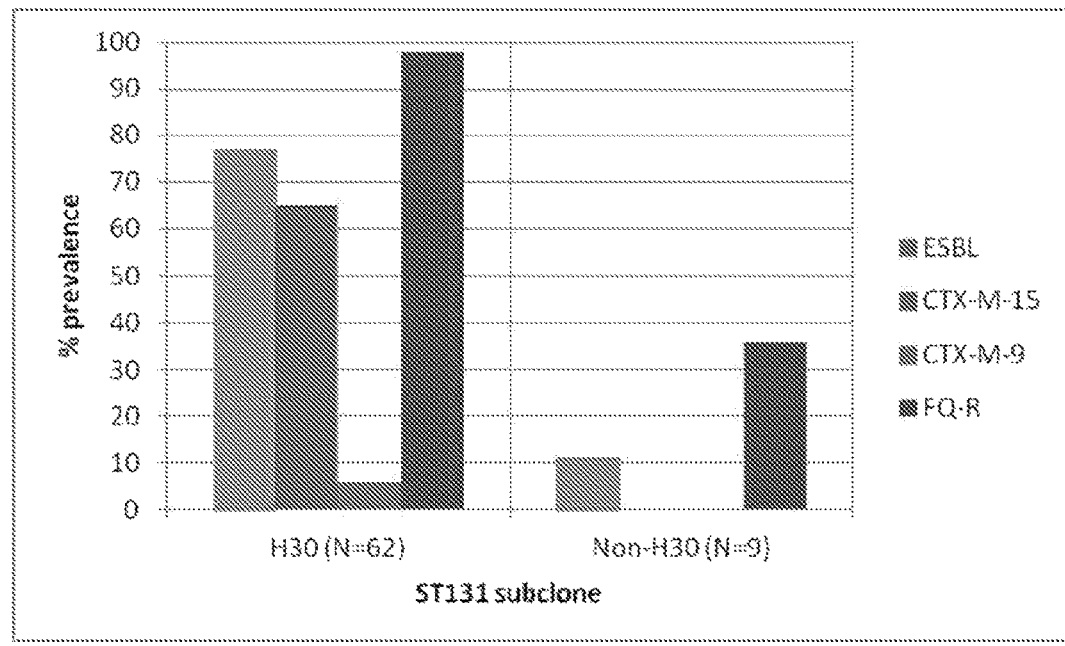
B
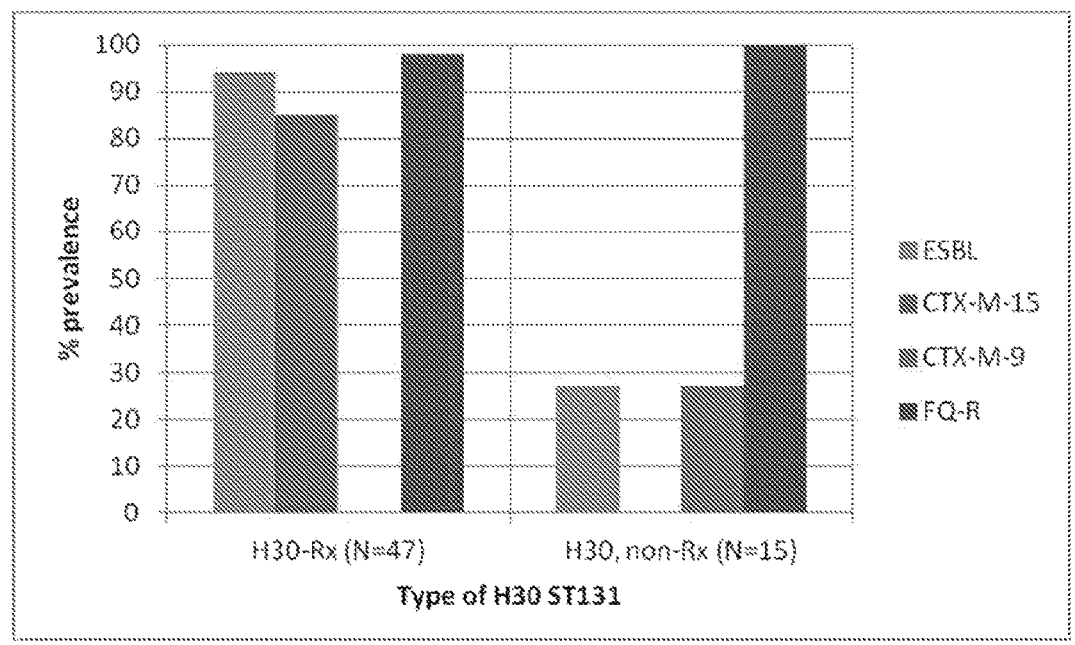

FIGURE 23

| gyrA allele | bp 248 | bp 259 | bp 260 | bp 516 |
|---|---|---|---|---|
| | Nucleotide at Indicated Position[a] (Associated Amino Acid Shift, if Any)[b] | | | |
| 1 | c | g | a | t |
| 1a | | | | c |
| 1A | t (S83L) | | | |
| 1AB | t (S83L) | a (D87N) | | |
| 1AC | t (S83L) | | g (D87G) | |
| 1B | | a (D87N) | | |
| 1AD | t (S83L) | t (D87Y) | | |

[a] Only polymorphic sites are shown. Bases are shown for ancestral allele (allele 1) and for other alleles, only if different from allele 1. Blank cells, identity with allele 1.

[b] Amino acid code: D, aspartate; G, glycine; L, leucine; N, asparagine; S, serine; Y, tyrosine.

FIGURE 24

Nucleotide at Indicated Position[a] (Associated Amino Acid Shift, if Any)[b]

| parC allele | bp 54 | bp 87 | bp 94 | bp 105 | bp 129 | bp 238 | bp 239 | bp 240 | bp 251 |
|---|---|---|---|---|---|---|---|---|---|
| 1 | c | t | c | t | c | a | g | t | a |
| 1a |  |  |  |  |  |  |  |  |  |
| 1b |  |  |  |  |  |  |  |  |  |
| 1aAB |  |  | t (P32S) |  |  |  | t (S80I) |  | t (E84V) |
| 1aABC |  |  | t (P32S) |  |  |  | t (S80I) |  | t (E84V) |
| 1D |  |  |  |  |  | c (S80R) |  |  |  |
| 2 |  |  |  |  | g |  |  |  |  |
| 3A |  |  |  |  |  |  | t (S80I) |  |  |
| 4A | t | c |  |  |  |  | t (S80I) | c |  |
| 5 | t | c |  | c |  |  |  |  |  |

[a] Only polymorphic sites are shown. Bases are shown for ancestral allele (allele 1) and, for other alleles, only if different from allele 1. Blank cells, identity with allele 1.
[b] Amino acid codes: E, glutamate; I, isoleucine; P, proline; R, arginine; S, serine; V, valine.

FIGURE 24 (cont.)

Nucleotide at Indicated Position[a] (Associated Amino Acid Shift, if Any)[b]

| parC allele | bp 251 | bp 261 | bp 321 | bp 348 | bp 372 | bp 387 | bp 391 | bp 399 | bp 408 | bp 411 | bp 432 | bp 471 |
|---|---|---|---|---|---|---|---|---|---|---|---|---|
| 1 | a | c | c | g | g | c | c | g | g | g | g | g |
| 1a | | | g | | | | | | | | | |
| 1b | | | t | | | | | | | | | |
| 1aAB | t (E84V) | | g | | | | | | | | | |
| 1aABC | t (E84V) | | g | | | | | | | | | |
| 1D | | | | | | | | | | | | |
| 2 | | | t | | | | t | | | | | |
| 3A | | | t | | | t | t | a | t | a | c | a |
| 4A | | | | | | | | | | | a | a |
| 5 | | t | | a | | | | | | | | |

[a] Only polymorphic sites are shown. Bases are shown for ancestral allele (allele 1) and, for other alleles, only if different from allele 1. Blank cells, identity with allele 1.
[b] Amino acid codes: E, glutamate; I, isoleucine; P, proline; R, arginine; S, serine; V, valine.

FIGURE 25 (cont.1)
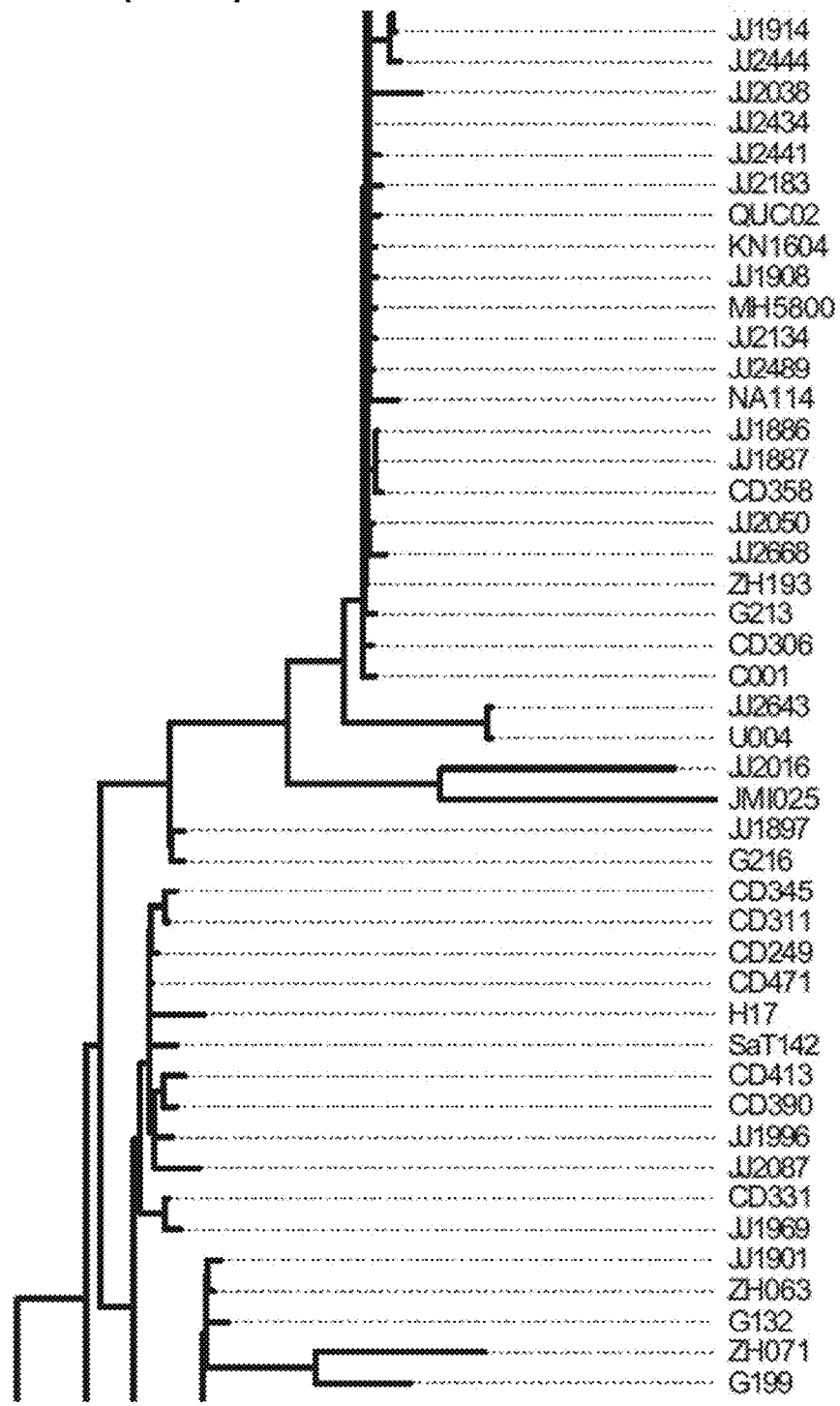

FIGURE 25 (cont.2)
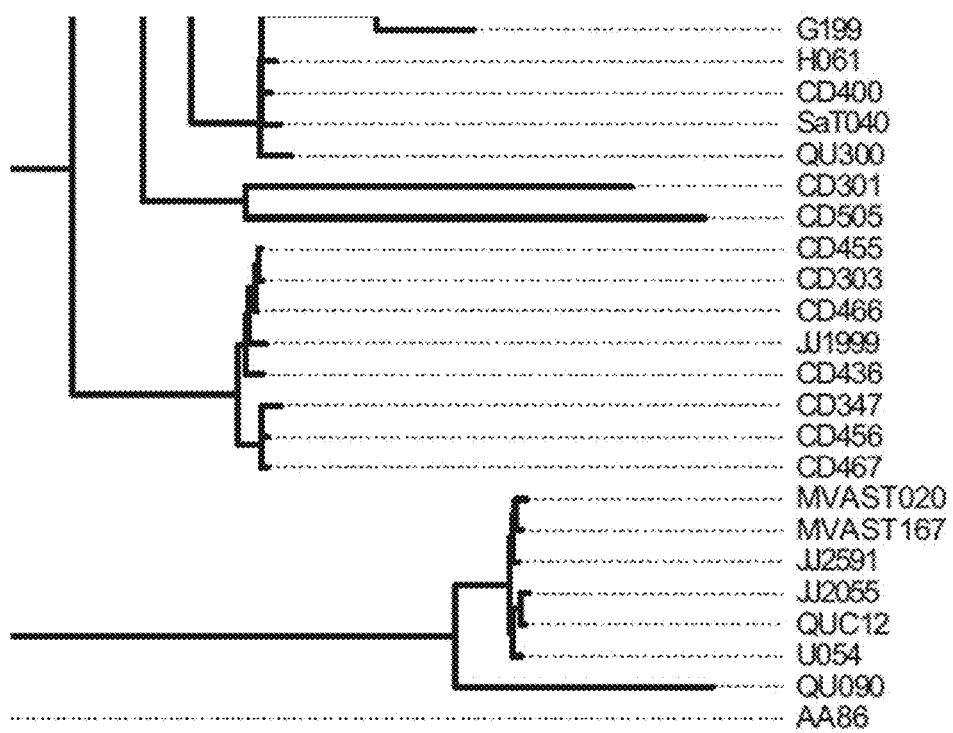

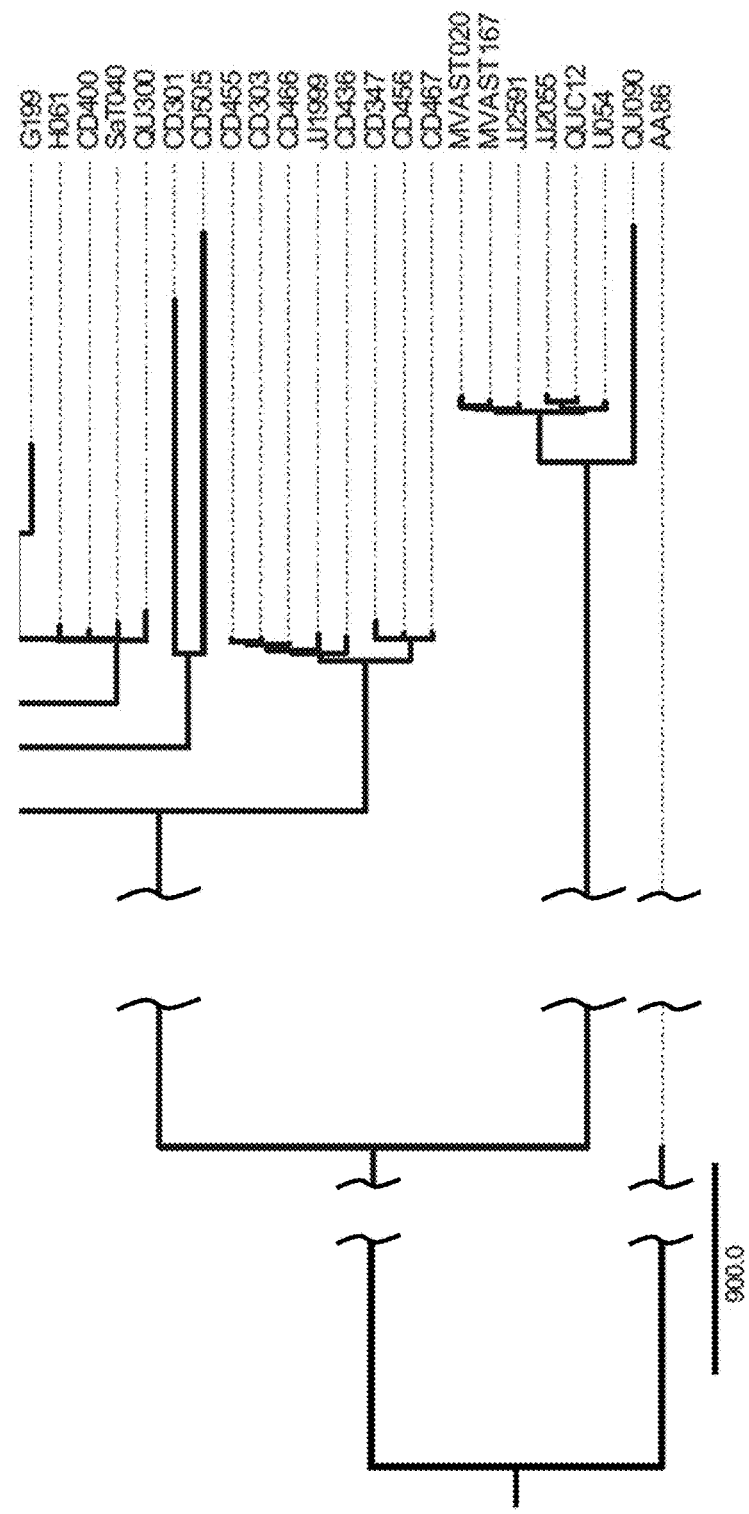
FIGURE 25 (cont.3)

FIGURE 26 (cont.1)
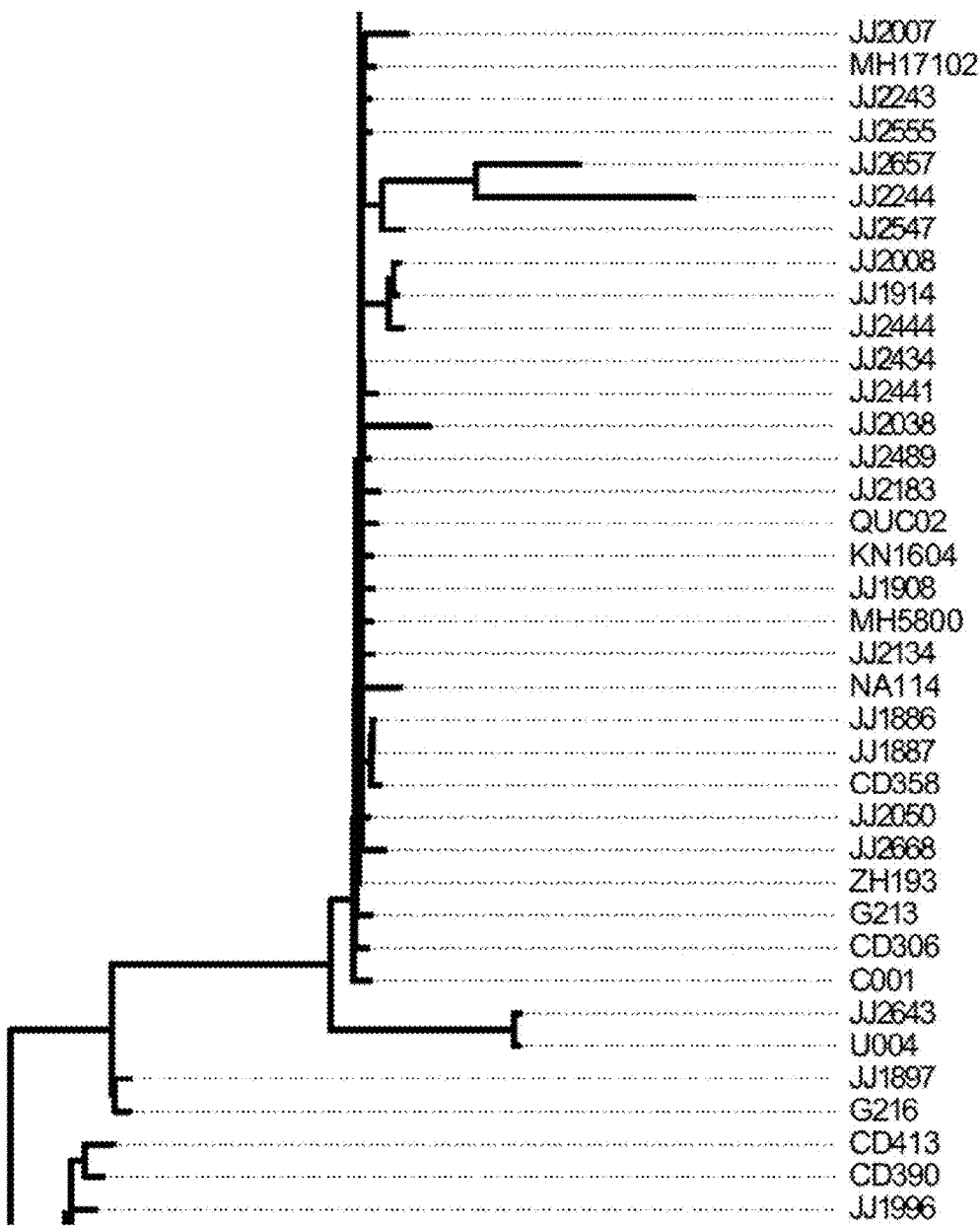

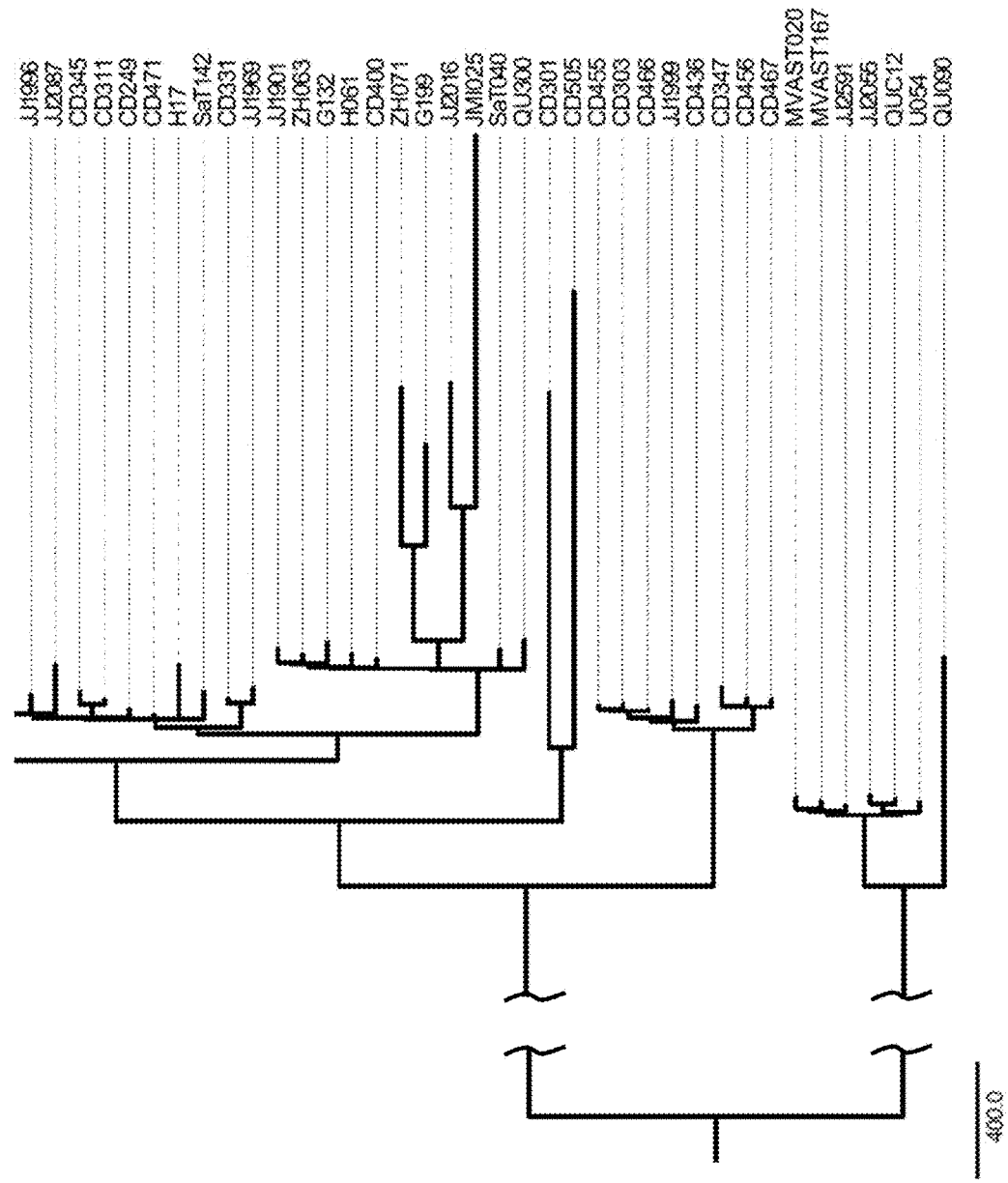
FIGURE 26 (cont.2)

FIGURE 27

Isolate
- JJ2193
- JJ2608
- JJ2118
- H016
- JJ2550
- JJ2041
- SaT158
- SaT049
- H006
- H003
- ZH164
- MVAST179
- MVAST084
- MVAST131
- MVAST0036
- CD449
- CU799
- JJ2578
- JJ2508
- JJ2210
- MVAST014
- MVAST158
- MVAST038
- JMI268
- MVAST077
- MVAST046
- CU758
- JJ2009
- JJ2528

FIGURE 27 (cont.1)

- JJ2528
- U024
- G150
- CD340
- JJ2007
- MH17102
- JJ2243
- JJ2547
- JJ2555
- JJ2008
- JJ1914
- JJ2444
- JJ2434
- JJ2441
- JJ2038
- JJ2489
- JJ2183
- QUC02
- KN1604
- JJ2657
- JJ1908
- MH5800
- JJ2134
- NA114
- JJ1886
- JJ1887
- JJ2643
- U004
- CD358
- JJ2050
- JJ2668
- ZH193

FIGURE 27 (cont.2)

- ZH193
- CD306
- G213
- JJ244
- C001
- JJ1897
- G216
- H17
- CD331
- JJ1969
- CD249
- CD345
- CD311
- CD301
- CD471
- SaT142
- JJ1901
- ZH063
- ZH071
- G132
- H061
- CD400
- G199
- SaT040
- JJ2016
- QU300
- CD413
- CD390
- JMI025
- JJ2087
- JJ1996
- CD505

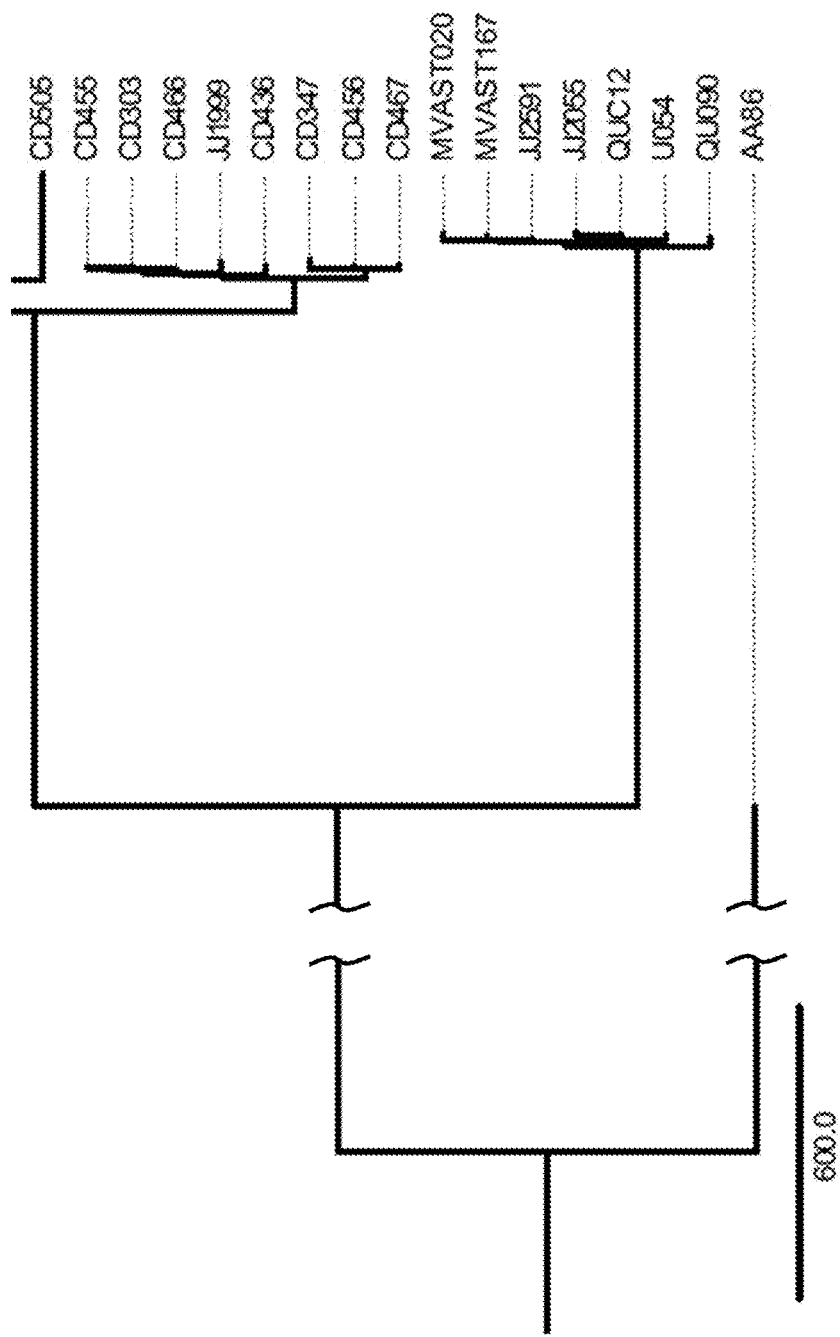
FIGURE 27 (cont.3)

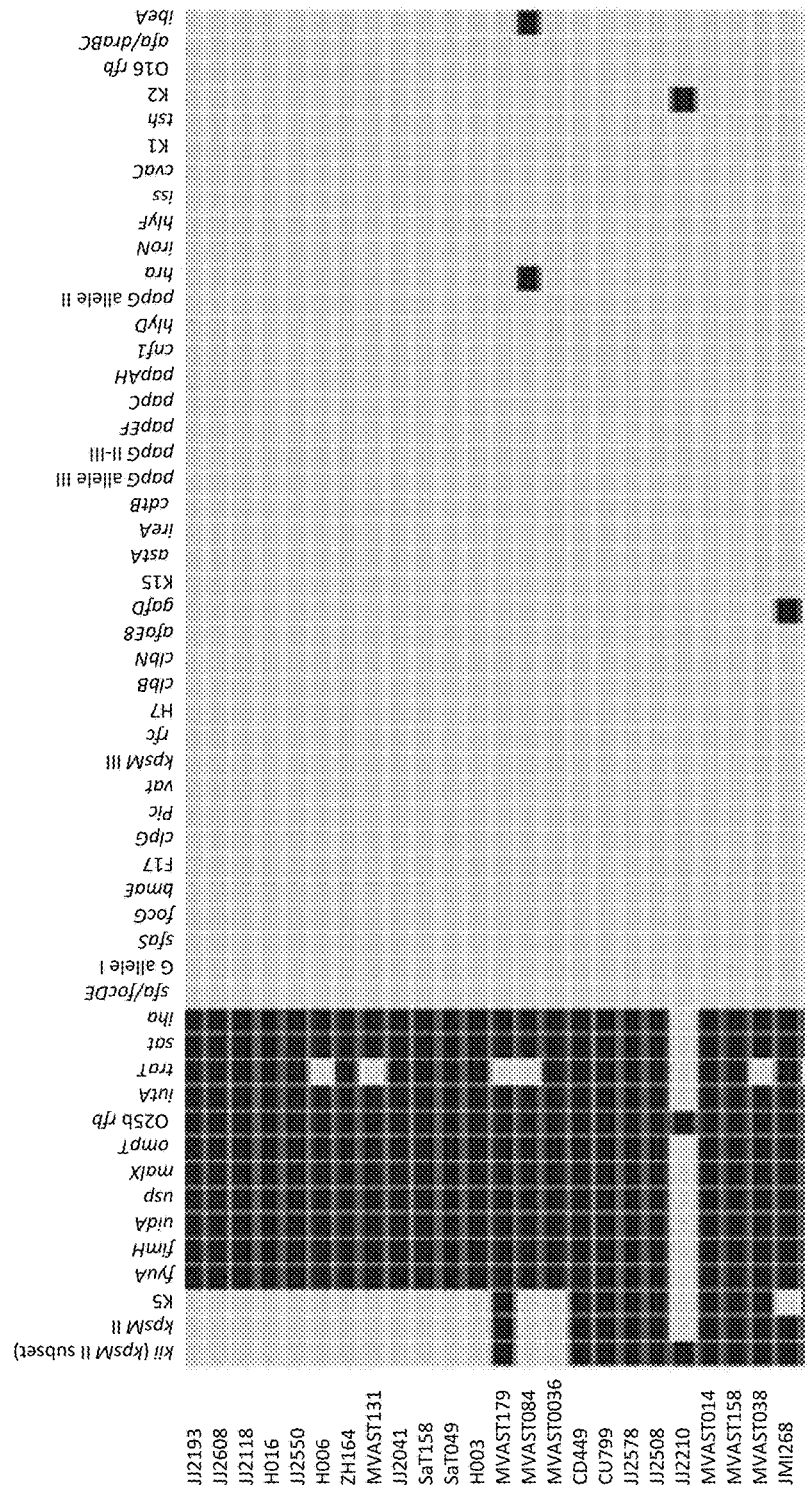
FIGURE 29 (cont.1)

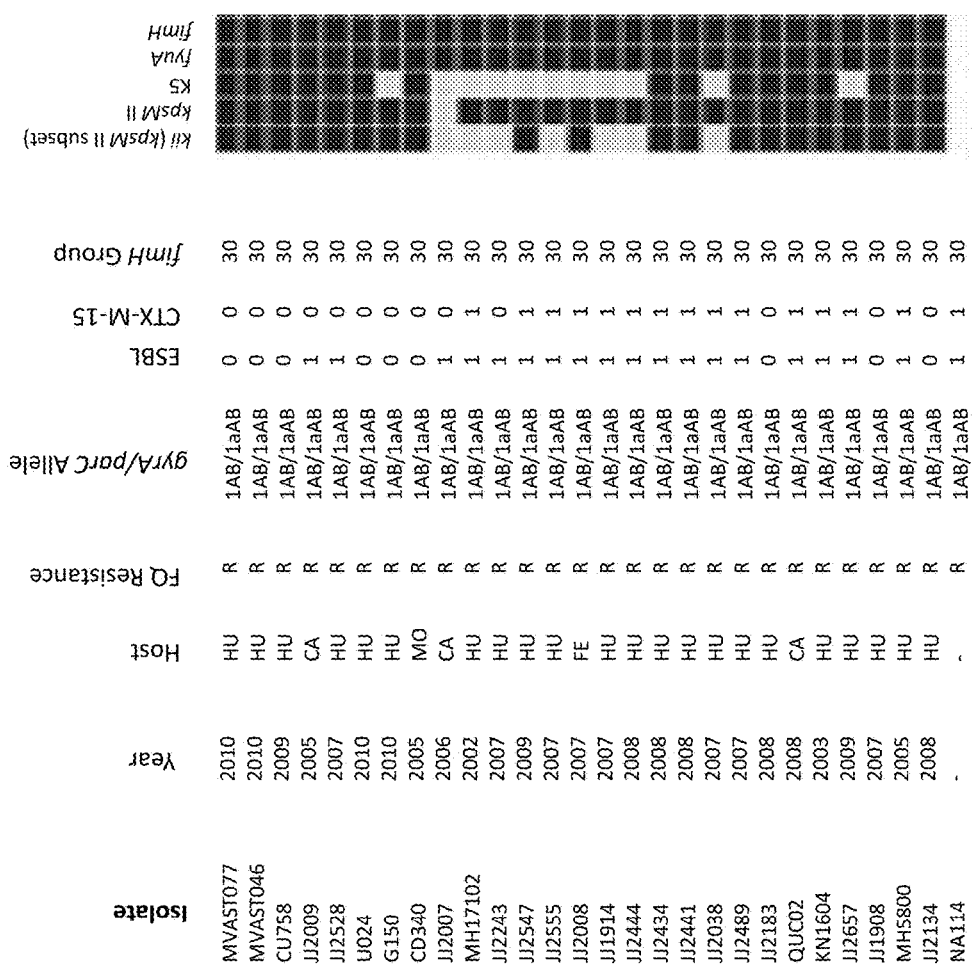
FIGURE 29 (cont.2)

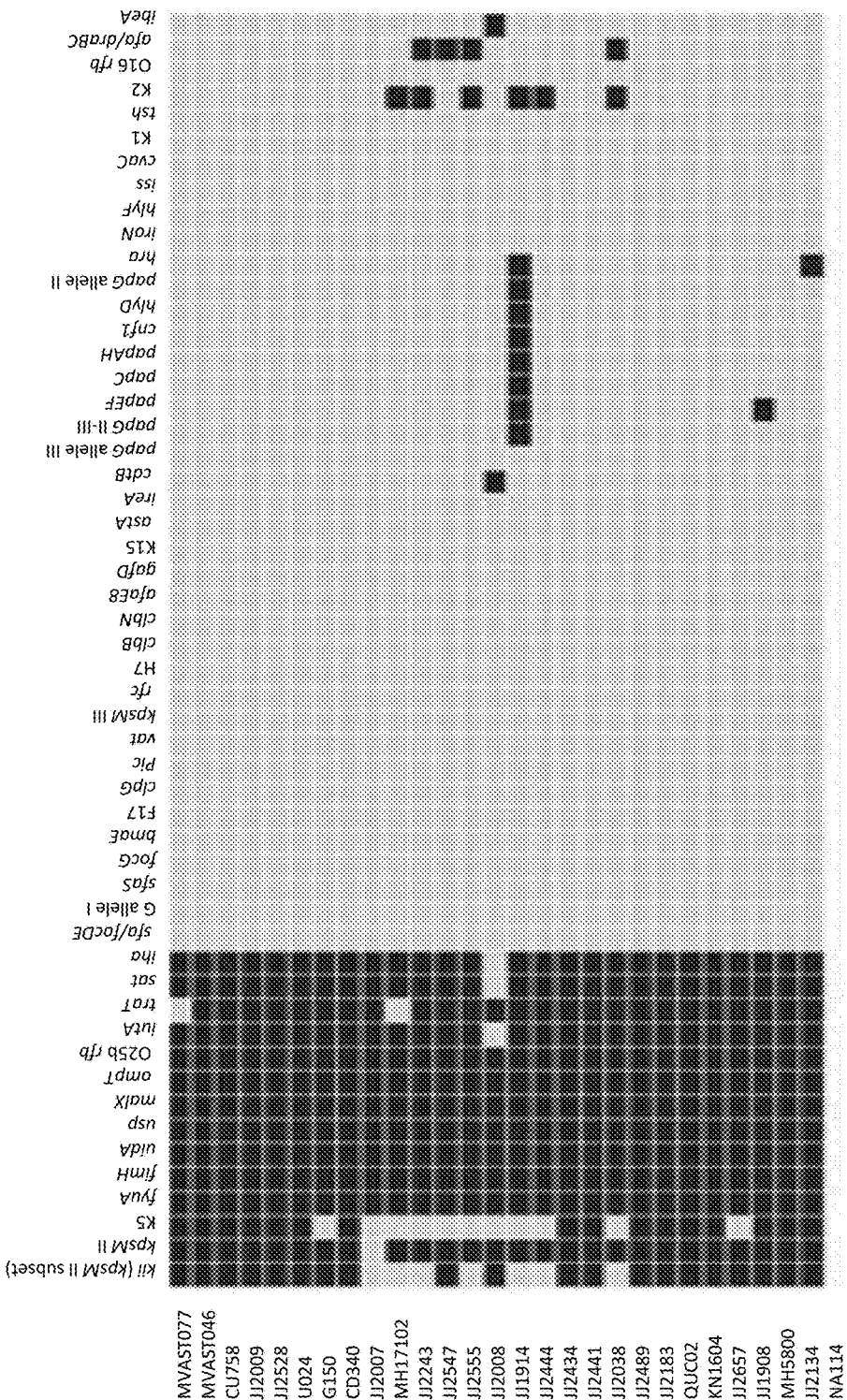
FIGURE 29 (cont.3)

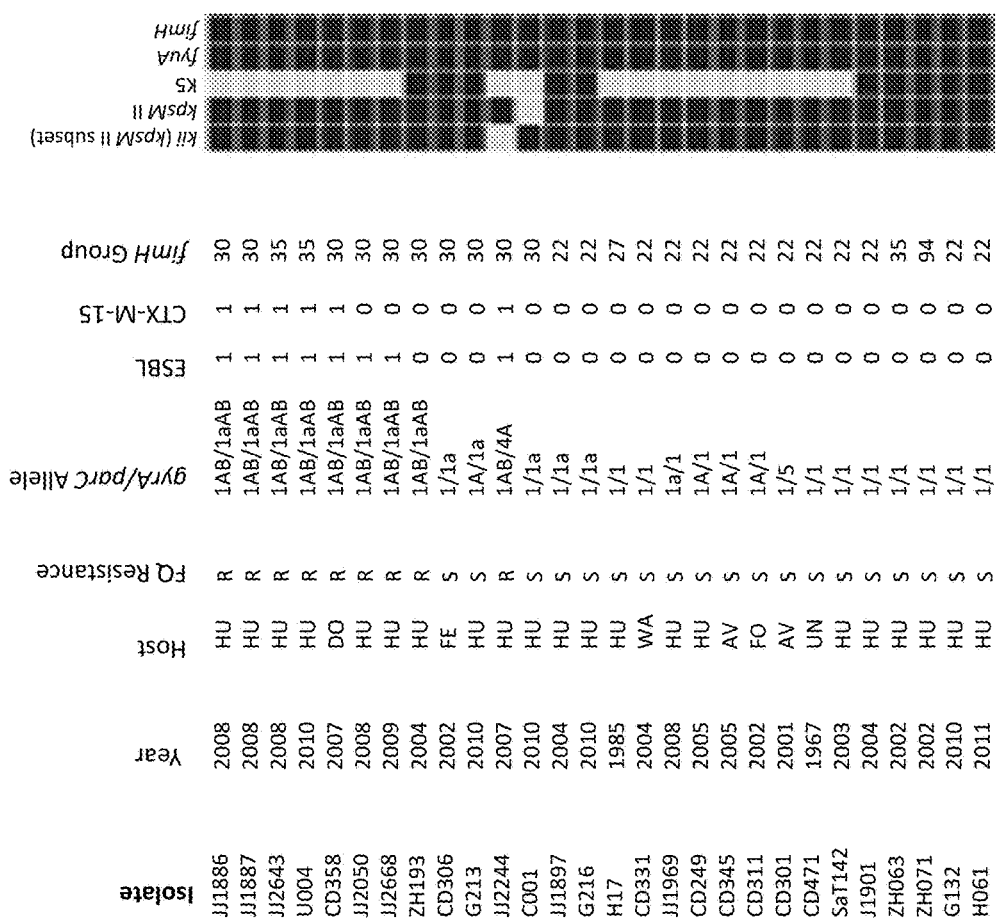
FIGURE 29 (cont.4)

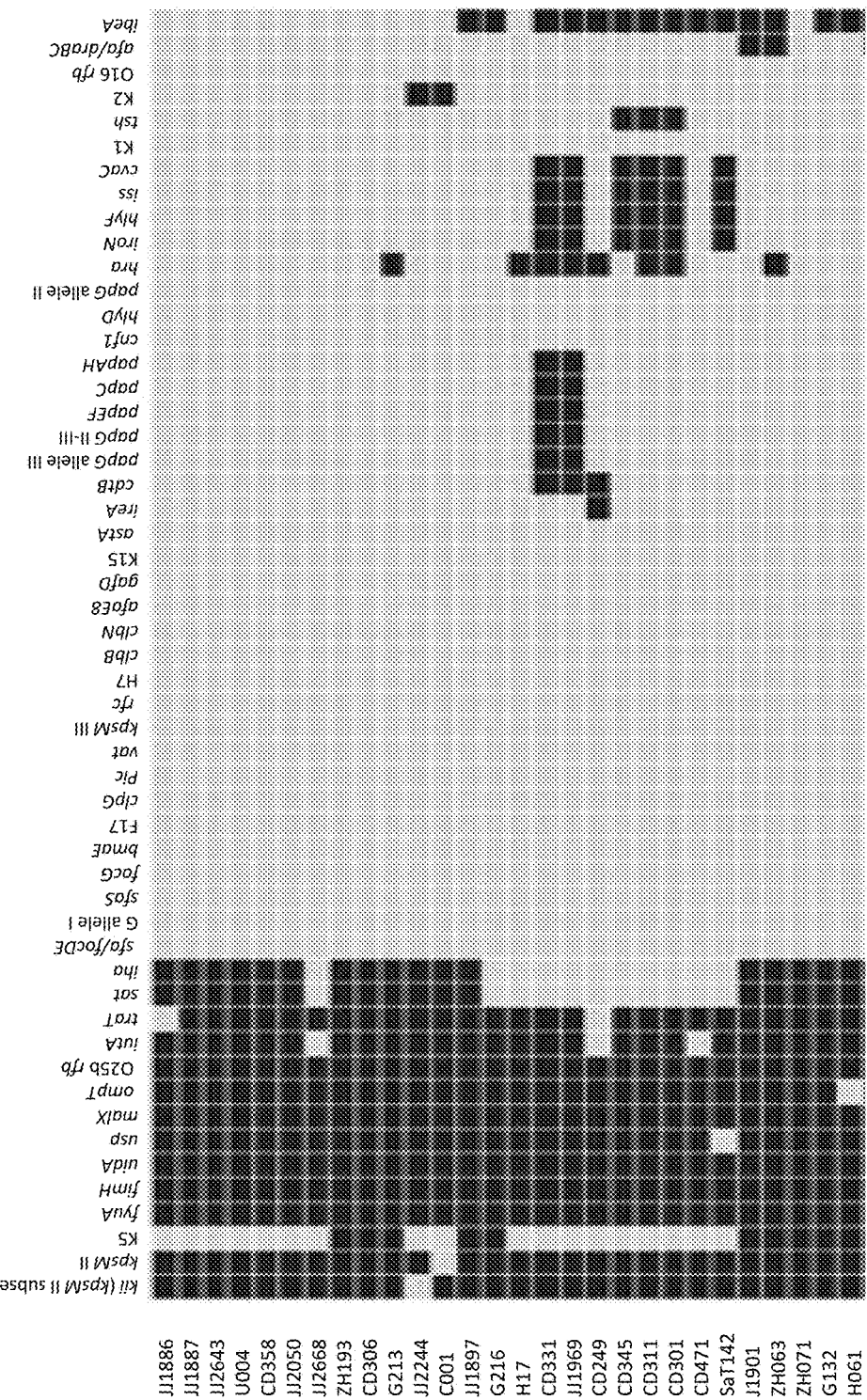
FIGURE 29 (cont.5)

FIGURE 29 (cont.6)

| Isolate | Year | Host | FQ Resistance | gyrA/parC Allele | ESBL | CTX-M-15 | fimH Group |
|---|---|---|---|---|---|---|---|
| CD400 | 1992 | HU | S | 1/1 | 0 | 0 | 35 |
| G199 | 2010 | HU | S | 1/1 | 0 | 0 | 30 |
| SaT040 | 2007 | HU | S | 1/1 | 0 | 0 | 22 |
| JJ2016 | 2007 | HU | S | 1/1 | 0 | 0 | 15 |
| QU300 | 2008 | AV | S | 1/1 | 0 | 0 | 22 |
| CD413 | 1995 | AV | S | 1/1 | 0 | 0 | 22 |
| CD390 | 1990 | HU | R | 1AC/1D | 1 | 0 | 22 |
| JMI025 | 2000 | HU | R | 1AC/1D | 1 | 0 | 31 |
| JJ2087 | 2003 | HU | S | 1/1 | 0 | 0 | 22 |
| JJ1996 | 2007 | AV | S | 1/6 | 0 | 0 | 22 |
| CD505 | 1983 | HU | S | 1/2 | 0 | 0 | 22 |
| CD455 | 2008 | AV | S | 1/2 | 0 | 0 | 22 |
| CD303 | 2001 | HU | S | 1/2 | 0 | 0 | 22 |
| CD466 | 1990 | AV | S | 1/1b | 0 | 0 | 35 |
| JJ1999 | 2007 | AV | S | 1/2 | 0 | 0 | 22 |
| CD436 | 1997 | HU | S | 1/2 | 0 | 0 | 22 |
| CD347 | 2006 | AV | S | 1/2 | 0 | 0 | 22 |
| CD456 | 2008 | AV | S | 1/2 | 0 | 0 | 22 |
| CD467 | 2009 | HU | S | 1A/1b | 0 | 0 | 35 |
| MVAST020 | 2010 | HU | S | 1A/1b | 1 | 1 | 41 |
| MVAST167 | 2010 | HU | S | 1A/1b | 1 | 0 | 41 |
| JJ2591 | 2006 | HU | S | 1/1b | 1 | 0 | 41 |
| JJ2055 | 2007 | HU | S | 1A/1b | 1 | 0 | 41 |
| QUC12 | 2008 | CA | S | 1/1b | 0 | 0 | 41 |
| U054 | 2010 | HU | S | 1/1b | 0 | 0 | 41 |
| QU090 | 2008 | HU | R | 1AB/3A | 0 | 0 | 41 |

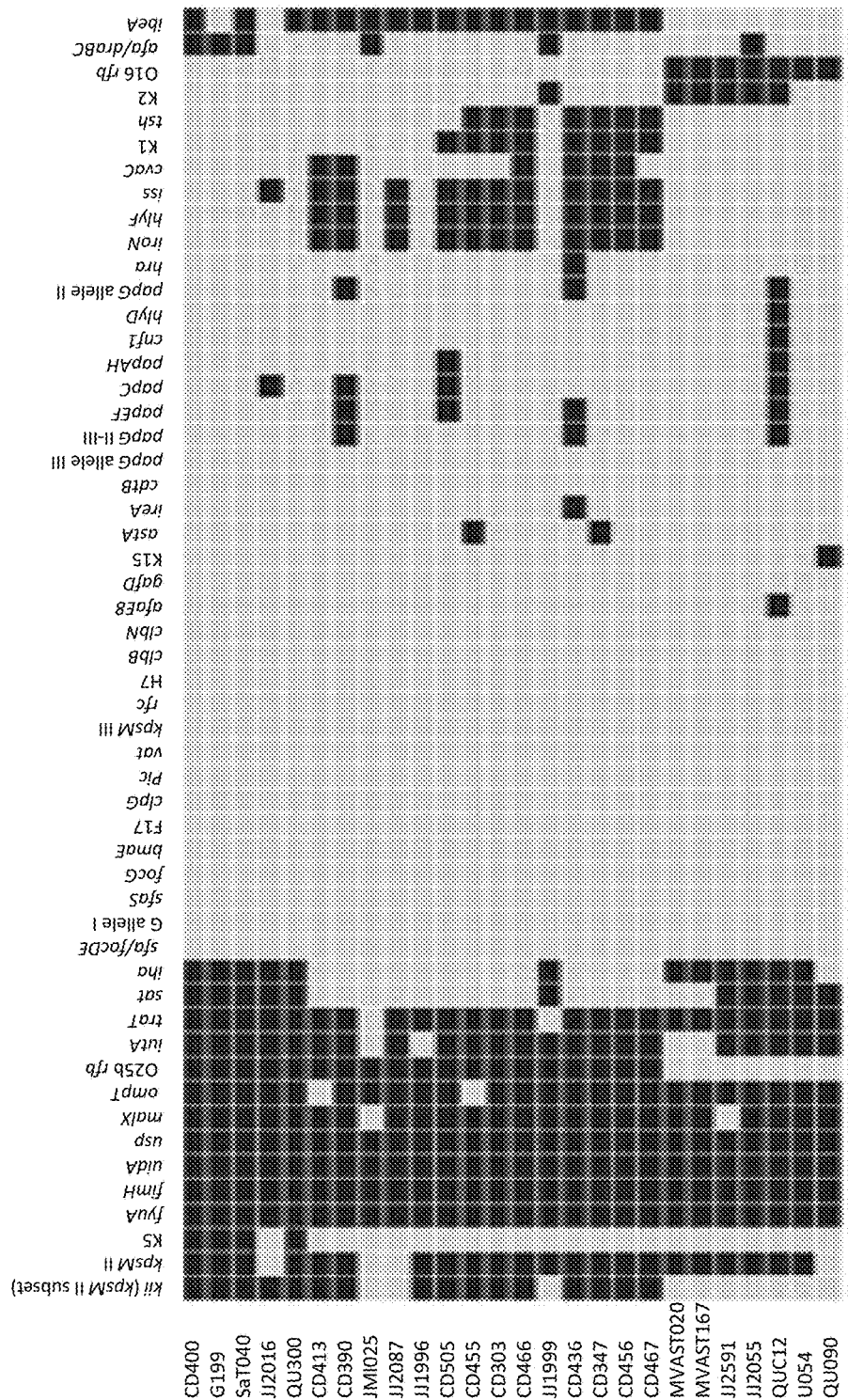

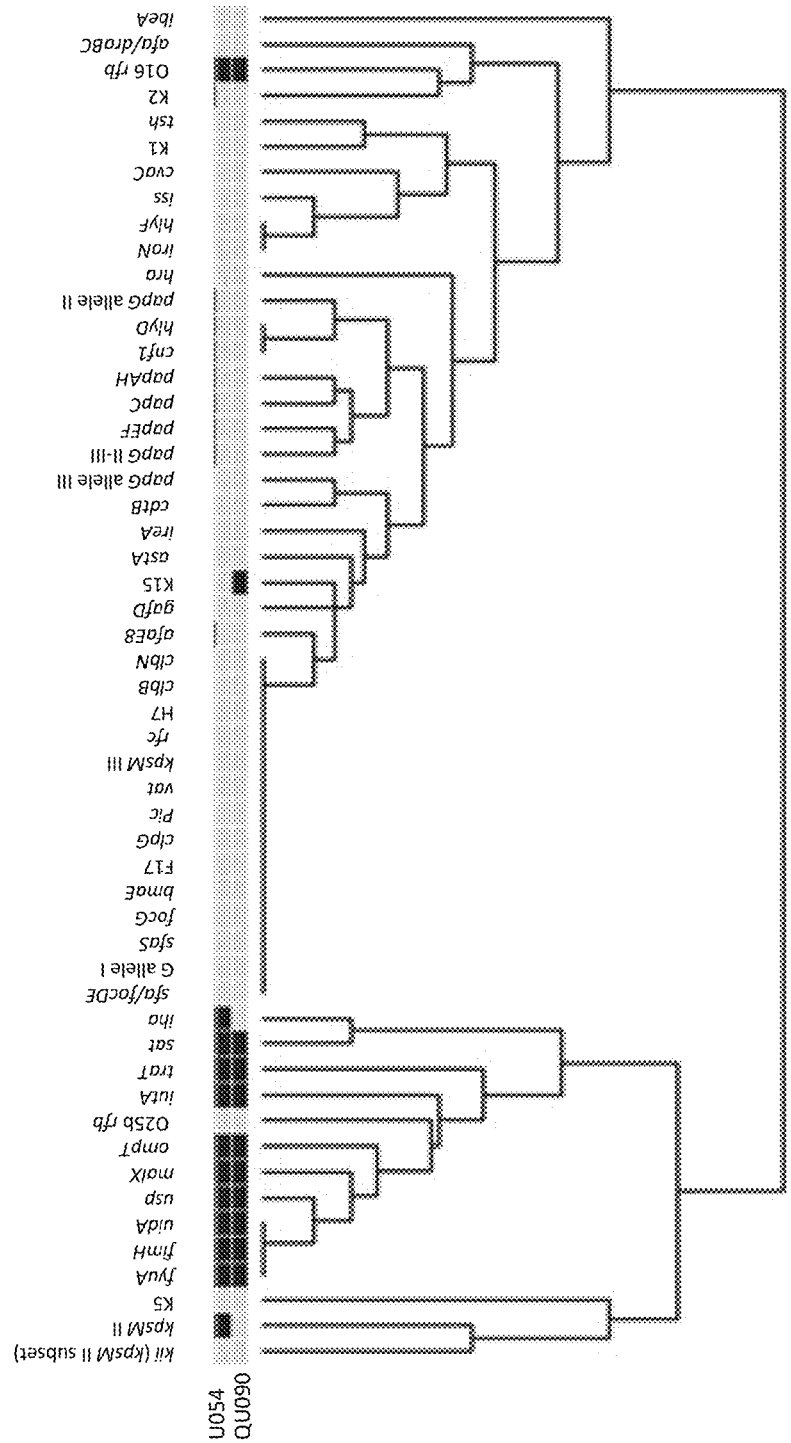
FIGURE 29 (cont.8)

PRIMERS, ASSAYS AND METHODS FOR DETECTING AN *E. COLI* SUBTYPE

CROSS-REFERENCE TO RELATED APPLICATION

The present application is the U.S. National Stage of International Application No. PCT/US2013/049164, filed on Jul. 2, 2013, which claims the benefit of U.S. Provisional Application No. 61/667,402 filed on Jul. 2, 2012, the contents of each of which are hereby incorporated by reference in their entireties for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 13,482 kilobyte ASCII (text) file named "Seq_List" created on Jan. 2, 2015.

TECHNICAL FIELD

The present invention relates to specific primers, probes, and single nucleotide polymorphisms (SNPs) distinct to a subtype of *E. coli*. The invention further relates to assay kits and methods for detecting the presence of the *E. coli* subtype.

BACKGROUND

Until recently, fluoroquinolones (FQs) have been the preferred agents for treating multiple types of bacterial infection, including urinary tract infections (UTIs), most of which are caused by *Escherichia coli*. FQ resistance, however, is increasingly prevalent in *E. coli*, leading the 2010 Infectious Diseases Society of America guidelines to recommend nitrofurantoin over FQs for empirical treatment of uncomplicated UTI (See, e.g. Gupta K, Hooton T M, Naber K G, et al. International Clinical Practice Guidelines for the Treatment of Acute Uncomplicated Cystitis and Pyelonephritis in Women: A 2010 Update by the Infectious Diseases Society of America and the European Society for Microbiology and Infectious Diseases. *Clin. Infect Dis.* 2011; 52:e103-e20), allowing some patients to progress to severe illness or death despite receipt of conventional empirical therapy (See, e.g., Owens R C, Johnson J R, Stogstill P, Yarmus L, Lolans K, Quinn J. Community Transmission in the United States of a CTX-M-15-Producing Sequence Type ST131 *Escherichia coli* Strain Resulting in Death. *J. Clin. Microbiol.* 2011; 49:3406-8).

In *E. coli*, although reduced FQ susceptibility may result from up-regulated efflux pumps and plasmid-regulated resistance mechanisms, high-level FQ resistance typically requires 1-2 point mutations within the quinolone resistance-determining regions (QRDRs) of both gyrA and parC, the chromosomal genes encoding the FQ targets DNA gyrase and topoisomerase IV, respectively. This has been shown, for example, in Hooper (2000) (Hooper D C., Mechanisms of action and resistance of older and newer fluoroquinolones. *Clin. Infect. Dis.* 2000; 31 (Suppl 2):S24-S8) and Hooper (2001) (Hooper D C. Emerging mechanisms of fluoroquinolone resistance. *Emerg. Infect. Dis.* 2001; 7:337-41). Because of its chromosomal basis, such FQ resistance has arisen in diverse *E. coli* clonal lineages, all of which presumably acquired QRDR mutations independently (See, e.g. Johnson J R, et al. Epidemic clonal groups of *Escherichia coli* as a cause of antimicrobial-resistant urinary tract infections in Canada, 2002-2004. *Antimicrob Agents Chemother* 2009; 53:2733-9; Cagnacci S, et al. European emergence of ciprofloxacin-resistant *Escherichia coli* clonal groups O25:H4-ST 131 and O15:K52:H1 causing community-acquired uncomplicated cystitis. *J Clin Microbiol* 2008; 46(8):2605-12; and Johnson J R, et al. *Escherichia coli* sequence type ST131 as the major cause of serious multi-drug-resistant *E. coli* infections in the United States (2007). *Clin Infect Dis* 2010; 51:286-94).

Despite the high clonal diversity of FQ-R strains, the past decade has seen the rapid emergence and global spread of a specific FQ-resistance-associated *E. coli* lineage, ST131, one of ≥1000 *E. coli* sequence types (STs), as defined by multi-locus sequence typing (MLST). However, it has been unknown whether ST131's association with FQ resistance is due to the frequent, independent emergence of resistance in different strains or, instead, expansion of a single resistant strain. Such sub-ST analysis is critical to the development of epidemiologic and clinical measures to address the ongoing emergence of FQ-resistant (FQ-R) *E. coli*.

The excess risk associated with the ST131 lineage was described in a number of previous publications.

Currently, there are a number of *E. coli* detection assays but they are either for general species confirmation or for identification of pathogenic lineages unrelated to FQ-resistance. Although assays exist for the detection of ST131, they do not differentiate between the most important sub-clones of ST131, H30-R and H30-Rx (as described below) and other ST131 sub-clones. There is a need for a kit, assay, and methods for detecting the presence of this high-risk sub-clones of *E. coli*.

SUMMARY

This disclosure demonstrates that the major source of the current FQ-resistance epidemic in *E. coli* is the rapid clonal expansion of a single strain within ST131, which over the past decade has become the most successful lineage of extra-intestinal *E. coli* overall, and especially of multi-drug-resistant *E. coli*. This discovery provides a novel perspective on the *E. coli* antimicrobial (e.g., FQ) resistance epidemic, with profound implications and opportunities.

Through extensive genomic and molecular epidemiologic investigations, two genetically distinct (sub-clones) of *E. coli*, referred here as "H30-R" and "H30-Rx," have been newly discovered. Disclosed herein is that H30-R and H30-Rx are disproportionately positively-correlated with antibiotic resistance and virulence. Both H30-R and H30-Rx are almost universally fluoroquinolone resistant and the H30-Rx subclone represents the majority of extended spectrum beta-lactamase producing ST131 isolates. Detection of these lineages by any means is highly predictive of resistance to a wide range of important antibiotics and thus can be used to direct antimicrobial therapy. Detection of these lineages is also predictive of negative clinical outcomes that may be avoided by adjuvant therapies.

As explained in greater detail below, H30-Rx is a subset of H30-R. Thus, any aspects of the present invention that may be used to detect H30-R may also be used to detect H30-Rx without differentiating H30-Rx from other sub-clones within the broader H30-R group. Similarly, treatments that are effective for an H30-R infection in a subject are generally effective for treatment of an H30-Rx infection in a subject.

The present invention provides primers, probes, and single nucleotide polymorphisms (SNP) for detecting distinct sub-types, or sub-clones, of E. coli, more particularly H30-R and H30-Rx. The primers are capable of amplifying one or more H30-R and H30-Rx genes, and the probes are capable of detecting the H30-R and H30-Rx genes and amplification products of the H30-R and H30-Rx bacterial sub-clones.

In one aspect of the invention, there are provided primers, probes, or single nucleotide polymorphisms (SNP) specific to the distinct subtypes of E. coli identified herein, i.e., H30-R and H30-Rx.

In another aspect of the invention, there are provided assay kits for detecting the presence of H30-R and H30-Rx. In some embodiments, the kit and assays comprise one or more primer pairs for amplification of an H30-R or H30-Rx bacteria. In some embodiments, the kit comprises one or more probes for detection of the presence of H30-R or H30-Rx bacteria. In some embodiments, the kit comprises: a) one or more primer pairs for amplification of H30-R or H30-Rx genes; and/or b) one or more probes for detection of at least one H30-R or H30-Rx gene. The probes may be immobilized in a carrier, for example, in the form of microarrays.

In another aspect, the invention provides a method of treating a subject with a bacterial infection comprising: a) detecting the presence of an E. coli ST131 H30-R subclone within a population of H30 subclones according to any of the preceding claims in a sample from the subject; and b) treating the subject with an antimicrobial agent that is not fluoroquinolone (FQ), gentamicin, or trimethoprim-sulfamethoxazole (TMP/SMX). In some embodiments, the method of treating a subject with a bacterial infection further comprises treating the subject with an antimicrobial agent selected from the group consisting of nitrofurantoin, fosfomycin, carbapenem, colistin, tigecycline, and amikacin.

In certain aspect, the invention relates to a method of detecting the presence of a CTX-M-15-associated E. coli subclone H30-Rx within a population of H30 subclones in a sample comprising detecting single nucleotide polymorphism 200 (SNP-200) and single nucleotide polymorphism 264 (SNP-264) in a fimH30 gene, wherein the presence of both SNP-200 and SNP-264 confirms the presence of H30-Rx.

In some embodiments, the invention is directed to a method of detecting the presence of Escherichia coli sequence type 131 (ST131) in a sample comprising detecting the presence of an allelic combination of gyrA1AB/parC1aAB wherein detection of the allelic combination confirms the presence of ST131 in the sample and the absence of the allelic combination indicates the absence of ST131 in the sample.

Aspects of the disclosed invention includes genetic signatures specific to H30-R and H30-Rx. Other aspects of the disclosed invention also include assays for detecting the H30-R and H30-Rx lineages, using these genetic signatures, for example, in order to diagnose H30-Rx infections, guide patient treatment and follow-up, screen at-risk patients (and/or their contacts) for H30-Rx colonization, detect and quantify H30-Rx from environmental samples, and detect and quantify H30-Rx contamination on meat, poultry and other food products. Aspects of the invention further include using such assays individually or in combination with other assays for the aforementioned purposes.

BRIEF DESCRIPTION OF THE DRAWINGS

Illustrative and exemplary embodiments of the invention are shown in the drawings in which:

FIG. 5 shows a distribution of fluoroquinolone-susceptible (FQ-S) and resistant (FQ-R) isolates among the seven fimH-based (H) ST131 sub-clones.

FIG. 21A and FIG. 21B shows resistance phenotypes and ESBL types among 71 ST131 isolates.

FIG. 23 shows a table with single-nucleotide polymorphisms in gyrA among 352 recent and historical Escherichia coli isolates of sequence type ST131.

FIG. 24 shows a table with single-nucleotide polymorphisms in gyrA among 352 recent and historical Escherichia coli isolates of sequence type ST131.

FIG. 27 shows a whole genome SNP-based phylogeny of *Escherichia coli* ST131 after removing SNPs from the recombinant regions and including strain AA86 as an outgroup. Phylogeny is based on 2,518 parsimony-informative and 9,533 total SNPs from throughout the genome. HI=0.044.

Figure 1:
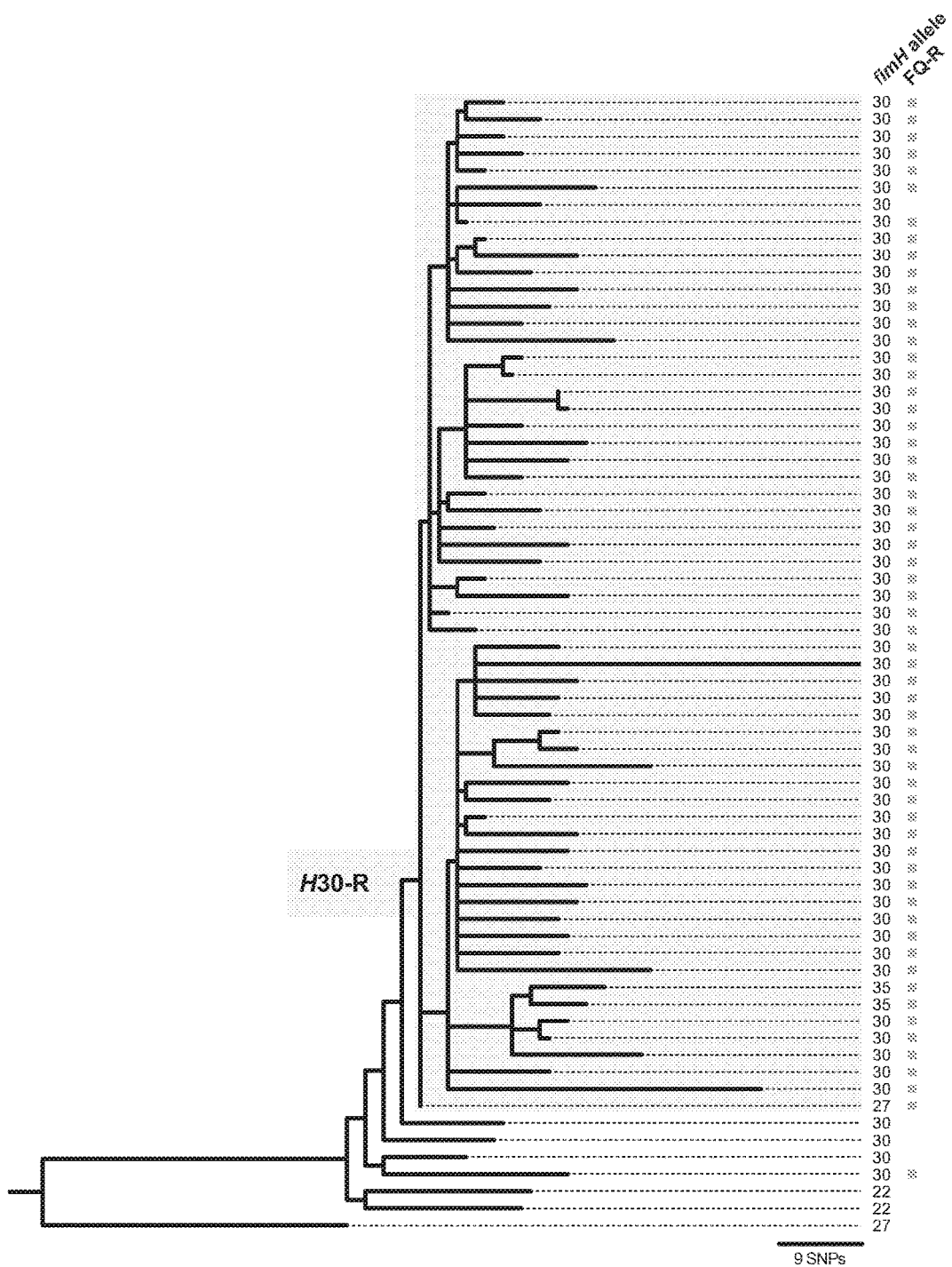
FIG. 1 shows a whole genome sequence based phylogenetic tree of the E. coli ST131 lineage. The H30-R subgroup is highlighted.

Elements and facts in the figures are illustrated for simplicity and have not necessarily been rendered according to any particular sequence or embodiment

DETAILED DESCRIPTION

Aspects and applications of the invention presented herein are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. The full scope of the inventions is not limited to the specific examples that are described below.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

"Homologues" of specific H30-Rx genes, primers, and sequences as used herein refers to nucleotide sequences having at least about 40%, including for example at least about any of 50%, 60%, 70%, 80%, 90%, 95%, 98%, 99%, or more sequence identity to the sequence of nucleotide sequences of genes, primers, or probes described herein.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., Eds, The Polymerase Chain Reaction, BirkHauser, Boston, Mass. (1994). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art.

As used herein, "amplifying" and "amplification" refers to a broad range of techniques for increasing polynucleotide sequences, either linearly or exponentially. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods may comprise thermal-cycling or may be performed isothermally. In various embodiments, the term "amplification product" includes products from any number of cycles of amplification reactions.

In certain embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643-50 (1991), M. Innis et al., PCR Protocols: A Guide to Methods and Applications, Academic Press, New York, N.Y. (1990), R. Favis et al., Nature Biotechnology 18:561-64 (2000), and H. F. Rabenau et al., Infection 28:97-102 (2000); Sambrook and Russell, Molecular Cloning, Third Edition, Cold Spring Harbor Press (2000) (hereinafter "Sambrook and Russell"), Ausubel et al., Current Protocols in Molecular Biology (1993) including supplements through September 2005, John Wiley & Sons (hereinafter "Ausubel et al.").

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labelling can be accomplished using any one of a large number of known techniques employing known labels, linkages, linking groups, reagents, reaction conditions, and analysis and purification methods. Labels include light-emitting compounds which generate a detectable signal by fluorescence, chemiluminescence, or bioluminescence (Kricka, L. in Nonisotopic DNA Probe Techniques (1992), Academic Press, San Diego, pp. 3-28). Another class of labels are hybridization-stabilizing moieties which serve to enhance, stabilize, or influence hybridization of duplexes, e.g. intercalators, minor-groove binders, and cross-linking functional groups (Blackburn, G. and Gait, M. Eds. "DNA and RNA structure" in Nucleic Acids in Chemistry and Biology, 2nd Edition, (1996) Oxford University Press, pp. 15-81). Yet another class of labels effect the separation or immobilization of a molecule by specific or non-specific capture, for example biotin, digoxigenin, and other haptens (Andrus, A. "Chemical methods for 5' non-isotopic labelling of PCR probes and primers" (1995) in PCR 2: A Practical Approach, Oxford University Press, Oxford, pp. 39-54).

A "primer," as used herein, is an oligonucleotide that is complementary to a portion of target polynucleotide and, after hybridization to the target polynucleotide, may serve as a starting-point for an amplification reaction and the synthesis of an amplification product. Primers include, but are not limited to, spanning primers. A "primer pair" refers to two primers that can be used together for an amplification reaction. A "PCR primer" refers to a primer in a set of at least two primers that are capable of exponentially amplifying a target nucleic acid sequence in the polymerase chain reaction.

The term "probe" comprises a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled. The probe can be an oligonucleotide that is complementary to at least a portion of an amplification product formed using two primers.

The term "modified" primer or probe may be used to describe a primer or probe modified as described for example in U.S. Pat. Nos. 7,408,051; 7,414,118; 7,585,649; 7,807,376; and U.S. patent application Ser. No. 12/889,273; and U.S. Pat. Nos. 7,517,978; 7,943,752; and U.S. patent application Ser. No. 13/052,382; and U.S. Pat. No. 7,408,051 and EP Patent No. 1902142B1, the entire contents of which are incorporated herein by reference.

The terms "complement" and "complementary" as used herein, refer to the ability of two single stranded polynucleotides (for instance, a primer and a target polynucleotide) to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary.

A "label" refers to a moiety attached (covalently or non-covalently), or capable of being attached, to an oligonucleotide, which provides or is capable of providing information about the oligonucleotide (e.g., descriptive or identifying information about the oligonucleotide) or another polynucleotide with which the labeled oligonucleotide interacts (e.g., hybridizes). Labels can be used to provide a detectable (and optionally quantifiable) signal. Labels can also be used to attach an oligonucleotide to a surface.

A "fluorophore" is a moiety that can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength.

The term "quencher" as used herein refers to a moiety that absorbs energy emitted from a fluorophore, or otherwise interferes with the ability of the fluorescent dye to emit light. A quencher can re-emit the energy absorbed from a fluorophore in a signal characteristic for that quencher, and thus a quencher can also act as a fluorophore (a fluorescent quencher). This phenomenon is generally known as fluorescent resonance energy transfer (FRET). Alternatively, a quencher can dissipate the energy absorbed from a fluorophore as heat (a non-fluorescent quencher).

As used herein the term "sample" refers to a starting material suspected of harboring a particular microorganism or group of microorganisms. A "contaminated sample" refers to a sample harboring a pathogenic microbe thereby comprising nucleic acid material from the pathogenic microbe. Examples of samples include, but are not limited to, food samples (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), water samples, environmental samples (e.g., soil samples, dirt samples, garbage samples, sewage samples, industrial effluent samples, air samples, or water samples from a variety of water bodies such as lakes, rivers, ponds etc.), air samples (from the environment or from a room or a building), forensic samples, agricultural samples, pharmaceutical samples, biopharmaceutical samples, samples from food processing and manufacturing surfaces, and/or biological samples. A "biological sample" refers to a sample obtained from eukaryotic or prokaryotic source. Examples of eukaryotic sources include animals, such as a human, a cow, a pig, a chicken, a turkey, a livestock animal, a fish, a crab, a crustacean, a rabbit, a game animal, and/or a member of the family Muridae (a murine animal such as rat or mouse). A biological sample may include blood, urine, feces, or other materials from a human or a livestock animal. A biological sample can be, for instance, in the form of a single cell, in the form of a tissue, or in the form of a fluid.

A sample may be tested directly, or may be prepared or processed in some manner prior to testing. For example, a sample may be processed to enrich any contaminating microbe and may be further processed to separate and/or lyse microbial cells contained therein. Lysed microbial cells from a sample may be additionally processed or prepares to separate, isolate and/or extract genetic material from the microbe for analysis to detect and/or identify the contaminating microbe. Analysis of a sample may include one or more molecular methods. For example, according to some exemplary embodiments of the present disclosure, a sample may be subject to nucleic acid amplification (for example by PCR) using appropriate oligonucleotide primers that are specific to one or more microbe nucleic acid sequences that the sample is suspected of being contaminated with. Amplification products may then be further subject to testing with specific probes (or reporter probes) to allow detection of microbial nucleic acid sequences that have been amplified from the sample. In some embodiments, if a microbial nucleic acid sequence is amplified from a sample, further analysis may be performed on the amplification product to further identify, quantify and analyze the detected microbe (determine parameters such as but not limited to the microbial strain, pathogenicity, quantity etc.).

As used herein "preparing" or "preparing a sample" or "processing" or processing a sample" refers to one or more of the following steps to achieve extraction and separation of a nucleic acid from a sample: (1) bacterial enrichment, (2) separation of bacterial cells from the sample, (3) cell lysis, and (4) nucleic acid extraction and/or purification (e.g., DNA extraction, total DNA extraction, genomic DNA extraction, RNA extraction). Embodiments of the nucleic acid extracted include, but are not limited to, DNA, RNA, mRNA and miRNA. Alternatively, nucleic acid extraction and purification may be bypassed.

As used herein, "presence" refers to the existence of a reaction, a product of a method or a process (including but not limited to, an amplification product resulting from an amplification reaction), or to the "presence" and "detection" of an organism such as a pathogenic organism or a particular strain or species of an organism.

As used herein, "detecting" or "detection" refers to the disclosure or revelation of the presence or absence in a sample of a target polynucleotide sequence or amplified target polynucleotide sequence product. The detecting can be by end point, real-time, enzymatic, and by resolving the amplification product on a gel and determining whether the expected amplification product is present, or other methods known to one of skill in the art.

The presence or absence of an amplified product can be determined or its amount measured. Detecting an amplified product can be conducted by standard methods well known in the art and used routinely. The detecting may occur, for instance, after multiple amplification cycles have been run (typically referred to an end-point analysis), or during each amplification cycle (typically referred to as real-time). Detecting an amplification product after multiple amplification cycles have been run is easily accomplished by, for instance, resolving the amplification product on a gel and determining whether the expected amplification product is present. In order to facilitate real-time detection or quantification of the amplification products, one or more of the primers and/or probes used in the amplification reaction can be labeled, and various formats are available for generating a detectable signal that indicates an amplification product is present. For example, a convenient label is typically a label that is fluorescent, which may be used in various formats including, but are not limited to, the use of donor fluorophore labels, acceptor fluorophore labels, fluorophores, quenchers, and combinations thereof. Assays using these various formats may include the use of one or more primers that are labeled (for instance, scorpions primers, amplifluor primers), one or more probes that are labeled (for instance, adjacent probes, TaqMan® probes, light-up probes, molecular beacons), or a combination thereof. The skilled person will understand that in addition to these known formats, new types of formats are routinely disclosed. The present invention is not limited by the type of method or the types of probes and/or primers used to detect an amplified product. Using appropriate labels (for example, different fluorophores) it is possible to combine (multiplex) the results of several different primer pairs (and, optionally, probes if they are present) in a single reaction. As an alternative to detection using a labeled primer and/or probe, an amplification product can be detected using a polynucleotide binding dye such as a fluorescent DNA binding dye. Examples include, for instance, SYBR® Green dye or SYBR® Gold dye (Molecular Probes). Upon interaction with the double-stranded amplification product, such polynucleotide binding dyes emit a fluorescence signal after excitation with light at a suitable wavelength. A polynucleotide binding dye such as a polynucleotide intercalating dye also can be used.

The probe may be RNA or DNA. Depending on the detection means employed, the probe may be unlabeled, radiolabeled, chemiluminescent labeled, enzyme labeled, or labeled with a dye. The probe may be hybridized with a sample in solution or immobilized on a solid support such as nitrocellulose, a microarray or a nylon membrane, or the probe may be immobilized on a solid support, such as a silicon chip or a microarray.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, may depend upon, for example, the nature of the nucleotide sequence, temperature, and buffer conditions. These conditions may also depend on what event is desired, such as hybridization, cleavage, or strand extension. An "isolated" polynucleotide refers to a polynucleotide that has been removed from its natural environment. A "purified" polynucleotide is one that is at least about 60% free, preferably at least about 75% free, and most preferably at least about 90% free from other components with which they are naturally associated.

The present disclosure, in some embodiments, describes assay utilizing molecular methods such as sequence specific amplification and detection that offer significant improvements in speed, sensitivity and specificity over traditional microbiological methods. Embodiments relate to design and development of molecular detection assays comprising identification of a target sequence that is present in the sequence type 131 (ST131) *E. coli* and its subclones (i.e., H30 and H30-Rx) to be detected and absent or divergent in organisms not to be detected.

Primers and Amplifying Kits

The present invention provides kits comprising primers for amplifying genes (e.g. gene variations) specific to H30-Rx and/or H30-R. The primers may comprise forward and reverse primers for amplifying the H30-Rx and/or H30-R genes by PCR methods, such as asymmetric PCR methods.

The forward and reverse primer of primer pairs described herein for amplification of the H30-Rx bacteria are typically 10-50 nucleotides, including for example 12-35 nucleotides, 15-25 nucleotides. In some embodiments, the 5'-end of the forward or reverse primer of the said primer pairs for amplification of the H30-Rx and/or H30-R bacteria is linked with a universal tagged sequence. The 5'-end of the said universal tagged sequence in some embodiments may be labeled with a fluorescent dye. Exemplary universal tagged sequences are well known in the art.

In some embodiments, the kit comprises at least about two different primer pairs. In some embodiments, the kit comprises at least about three different primer pairs. In some embodiments, the kit comprises at least about any of 3, 4, 5, 6, 7, 8, 9, 10, 20, 30, 40, or 50 different primer pairs. These different primer pairs may amplify one or more H30-Rx genes. In some embodiments, the kit comprises at least any of 1, 2, 3, 4, 5, 6, 7, 8, 9, 10 pairs of primers listed herein, or homologues thereof.

The primers in the Tables below can be used in assay kits for detection of the presence of H30-Rx and/or H30-R.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Qβ replicase system (Lizardi et al., 1988, BioTechnology 6:1197 1202), and the techniques disclosed in WO 90/10064 and WO 91/03573.

Examples of techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), transcription-based amplification (Kwoh et al., 1989, Proc. Natl. Acad. Sci. USA 86:1173 1177) and restriction amplification (U.S. Pat. No. 5,102,784).

Other exemplary techniques include Nucleic Acid Sequence-Based Amplification ("NASBA"; see U.S. Pat. No. 5,130,238), Q1 replicase system (see Lizardi et al., BioTechnology 6:1197 (1988)), and Rolling Circle Amplification (see Lizardi et al., Nat Genet 19:225 232 (1998)). The amplification primers of the present invention may be used to carry out, for example, but not limited to, PCR, SDA or tSDA. Any of the amplification techniques and methods disclosed herein can be used to practice the claimed invention as would be understood by one of ordinary skill in the art.

PCR is an extremely powerful technique for amplifying specific polynucleotide sequences, including genomic DNA, single-stranded cDNA, and mRNA among others. Various methods of conducting PCR amplification and primer design and construction for PCR amplification will be known to those of skill in the art. Generally, in PCR a double-stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification.

The DNA polymerase used in PCR is often a thermostable polymerase. This allows the enzyme to continue functioning after repeated cycles of heating necessary to denature the double-stranded DNA. Polymerases that are useful for PCR include, for example, Taq DNA polymerase, Tth DNA polymerase, Tfl DNA polymerase, Tma DNA polymerase, Tli DNA polymerase, and Pfu DNA polymerase. There are many commercially available modified forms of these enzymes including: AmpliTaq® and AmpliTaq Gold® both available from Applied Biosystems. Many are available with or without a 3- to 5' proofreading exonuclease activity. See, for example, Vent® and Vent®. (exo-) available from New England Biolabs.

Other suitable amplification methods include the ligase chain reaction (LCR) (e.g., Wu and Wallace, Genomics 4, 560 (1989) and Landegren et al., Science 241, 1077 (1988)), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NABSA). (See, U.S. Pat. Nos. 5,409,818, 5,554,517, and 6,063,603). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

Probes and Assay Kits for Detecting H30-Rx and/or H30-R

In some embodiments, the assay kits and assays comprise probes for detecting H30-Rx and/or H30-R. These probes are capable of hybridizing with the H30-Rx and/or H30-R gene products (including DNA or RNA transcribed from the genes) or amplification of the gene products. In some embodiments, the probes are about 15-50 nucleotides long, including for example about 20-30 nucleotides long. In some embodiments, the 5' end of the probes are linked with an oligonucleotide. For example, the 5' end of the probes may be linked with an oligo-dT that is about 10-35 nucleotides, including for example about 16-26 nucleotides.

In some embodiments, the assay kit comprises at least about two different probes. In some embodiments, the assay kit comprises at least about three different probes. In some embodiments, the assay kit comprises at least about any of 3, 4, 5, 6, 7, 8, 9, 10, 20, 30, 40, or 50 different probes. These probes may detect the same or different H30-Rx genes. In some embodiments, the assay kit comprises at least about any of 1, 2, 3, 4, 5, 10, 15, 20, or 21 probes listed in Tables 3a, 4, 7, and 8, or homologues thereof.

The assay kits of the present invention may further comprise other control probes, such as surface chemistry control probe, hybridization control probe, the target of the said hybridization control probe, and negative control probe.

The probes described herein can be immobilized on a carrier, such as a carrier made of silicon, glass slide modified with various functional groups or membranes with various functional groups, preferably glass slide with an aldehyde group.

In some embodiments, the probes described are immobilized in a microarray. "Microarray" and "array," as used interchangeably herein, comprises a surface with an array, preferably an ordered array, of putative binding (e.g., by hybridization) sites for a biochemical sample (target) which often have undetermined characteristics. In some embodiments, a microarray refers to an assembly of distinct probes immobilized at defined positions on a substrate.

Arrays may be formed on substrates fabricated with materials such as paper, glass, plastic (e.g., polypropylene, nylon, polystyrene), polyacrylamide, nitrocellulose, silicon, optical fiber or any other suitable solid or semisolid support, and configured in a planar (e.g., glass plates, silicon chips) or three dimensional (e.g., pins, fibers, beads, particles, microtiter wells, capillaries) configuration.

Probes forming the array may be attached to the substrate by any number of ways including, but not limited to, (i) in situ synthesis (e.g., high-density oligonucleotide arrays) using photolithographic techniques; (ii) spotting/printing at medium to low density on glass, nylon or nitrocellulose; (iii) by masking and (iv) by dot-blotting on a nylon or nitrocellulose hybridization membrane, probes may also be non-covalently immobilized on the substrate by hybridization to anchors, by means of magnetic beads, or in a fluid phase such as in microtiter wells or capillaries.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplified product is then contacted with a solid substrate, such as a glass slide, which is coated with an aldehyde or another reactive group which will form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., Proc. Natl. Acad. Sci. U.S.A. (1995) 93:10614-10619). Arrays can also be printed by robotics onto glass, nylon (Ramsay, G., Nature Biotechnol. (1998), 16:40-44), polypropylene (Matson, et al., Anal Biochem. (1995), 224(1): 110-6), and silicone slides (Marshall, A. and Hodgson, J., Nature Biotechnol. (1998), 16:27-31). Other approaches to array assembly include fine micropipetting within electric fields (Marshall and Hodgson, supra), and spotting the polynucleotides directly onto positively coated plates. Methods such as those using amino propyl silicon surface chemistry are also known in the art.

One method for making microarrays is by making high-density nucleotide arrays. Techniques are known for rapid deposition of polynucleotides (Blanchard et al., Biosensors & Bioelectronics, 11:687-690). Other methods for making microarrays, e.g., by masking (Maskos and Southern, Nuc. Acids. Res. (1992), 20:1679-1684), may also be used. In principle, and as noted above, any type of array, for example, dot blots on a nylon hybridization membrane, could be used. However, as will be recognized by those skilled in the art, very small arrays will frequently be preferred because hybridization volumes will be smaller.

The assay kits of the present invention may also include the reaction solutions for performing PCR and hybridization, and 50% dimethyl sulphoxide (DMSO) as the blank control of the hybridization reaction.

In certain embodiments, the assay kit further comprises instructions for using the assay kit for detecting H30-Rx. For example, the assay kit may comprise instruction on performing PCR reactions, hybridization reactions, and interpretation of hybridization results, and/or for carrying out methods described herein.

In some embodiments, the kit or assay further comprises software for analyzing experimental results using kits, assays or microarrays described herein.

Methods of Detecting H30-Rx and/or H30-R Bacteria

Also provided are methods for detection of the presence of H30-Rx and/or H30-R bacteria using the aforementioned assay kits for detection.

In some embodiments, there is provided a method for detecting a H30-Rx and/or H30-R bacteria, the method comprising: a) performing PCR using at least one primer pair that amplify genes distinct to the H30-Rx and/or H30-R bacteria; and b) hybridizing the amplified products with one or more probes there detect the distinct genes.

The concentrations of the forward and reverse primer of the PCR primer pairs for detection of H30-Rx genes can be equal or non-equal. For example, in some embodiments, one of the primers is tagged with a universal tagged sequence at its 5' end, and the concentration of the primer whose 5' end is linked with the said 5'-universal tagged sequence is 5-100 folds to the concentration of another primer. In some embodiments, the concentration of the tagged sequence is about 2.5 folds higher than that of the untagged sequence.

In some embodiments, the temperature cycles of the said PCR amplification includes two steps: the cycles in the first step are composed of denaturation, annealing and extension, comprising 10-25 cycles; the cycles in the second step are composed of denaturation and extension, including 10-25 cycles. In some embodiments, the denaturation temperature is 94° C., the annealing temperature is 50-70° C., preferably 55° C., and the extension temperature in the second step is 60-80°, preferably is 70° C.

In some embodiments, the PCR is a multiplex asymmetric PCR. In the multiplex asymmetric PCR of the present invention, DNA polymerase, dNTP, $Mg^{2+}$ concentration and the compounds of the buffer are same as that in traditional PCR, and they can be optimized according to different reactions. The difference lies in the primers: one gene-specific primer is same as that in traditional PCR, while another gene-specific primer is added an oligonucleotide which is unrelated to the target sequence. The concentrations of these two primers can be equal. The different gene-specific primers can be added the same tagged sequence. The temperature cycles of one exemplary multiplex PCR include two steps: the first step is same as the traditional PCR, including denaturation, annealing and extension. The annealing temperature is adjusted according to Tm of the gene-specific primer; similarly, the extension time can be adjusted according to the length of the amplified fragment. After about 20 cycles, the reaction begins to perform the second step. The temperature cycles of the second step only include denaturation and extension, and the temperature of extension is about 70° C. In the first 20 cycles of amplification reaction, the primer pairs can perform the common PCR due to the annealing temperature is equivalent to Tm of the gene-specific primers. While in the latter 20 cycles of amplification, only the tagged gene-specific primer can anneal to the target, so that the single-stranded products are produced. The primers included in the kit for detection of H30-Rx and/or H30-R bacteria are those disclosed herein, for example those listed in Tables 3a, 4, 7, and 8.

The technique and the conditions of the hybridization between probes and PCR products are well-known by those of ordinary skills in the art. For example, the hybridization conditions are the follows: the median strict hybridization condition is at 50-60° C., 5×SSC for 1-2 hours, then washing in 2×SSC, 0.1% SDS (pH8.0), and then washing in distilled water at room temperature for 2 min. The highly strict hybridization condition is at a higher temperature (such as at 65-70° C.). For high specificity, preferably the lower salt concentration and/or higher temperature are used, such as the salt concentration is 0.02 mol/L to 0.15 mol/L, and the temperature is 50° C. to 65° C.

In one example in the present invention, the reverse hybridization technique is used, that is, the probes are immobilized on the carrier. The appropriate carrier is preferably silicon, glass slide with various functional groups and the membranes (such as nylon membrane, nitrocellulose membrane) that are derivated by various functional groups (such as nitryl group), and the most preferable is the glass slide with an aldehyde group. The target from the samples is labeled; preferably fluorescence labeled PCR products, and then hybridized with the probes immobilized on the glass slide after denaturation. For hybridization, the temperature, ion strength, pH and other buffers are selected according to the probe length, composition and the melting temperature of the hybrid (namely the combination of the labeled PCR products and the probes). Wahl et al., Proc. Natl. Acad. Sci. USA. 76 (1979) 3683-3687.

In order to detect H30-Rx bacteria, the hybridization signals of the targets and the probes are detected and analyzed by, such as, typically the fluorescence scanner, and then analyzed the hybridization signals by an appropriate software.

The present invention also encompasses, single nucleotide polymorphism (SNP) specific to the H30-Rx and/or H30-R bacteria as shown below in Table 1. Accordingly, this invention also encompasses a kit comprising a pair of PCR primers, and a pair of SNP nested PCR primers useful in detection of H30-Rx and/or H30-R.

Identifying H30-Rx and/or H30-R using the disclosed assays, genetic signatures, or any other means will be useful to clinicians, veterinarians, diagnostic laboratories, microbiology labs, clinical diagnostics companies, researchers, food producers, food safety professionals, etc.

Clinicians can use the disclosed assays and other assays designed around the disclosed genetic signatures to accomplish, for example, the following: 1) predict recurrent urinary tract infections (UTIs); 2) predict fluoroquinolone resistance (or resistance to other antimicrobial drugs) and guide proper antimicrobial choice; 3) predict sepsis from UTI (urosepsis); 4) predict prolonged hospital stays; 5) predict development of complications and greater severity during the course of illness; 6) screen pregnant women for colonization and evaluate risk for complications such as neonatal meningitis; 7) predict the need for combination and prolonged antimicrobial therapy; 8) identify need for special interventions and adjuvant therapies (e.g., surgery, drainage, device removal, etc.) to resolve infection; 9) predict increased mortality risk; 10) prepare for possible step-up care (e.g., hospital admission, ICU transfer, etc.); 11) predict prolonged convalescence post-therapy; 12) prepare for increased risk of super-infection or secondary infection during or after therapy for index infection episode; and 13) predict increased risk for secondary diagnosis at time of initial diagnosis. Clinicians may use the disclosed assays to determine infection with H30-Rx or related sub-clones of E. coli.

Diagnostic and microbiology labs can use the disclosed assays and genetic signatures to identify H30-Rx and/or H30-R infections, colonization, as well as environmental and equipment contamination with H30-Rx and/or H30-R.

Diagnostic companies can use the disclosed signatures to develop additional assays for different molecular platforms, including but not limited to DNA sequencing, PCR, real-time PCR, MALDI-TOF, etc.

Food producers and food safety professionals may use the disclosed assays and genetic signatures to screen food products (e.g., meat, poultry, produce, etc.) for contamination with H30-Rx and/or H30-R strains. Animals and the production environment could be screened from farm to slaughter. Likewise, products from animals can be screened from carcass to retail.

Researchers may use the disclosed assays and genetic markers to continue investigating the association between H30-Rx and/or H30-R and clinical disease.

Detection of H30-Rx and/or H30-R strains with the disclosed signatures and assays will aid in clinical diagnosis, prognosis and help direct optimal therapies. The signatures and assays disclosed herein can also be used to screen patients, medical personnel, medical equipment, hospital environments, and food commodities for colonization and/or contamination with H30-Rx and/or H30-R to prevent infections and disease outbreaks.

Methods of Treating H30-Rx and/or H30-R Bacterial Infections

In some aspects, the present invention provides methods of treating an H30-Rx and/or H30-R bacterial infection in a subject. Because these subclones are generally resistant to fluoroquinolone (FQ), gentamicin, and/or trimethoprim-sulfamethoxazole (TMP/SMX) other antimicrobial agents should be used. In some embodiments, the oral agents nitrofurantoin and fosfomycin may be used to treat the infection. In other embodiments, the intravenous (IV) agents carbapenem, colistin, and tigecycline may be used. Often, amikacin is used to treat the infection.

Other antimicrobial agents that may be used to treat an H30-R and/or H30-Rx infection include, but are not limited to, neomycin sulfate, bacitracin, mupirocin, polymyxin, nitrofurantoin, rifampin, tetracycline, lysostaphin, and combinations thereof. Suitable antibiotic agents include, but are not limited to, beta-lactam antibacterials such as natural and synthetic penicillin type agents including penam penicillins (such as benzyl penicillin, phenoxymethyl penicillin, coxacillin, nafcillin, methicillin, oxacillin, amoxycillin, temocillin, ticarcillin, and the like), penicillinase-stable penicillins, acylamino and carboxypenicillins (such as piperacillin, azlocillin, mezlocillin, carbenicillin, temocillin, ticarcillin, and the like), and broader spectrum penicillins (such as streptomycin, neomycin, framycetin, apramycin, amikacin, spectinomycin, amoxycillin, ampicillin, and the like), cephalosporins, macrolides (such as tylosin, tilmicosin, aivlosin, erythromycin, azithromycin, spiramycin, josamycin, kitasamycin, and the like), lincosamides (such as lincomycin, clindamycin, pirlimycin, and the like), pleuromutilins (such as tiamulin, valnemulin, and the like), polypeptides, glycopeptides (such as vancomycin, and the like), polymixins (such as polymixin B, polymixin E, and the like), sulfonamides (such as sulfamethazine, sulfadiazine, silver sulfadiazine, sulfatroxazole, sulfamethoxypyridazine, sulfanilamide, sulfisoxazole, sulfamethizole, mafenide, and the like), chloramphenicol, thiamphenicol, florfenicol, tetracycline type agents (such as tetracycline, chlortetracycline, oxytetracycline, domeclocycline, doxycycline, minocycline, and the like), tiamulin, colistin, meropenem, sulbactam, tazobactam, methacycline, pyrimethamine, sulfacetamide, oxazolidinones, e.g., eperezolid, linezolid, N-((5S)-3-(3-fluoro-4-(4-(2-fluoroethyl)-3-oxy-1-piperazinyl)phenyl-2-oxy-5-oxazolidinyl)methyl)acetamide, (S)—N-((3-(5-(3-pyridyl)thiophen-2-yl)-2-oxy-5-oxazolidinyl)methyl) acetamide, 2,2-difluoro-N-({(5S)-3-[3-fluoro-4-(4-glycoloylpiperazin-1-yl)pheny-1]-2-oxo-1,3-oxazolidin-5-yl}methyl)ethanethioamide, (S)—N-((3-(5-(4-pyridyl)pyrid-2-yl)-2-oxy-5-oxazolidinyl)methyl)acetamide hydrochloride, and the like, aminoglycosides (kanamycin, tobramycin, netilmicin, and the like), aminocyclitols, amphenicol, ansamycin, carbaphenem, cephamycin, rifampicin, monobactam, oxacephem, streptogramins (such as quinupristin, dalfopristin, and the like), cycloserines, mupiocin, urea hydroxamates, antibiotic-type antineoplastic agents (such as aclarubicin, actinomycin D, actinoplanone, aeroplysinin derivative, Nippon Soda anisomycins, anthracycline, azinomicyin-A, busucaberin, bleomycin sulfate, bryostatin-1, calichemycin, chromoximycin, dactinomycin, daunorubicin, ditrisarubicin B, doxorubicin, doxorubicin-fibrinogen, elsamicin-A, epirubicin, erbstatin, esorubicin, esperamicin-Alb, fostriecin, glidobactin, gregatin-A, grincamycin, herbimycin, idarubicin, illudins, kazusamycin, kesarirhodins, menogaril, mitomycin, mitoxantorone, mutamycin, mycophenolate mofetil, neoenactin, oxalysine, oxaunomycin, peplomycin, pilatin, pirarubicin, porothramycin, pyrindamycin A, rapamycin, rhizoxin, rodorubicin, sibanomicin, siwenmycin, sorangicin-A, sparsomycin, steffimycin B, talisomycin, terpentecin, thrazine, tricrozarin A, zorubicin, systemic antibacterials (such as 2,4-diaminopyrimidine), nitrofuran sulfones, narbofloxacin, and the like, and combinations thereof.

The present invention is further defined in the following. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Unless otherwise noted, the methods are conventional methods in the following examples.

The contents of all references, patents, and published patent applications cited throughout this application, as well as the Figures, are incorporated herein by reference in their entirety for all purposes.

EXAMPLES

Example 1. Single Nucleotide Polymorphisms Associated with H30-Rx and/or H30-R

As disclosed herein, seven single nucleotide polymorphisms (SNPs) are identified that strongly associate with the H30-R and H30-Rx subgroups. These have been identified and are shown in Table 1.

Four of these SNPs are specific to the H30-R subclone on the phylogenetic tree shown in FIG. 1. Three of SNPs are specific to the H30-Rx subclonal group highlighted in FIG. 2. These SNPs can be detected by a wide range of molecular platforms (e.g. DNA sequencing, PCR, real-time PCR, MALDI-TOF, etc) to rapidly differentiate H30-R and H30Rx strains from other closely related strains.

Figure 2:
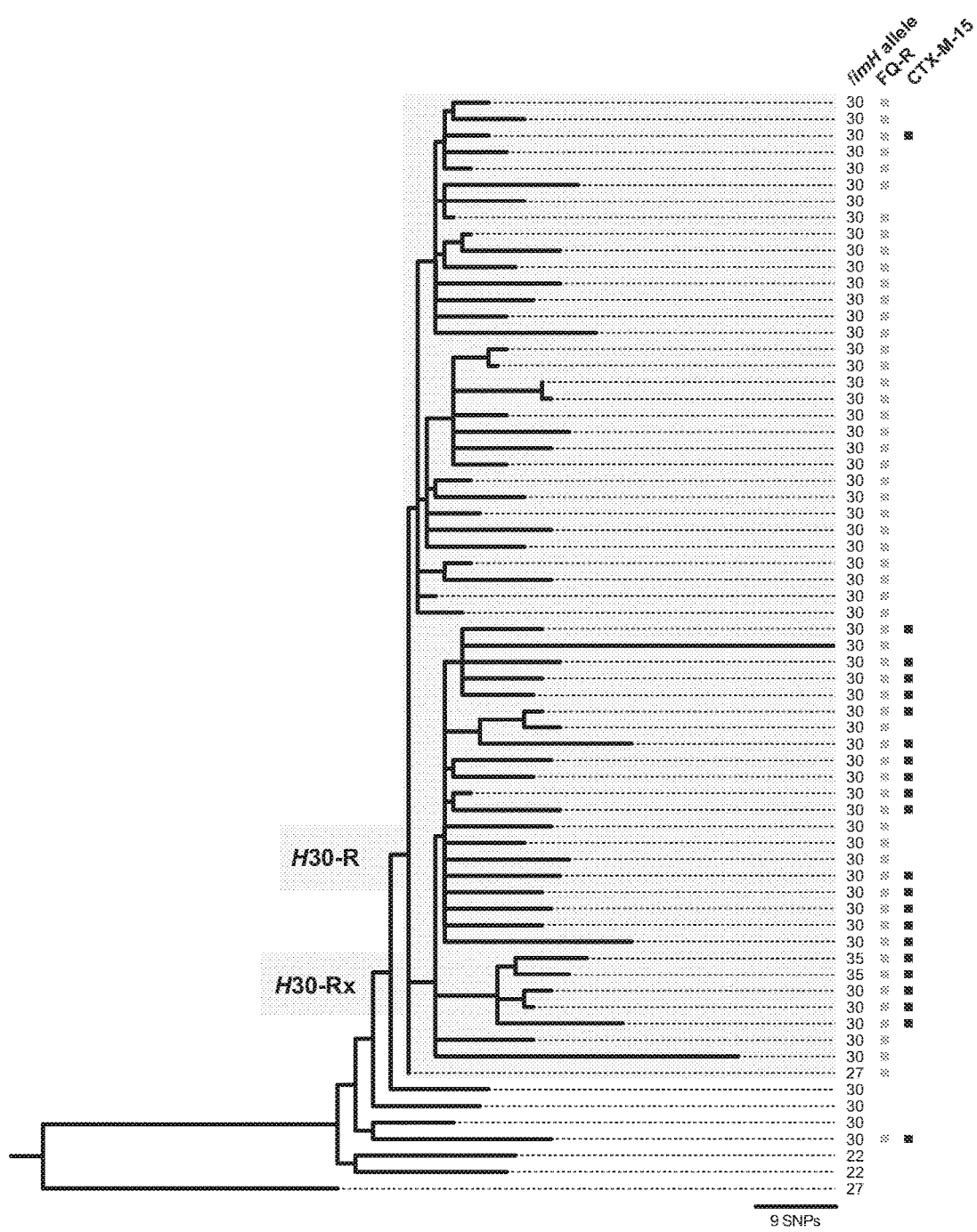
FIG. 2 shows a whole genome sequence based phylogenetic tree of the E. coli ST131 lineage. The H30-Rx subgroup is highlighted within the H30-R sublineage.

FIG. 1 presents a whole genome sequence based phylogenetic tree of the E. coli ST131 lineage. The H30-R subgroup is highlighted. FIG. 2 shows the H30-Rx subclone highlighted within the H30-R subclone.

According to certain implementations, additional genetic markers in the fimH30 allele, and in the gyrA1AB and parC1aAB alleles, are associated with the disclosed H30-R and H30-Rx subclones. These are discussed below in further detail below in Example 10: "FimH30 ST131 Primers" and in Example 11: "FQ Resistance Assays".

According to yet other implementations, further genetic markers are diagnostic for H30-R, H30-Rx and other important ST131 lineages. These are discussed below in further detail in Example 12: "ST131 Genetic Markers".

Example 2. Experimental Methods

The following experimental methods were used for the analyses discussed in Examples 3-9. Briefly, the fine clonal structure of 337 historical and recent E. coli isolates (227 fluoroquinolone-resistant, 90 fluoroquinolone-susceptible) representing sequence type ST131 was resolved by sequence analysis of the gyrA and parC fluoroquinolone resistance-determining loci and fimH for H sub-clone assignment, pulsed-field gel electrophoresis, and selective whole genome sequencing. The frequency of fimH-based ST131 H sub-clones was analyzed among >850 recent (2010-2011) consecutive clinical E. coli isolates in relation to antimicrobial resistance, single or recurrent urinary tract infections, sepsis, and non-ST131 sub-clones.

Isolates and Patients

The fine clonality of FQ resistance was analyzed among historical ST131 isolates (n=236) and recent clinical isolates, both ST131 (n=101) and non-ST131 (n=752). Historical ST131 isolates were selected from multiple published and unpublished collections to represent diverse years of isolation (1967-2009), FQ phenotypes, global locales, and ecological sources (humans, animals, food/environmental). The 853 recent ST131 and non-ST131 clinical isolates were consecutive human extraintestinal isolates recovered between October 2010 and January 2011 in clinical microbiology laboratories at five medical centers.

For analyses involving clinical manifestations, patients' medical records were retrospectively reviewed for 854 E. coli urine isolates, including 536 of the above-mentioned recent isolates, plus 318 replacement isolates collected in June, 2011. Patients were classified into three clinical categories: 1) single-episode bacteriuria (i.e., no repeat positive urine culture within 60d after the index culture) without diagnosed sepsis (n=715); 2) recurrent urinary tract infection (i.e., recurrent or persistent urinary symptoms, and/or a repeat positive urine culture), with or without diagnosed sepsis (n=118); and 3) bacteriuria with a sepsis diagnosis (n=31). The local institutional review boards approved the study protocol.

Sequence Analysis of Individual Loci

Isolates were assigned to a ST or ST complex (STc) based on MLST allele profiles available, for example, from the MLST Databases at the Environmental Research Institute at the University College Cork, Ireland. Within-ST clonal variation was resolved based on sequence variation in the E. coli type 1 fimbrial adhesin gen, fimH (positions 64-540). The QRDR of gyrA (6-570) and parC (1-573) was sequenced Maximum-likelihood trees were inferred for

TABLE 1

H30-R and H30-Rx signature SNPs.

| SNP position | SNP No. | CI | Subclone Indicator | SNP type | Gene start | base Δ | Codon Δ | AA Δ |
|---|---|---|---|---|---|---|---|---|
| 1460925 | SNP3446 | 1 | H30-R | sSNP | 1460592 | G→C | TCC→TCG | — |
| 1578171 | SNP3500 | 1 | H30-R | nSNP | 1577433 | C→T | TGT→CGT | C→R |
| 2767808 | SNP4907 | 1 | H30-R | sSNP | 2767681 | A→G | TGA→TAA | — |
| 3688298 | SNP10603 | 1 | H30-R | nSNP | 3688066 | G→A | AAG > AGG | K→R |
| 392950 | SNP200 | 1 | H30-Rx | nSNP | 392073 | C→T | GTG→GCG | V→A |
| 530994 | SNP264 | 1 | H30-Rx | sSNP | 530272 | G→A | GCA→GCG | — |
| 1994718 | SNP3729 | 1 | H30-Rx | iSNP | — | G→A | — | — |

Note:
SNP positions are based on the *Escherichia coli* NA114 (CP002797). Each SNP is identified as an intergenic SNP (iSNP), a non-synonomous SNP (nSNP), or a synonomous SNP (sSNP). Those SNPs that are indicative of H30-R are also present in H30-Rx. In contrast, those SNPs that are specific to H30-Rx are generally not present in the broader group of H30-R.

gyrA and parC separately using PAUP* (See, e.g. Swofford D L. PAUP* Phylogenetic Analysis Using Parsimony (*and other methods). Version 4. Sunderland, Mass.: Sinauer Associates; 2003).

Antimicrobial Susceptibility

Susceptibility to ciprofloxacin and 11 other antimicrobial agents was determined by disk diffusion, according to conventional methods. Intermediate susceptibility was considered resistant. The number of antimicrobial classes to which an isolate was resistant was calculated, with penicillins and cephalosporins counted separately.

Genome-Wide Analysis

Pulsed-field gel electrophoresis (PFGE) analysis was done for the 337 historical and recent ST131 isolates, according to conventional methods (see, e.g. Ribot E M, et al. Standardization of pulsed-field gel electrophoresis protocols for the subtyping of Escherichia coli O157:H7, Salmonella, and Shigella for PulseNet. Foodborne Pathog Dis 2006: 3:59-67). Whole genome sequence analysis was done for 22 representative ST131 isolates, as described in greater detail in FIGS. 3 and 4.

Pulsed-Field Gel Electrophoresis Analysis

The 352 historical and recent ST131 isolates underwent standardized XbaI pulsed-field gel electrophoresis (PFGE) analysis, with pulsotypes defined at >94% PFGE profile similarity to index strains for each pulsotype (Johnson J R, et al. Emerg Infect Dis 2012; 18:598-607). For dendrogram construction, a 24% subsample (n=85) was used to allow single page readability. The 85 ST131 isolates were selected randomly after deliberate inclusion of the earliest (plus a second, as available) representative of each fimH-gyrA-parC combination. The dendrogram was inferred within BioNumerics (Applied Maths) according to the unweighted pair group method based on Dice similarity coefficients.

Statistical Analysis

Fisher's exact test and McNemar's test were used to test unpaired and paired comparisons of proportions, respectively.

Example 3. H30-Rx Subgroup Identification

Advanced whole genome sequence-based methods were used to complement extensive molecular epidemiological investigations to identify the particularly virulent and antibiotic-resistant subgroup of E. coli, referred to here as H30-Rx. Prior to the discoveries disclosed herein, there were no published reports identifying this distinct subgroup. This disclosure reveals that H30-Rx is a genetically distinct group within a larger pathogenic E. coli lineage called ST131. According to the disclosure herein, H30-Rx is significantly associated with recurrent UTIs, sepsis, and antimicrobial resistance. Aspects of this disclosure include the identification of this highly virulent and genetically distinct subgroup, H30-Rx, and the identification of genetic signatures distinguishing H30-Rx strains from other E. coli ST131 strains. These signatures can be detected for surveillance, screening, diagnosis, prognosis, and therapeutic guidance.

The excess virulence associated with the H30-Rx was discovered through the use of the extensive molecular epidemiological investigations disclosed herein. The identified genetic signatures were revealed through sophisticated genetic investigations, including whole genome sequence-based phylogenetic studies and comparative genomics. The biological roles of many of these signatures are still unknown and would have been difficult, if not impossible, to identify by any other method.

Example 4. Sub-ST131 Analysis of FQ Resistance

Fluoroquinolone (FQ) resistance is increasingly prevalent in Escherichia coli. Although its molecular mechanisms are understood, its clonal origins are not.

It has been unknown whether ST131's association with FQ resistance is due to the frequent, independent emergence of resistance in different strains or, instead, expansion of a single resistant strain. Such sub-ST analysis is critical to the development of epidemiologic and clinical measures to address the ongoing emergence of FQ-resistant (FQ-R) E. coli. Accordingly, FQ resistance at the sub-ST level—for over 1,300 archived and freshly isolated ST131 and non-ST131 E. coli isolates—was analyzed by determining fine clonal diversity based on individual gene loci and whole genomes. Thereby, the clonal history of FQ resistance in ST131 and its impact on the clinical population dynamics of E. coli could be defined.

Example 5. FQ Resistance within ST131 is Associated with Specific Sub-Clones

To explore the sub-clonal structure of ST131, the 352 historical and recent ST131 isolates underwent MLST, fimH sequencing, and PFGE analysis. This identified seven distinct fimH-typing based (H) sub-ST131 clonal lineages (HIS, 122, H27, H30, H35, H41, 1194), and 185 unique PFGE pulsotypes, as shown in FIG. 3, below.

Figure 3:
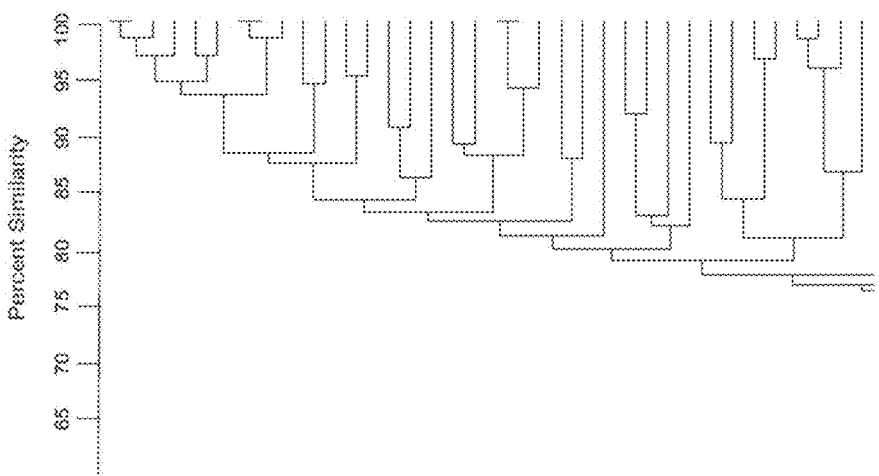
FIG. 3 shows an XbaI pulsed-field gel electrophoresis (PFGE)-based dendrogram for 85 sequence type ST131 Escherichia coli isolates (1967-2011).
Figure 4:
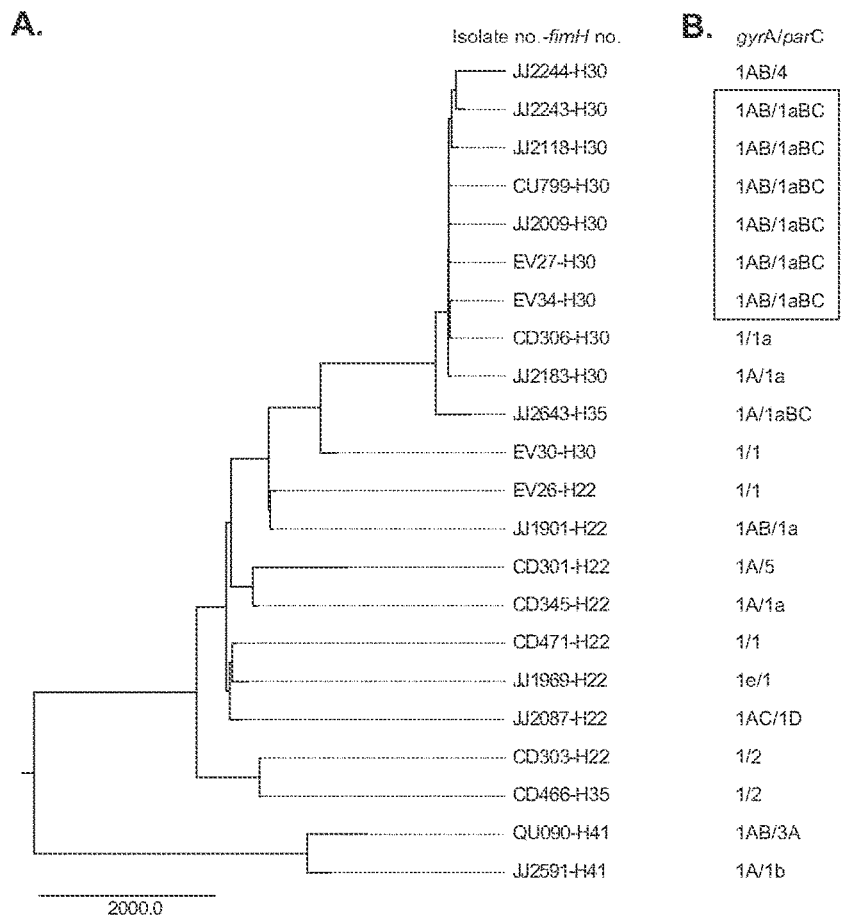
FIG. 4 shows Whole-genome phylogram for 22 sequence type ST131 Escherichia coli isolates.

FIG. 3 presents XbaI pulsed-field gel electrophoresis (PFGE)-based dendrogram for 85 sequence type ST131 Escherichia coli isolates (1967-2011). The 337 historical and recent ST131 isolates underwent standardized XbaI PFGE analysis. Pulsotypes were defined at ≥94% PFGE profile similarity. Dice similarity coefficient-based dendrograms were inferred within BioNumerics (Applied Maths) according to the unweighted pair group method. Abbreviations in the dendrogram labels: PFGE, pulsotype; Year, year of isolation or submission to reference laboratory; FQ, fluoroquinolone phenotype (R, resistant; S, susceptible); fimH, fimH (type 1 fimbrial adhesin) allele. Horizontal line separates isolates with ≥78% overall profile similarity (top of tree: n=37 isolates) from the remaining, less-similar isolates (basal region of tree: n=48 isolates). The 85 ST131 isolates used to construct the tree were selected randomly from the 337 total ST131 study isolates after deliberate inclusion of the earliest (plus a second, as available) representative of each of the fimH combination. Both FQ resistance and the fimH30 allele were significantly more prevalent in the upper tree region than the lower tree region (P<0.001 for each comparison, Fisher's Exact Test). Note: the incomplete segregation of fimH alleles within the tree may relate to the limited ability of PFGE to assess phylogenetic relatedness beyond the closest level (see: Johnson J R, et al. Epidemic clonal groups of Escherichia coli as a cause of antimicrobial-resistant urinary tract infections in Canada (2002-2004). Antimicrob Agents Chemother 2009; 53:2733-9). Marked by dots are 22 representative isolates selected for the whole genome sequence analysis (see FIG. 4).

Although there was broad general correspondence between fimH-based typing and PFGE profiles, isolates belonging to the same H sub-clones were often widely separated within the PFGE-based dendrogram. Accordingly, 22 selected isolates underwent full genome sequencing and phylogenetic analysis, which affirmed more strongly than PFGE the clonal relatedness of the major fimH allele groups, as presented in the whole-genome phylogram for 22 sequence type ST131 *Escherichia coli* isolates shown FIG. 4. Twenty-two historical and recent ST131 isolates, representing diverse fimH alleles and regions of the PFGE dendrogram (as indicated in Supplemental FIG. 1), underwent Illumina whole genome sequencing data and were aligned against a published *E. coli* ST131 genome (NA114, accession: CP002797) using the short-read alignment component of the Burrows-Wheeler Aligner. Mutations were identified in regions shared among all isolates (3,069,834 nt total) using SolSNP (http://sourceforge.net/projects/solsnp/) at minimum coverage of 10× with a minimum confidence score of 90% or greater.

Phylogenetic Tree.

Phylogenetic trees were generated using the maximum parsimony method in PAUP 4.0610 using 7,758 parsimony-informative characters (out of 21,698 total polymorphic nucleotides). The tree was rooted with an *E. coli* ST91 genome (AA86, accession: AFET01000001-3).

Combinations of gyrA/parC Alleles.

The alleles are listed in alignment with the corresponding isolates. Boxed is the clade of isolates from the H30 sub-clone that carry the H30 sub-clone's principal gyrA/parC allele combination (1AB/1aBC). For this clade, sequence diversity was estimated as 3.6 (range 3.2-4.1)×10'S/base by using the average pairwise diversity index (π) using MEGA version 4, and the molecular clock age was estimated as 7.4 (range 6.6-8.7) years by using a proposed clock models of $1.187 \times 10^{-6}$ synonymous mutations/site/year rate, with assumption of a neutral rate of accumulation of silent changes. (*) The actual time of emergence should be estimated by subtracting the molecular age from the average year of isolation.

The H sub-clones were next analyzed for associations with FQ resistance and prevalence shifts during the study period (1967-2011) (FIG. 5A). FIG. 5 presents the distribution of fluoroquinolone-susceptible (FQ-S) and resistant (FQ-R) isolates among the seven fimH-based (H) ST131 sub-clones. Area of circles is proportional to the relative abundance of the particular H sub-clone within the particular time period. Percentage values are shown relative to the total number of isolates within the particular time period. FIG. 5A shows the clonal distribution by time period. FIG. 5B shows the overall clonal distribution for all time periods combined, with the gyrA and parC allele combinations observed among FQ-S (in green) and FQ-R (in red) isolates labeled according to the nomenclature shown in FIG. 6. Asterisks identify the ST131 isolates' principal gyrA/parC allele combination (i.e., gyrA1AB/parC1aAB).

During the earliest period (1967-1999) only FQ-S sub-clones were encountered, predominantly H22 and H35. FQ-R isolates appeared first during 2000-2005, associated almost exclusively with the (newly-detected) H30 sub-clone. Thereafter the H30 sub-clone continued to account for nearly all (>97%) of FQ-R ST131 isolates, and constituted an increasing proportion of ST131 isolates overall.

Example 6. The FQ-R ST131 Clonal Expansion Involved Almost Exclusively a Single gyrA/parC Combination Among the 337 *E. coli* ST131 study isolates, sequence analysis of gyrA and parC identified seven gyrA alleles and 10 parC alleles (see the tables in FIGS. 23 and 24). The gyrA alleles all differed from another by no more than one single-nucleotide polymorphism (SNP), suggesting sequential evolution by point mutation (FIG. 6A). All FQ-S isolates possessed the putative ancestor allele gyrA1 or a derivative evolved from gyrA1 by either one silent SNP (gyr1a) or one amino acid replacement mutation, i.e., Lys to Ser, position 83 (gyrA1A) or Asp to Asn, position 87 (gyrA1B). In contrast, all FQ-R isolates possessed gyrA alleles that derived from gyrA1A by acquiring distinct secondary replacement mutations at position 87 Asp, i.e., gyrA1AB (to Asn), gyrA1AC (to Gly), and gyrA1AD (to Tyr).

Figure 6:
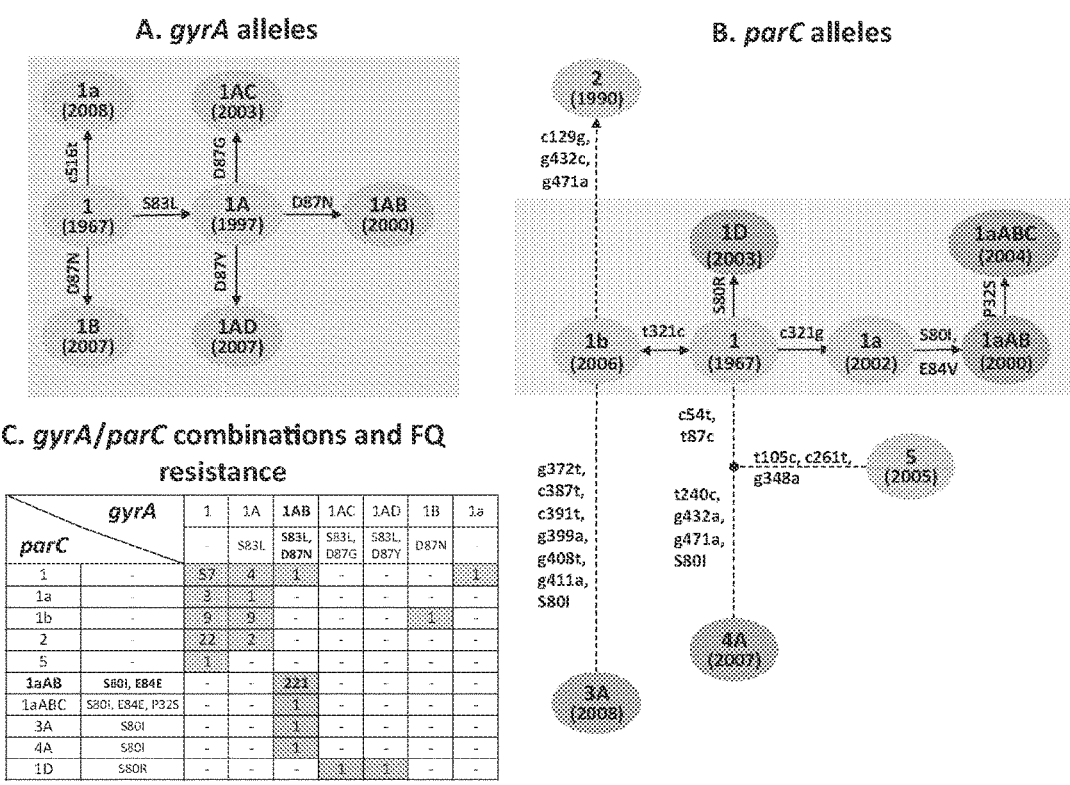
FIG. 6 shows ST131-associated gyrA and parC alleles: gene phylogeny and combinations.

FIG. 6 presents ST131-associated gyrA and parC alleles with gene phylogeny and combinations. In green are alleles (or allele combinations) associated with fluoroquinolone-susceptible isolates. In red are alleles (or allele combinations) associated with fluoroquinolone-resistant isolates. Single letter code for amino acid designations used are: G (Gly), D (Asp), E (Glu), I (Ile), L (Lys), N (Asn), P (Pro), R (Arg), S (Ser), V (Val), and Y (Tyr). FIGS. 6A and 6B show the phylogeny of the ST131-associated gyrA and parC alleles, respectively. Labels inside the circles are allele designations. In parentheses are earliest known year of isolation for the allele. Along the branches, lower-case numbers identify nucleotide positions with silent mutations, upper-case numbers identify amino acid positions with amino acid replacement mutations. Arrows show putative evolutionary order of mutations (double arrow between allele 1 and 1' indicates uncertainty of the order of allele emergence). Gray boxes show phylogenetic clades within which any nearest alleles differ by no more than a single silent nucleotide change.

FIG. 6C presents gyrA and parC allele combinations. Numbers inside cells represent number of ST131 isolates with the corresponding allele combination. The predominant allele combination among FQ-R isolates is shown in bold-face.

Among the 10 parC alleles, six closely related alleles appeared to have evolved sequentially by point mutation (FIG. 6B, gray box). Most FQ-S isolates possessed either the putative ancestor allele, parC1, or a derivative differing from parC1 by one silent SNP (parC1a or parC1b). In contrast, most FQ-R isolates possessed parC1aAB (parC1a plus replacement mutations Ser-80-Ile and Glu-84-Val), parC1aABC (parC1aAB plus a third replacement mutation, Pro-32-Ser), or parC1D (parC1 plus replacement mutation Ser-80-Arg). In marked contrast, the four remaining parC alleles differed from these mutation-derived alleles by multiple (≥3) silent SNPs, suggesting emergence by horizontal gene transfer and recombination rather than sequential point-mutation evolution. Two of these, parC4A and parC3A, occurred in FQ-R isolates and shared replacement mutation Ser-80-Ile.

The seven gyrA and 10 parC alleles occurred in ST131 in 18 combinations, of which 12 occurred among FQ-S and six among FQ-R isolates (FIG. 6C). Among FQ-S isolates the gyrA1/parC1 ancestral allele combination (FIG. 6C), occurred in slightly more than half of isolates and most H sub-clones (FIG. 5B). In contrast, among FQ-R isolates the gyrA1AB/parC1aAB combination predominated overwhelmingly (98% of isolates) (FIG. 6C), occurring almost exclusively within the H30 sub-clone (FIG. 5B).

Interestingly, 13 FQ-R isolates within the H30 sub-clone carrying the gyrA1AB/parC1aAB combination were from diverse non-human hosts, including dogs, cats, a primate, and a dolphin (not shown). Furthermore, H30 sub-clone isolates containing the gyrA1AB/parC1aAB combination, or its evolutionary predecessors gyrA1/parC1a and gyrA1A/parC1a, despite having diverse PFGE profiles (FIG. 4B), were tightly related at the whole-genome sequence level, indicating their emergence from a single strain as recently as about decade ago (FIG. 4B).

Example 7. The H30 ST131 Subclone is Associated with FQ Resistance Globally, Regardless of Source, and with CTX-M-15

Among the 236 historical ST131 isolates, the H30 ST131 subclone was closely associated with FQ resistance regardless of locale and source, and with ESBL production and blaCTX-M-15. Specifically, among US isolates the H30 subclone accounted for 122 of 126 (97%) FQ-R isolates, vs 1 of 75 (1%) FQ-S isolates (P<0.001), and among international isolates for 26 of 27 (96%) FQ-R isolates, vs 0 of 8 (0%) FQ-S isolates (P<0.001). Similarly, among human-source isolates it accounted for 136 of 140 (97%) FQ-R isolates, vs 0 of 32 (0%) FQ-S isolates (P<0.001), and among non-human-source isolates for 13 of 13 (100%) FQ-R isolates, vs 1 of 51 (2%) FQ-S isolates (P<0.001). The 13 non-human-source FQ-R H30 subclone isolates, all with the gyrA1AB/parC1aAB combination, represented diverse animal hosts, including dogs, cats, a primate, and a dolphin (data not shown). Regarding cephalosporin resistance, the H30 subclone accounted for 92 of 108 (85%) ESBL-positive isolates, vs 57 of 128 (45%) ESBL-negative isolates (P<0.001), and among ESBLpositive isolates for 63 of 68 (93%) blaCTX-M-15-positive isolates, vs 29 of 40 (73%) blaCTX-M-15-negative isolates (P<0.01).

Example 8. ST131's Principal FQ-R gyrA/parC Combination is Confined to ST131

Figure 7:
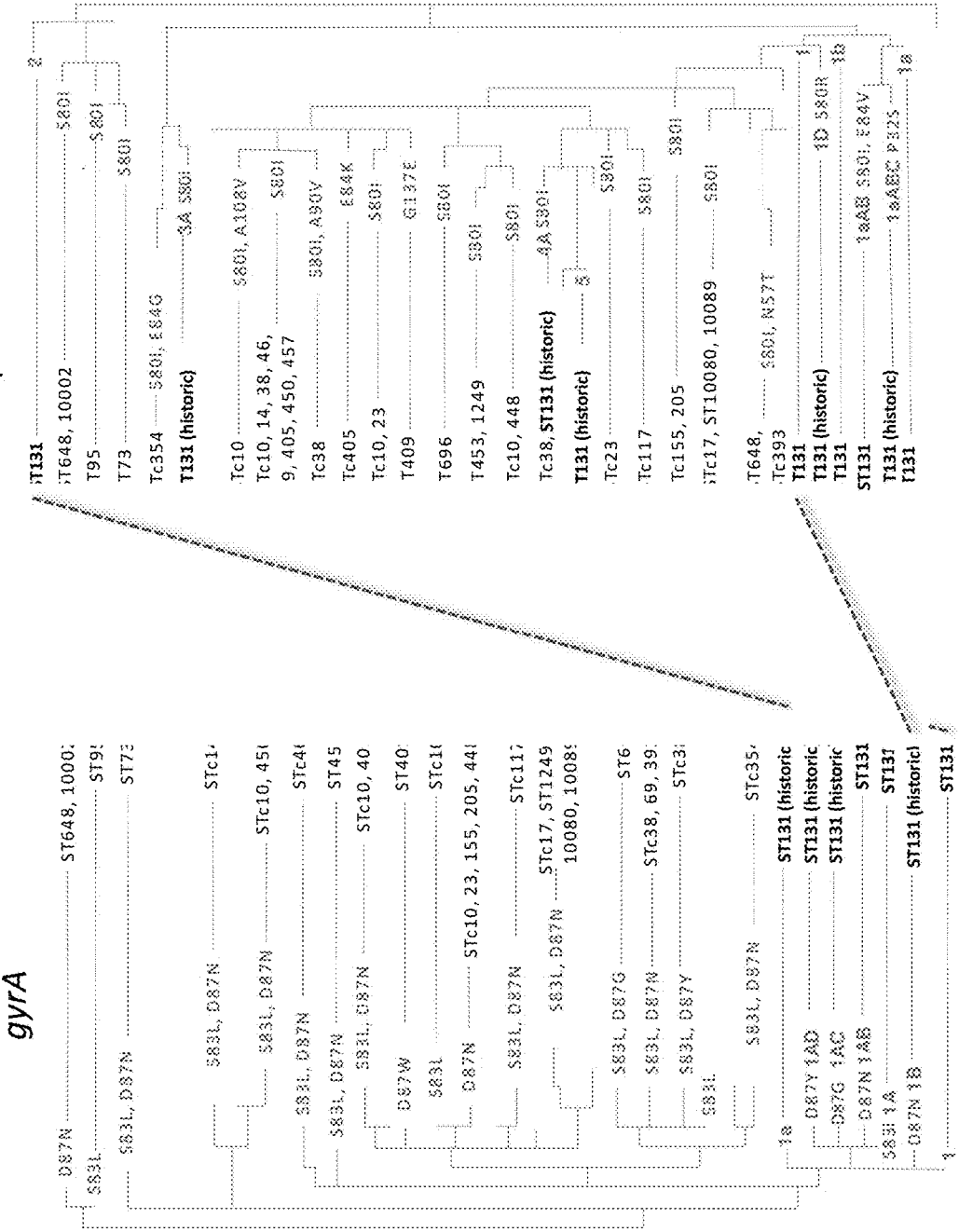
FIG. 7 shows phylogenetic trees for gyrA and parC for ST131 isolates and diverse fluoroquinolone (FQ)-resistant non-ST131 Escherichia coli isolates.

The gyrA and parC loci were sequenced also from selected recent non-ST131 clinical isolates, including all 78 non-ST131 FQ-R isolates, plus 63 FQ-S isolates representing the same STs as the FQ-R isolates (FIG. 7). To avoid false inferences of evolutionary relatedness from repeatedly acquired replacement mutations, phylogenetic trees were inferred for each gene separately based only on silent SNPs (green), before adding the resistance-associated replacement mutations (red).

FIG. 7 presents phylogenetic trees for gyrA and parC for ST131 isolates and diverse fluoroquinolone (FQ)-resistant non-ST131 *Escherichia coli* isolates. Trees were originally built based on silent variation only (green branches), then FQ-resistance-determining amino acid replacement changes were added manually (red branches and labels). "STc" indicates ST complexes (groups of closely related STs) within which the indicated alleles are found. Diagonal lines indicate gyrA1/parC combinations (dashed green, in FQ-susceptible ST131 isolates; dashed red, in FQ-R ST131 isolates; solid black, in FQ-R non-ST131 isolates). Blue/boldface labels show the 17 alleles found in ST131, named according to the nomenclature used in FIG. 6. "ST131 (historic)" marks ST131-associated alleles found only among the historic ST131 isolates.

In contrast to ST131's mutation-evolved gyrA and parC alleles, the four parC alleles suspected of being horizontally transferred into ST131 (FIG. 6B) clearly derived from non-ST131 regions of the parC tree (FIG. 7). Moreover, horizontal transfer of gyrA and parC occurred extensively throughout the species, most alleles appeared in multiple STs and/or in diverse combinations (FIG. 7, cross-links). In contrast, ST131's signature gyrA1AB and parC1aAB alleles occurred only within ST131.

Example 9. The H30 ST131 Sub-Clone Represents the Largest Clonal Expansion in *E. coli* and is Associated with Aggressive and Extensively Antimicrobial-Resistant Infections When analyzed across the 805 recent clinical *E. coli* isolates with associated clinical data, the H30 ST131 sub-clone was strongly associated with FQ resistance, accounting for 52% of all FQ-R isolates, but only 0.6% of all FQ-S isolates (P<0.001), whereas the six combined non-H30 ST131 sub-clones exhibited no such association (FIG. 8A). Clinically, the H30 sub-clone accounted for only 7.5% of patients with a single bacteriuria episode, without sepsis, but for 24.4% of patients with recurrent or persistent bacteriuria (P<0.001), and 21.2% of patients with bacteriuria plus sepsis (P=0.013), whereas the non-H30 ST131 isolates exhibited no such associations (FIG. 8B). It likewise greatly exceeded all other *E. coli* sub-clones as a cause of recurrent/persistent bacteriuria and sepsis (not shown).

Figure 8:
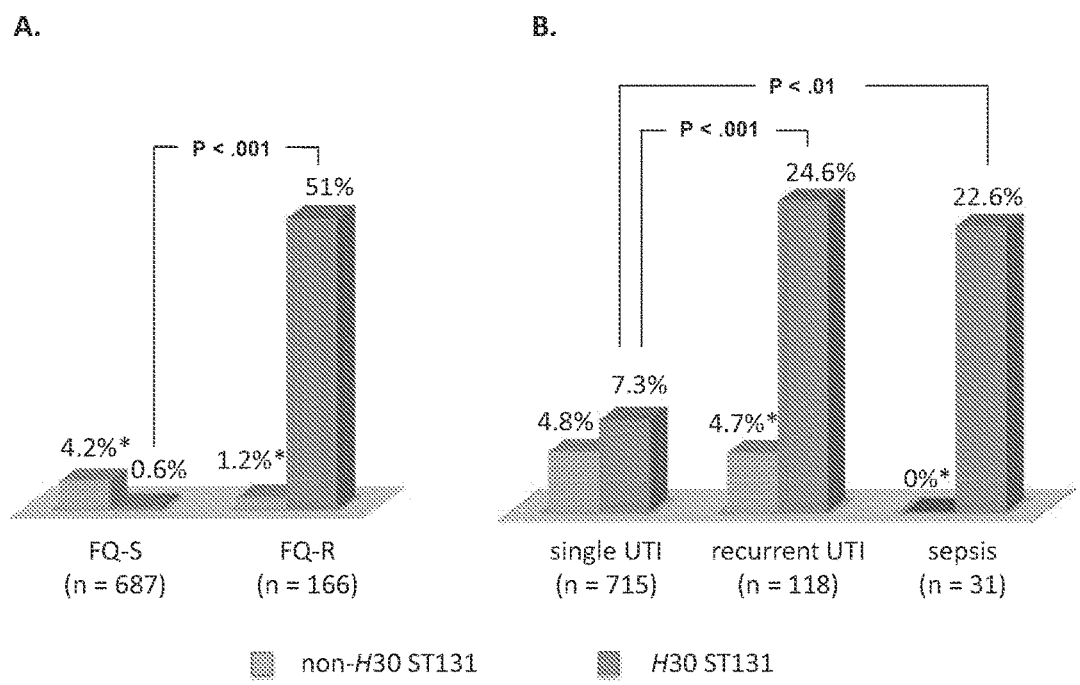
FIG. 8 shows the relative prevalence of the various ST131 H sub-clones in relation to fluoroquinolone resistance and clinical manifestations.

FIG. 8 shows relative prevalence of the various ST131 H sub-clones in relation to fluoroquinolone resistance and clinical manifestations. In grey—combined non-H30 isolates; in orange—H30 isolates. Percentage values above each column indicate the proportional contribution of the respective ST131 H sub-clone(s) to the particular category. Brackets indicate statistically significant differences (according to Fisher's exact test) between different resistances or clinical categories for prevalence of H30 sub-clone isolates. (For the combined non-H30 ST131 sub-clones, similar comparisons all yielded P>0.20). Asterisks indicate statistically significant prevalence differences (according to McNemar's test) between the non-H30 and H30 ST131 sub-clone isolates within a specific clinical or resistance category. FIG. 8A shows the prevalence of the various ST131 H sub-clones among fluoroquinolone-susceptible (FQ-S) and fluoroquinolone-resistant (FQ-R) *Escherichia coli* isolates. FIG. 8B shows the prevalence of the various ST131 H sub-clones among patients from three clinical categories (bacteriuria without recurrence or sepsis; bacteriuria with subsequent recurrence and/or persistence; and bacteriuria with sepsis).

Figure 9:
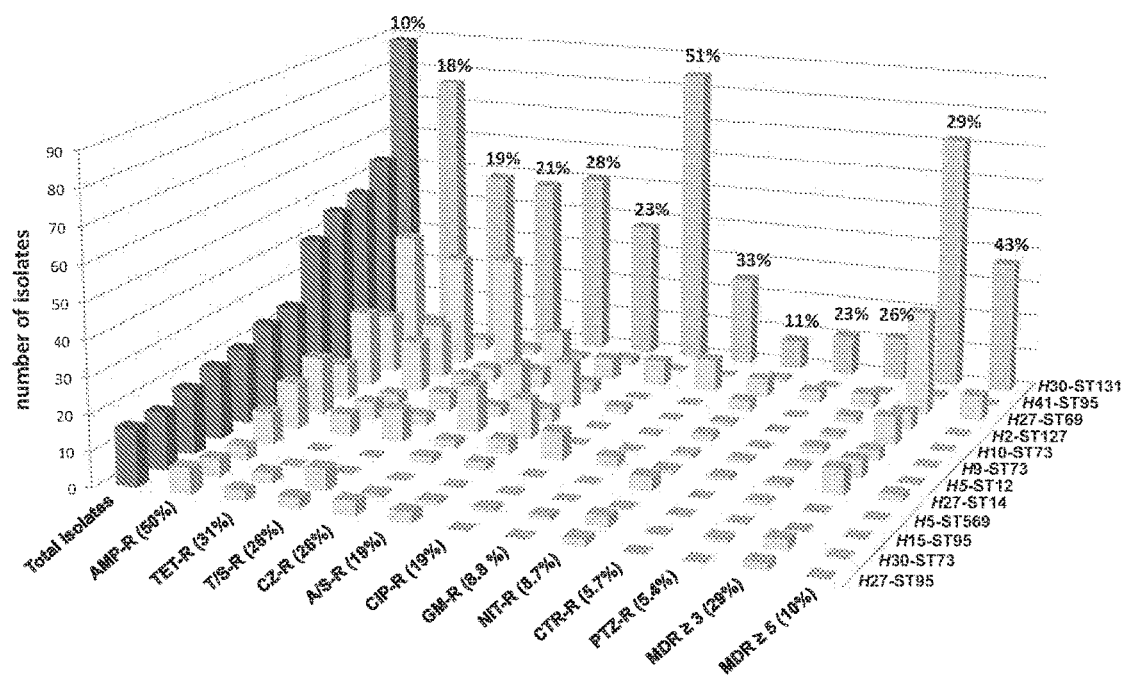
FIG. 9 shows the prevalence of the ST131 H30 sub-clone among all recent clinical Escherichia coli isolates.

Overall, among the recent clinical *E. coli* isolates from all STs, 185 total fimH-based sub-clones were identified. Of these, the H30 ST131 sub-clone was by far the most prevalent, followed only distantly by H sub-clones from historically dominant lineages such as ST95, ST69, ST127, and ST73 (FIG. 9). The H30 sub-clone also dominated for resistance not only to FQs but to all the other antimicrobial agents, individually and combined (e.g., ≥3 or 5 antimicrobial classes) (FIG. 9).

FIG. 9 presents the prevalence of the ST131 H30 sub-clone among all recent clinical *Escherichia coli* isolates. Orange indicates the H30 ST131 sub-clone. Grey indicates the 11 most-prevalent non-ST131 H sub-clones, among 853 total isolates. Each H sub-clone is labeled along the Z-axis according to its fimH allele and ST number. "Total isolates" columns are darker relative to the rest. The antimicrobials are listed along the X-axis in descending order of overall resistance prevalence, as shown in parentheses. The percentage numbers above the H30 columns indicate the H30 sub-clone's relative prevalence within each category of isolates (total or specific resistance phenotypes). AMP, ampicillin; TET, tetracycline; T/S, trimethoprim/sulfamethoxazole; CZ, cefazolin; A/S, ampicillin/sulbactam; CIP, ciprofloxacin; GM, gentamicin; NIT, nitrofurantoin; CTR, ceftriaxone; PTZ, piperacillin/tazobactam. No imipenem resistance was detected. MDR, multi-drug resistant (i.e., to ≥3 or ≥5 antimicrobial classes, with penicillins and cephalosporins counted separately).

These results demonstrate that, despite the frequent, independent emergence of FQ resistance within E. coli, including ST131, most current FQ-R E. coli clinical isolates originated from a single strain that emerged within ST131 about a decade ago and expanded rapidly to become what is now the dominant and most extensively multidrug-resistant lineage of extraintestinal pathogenic E. coli. Horizontal transfer and recombination involving gyrA and parC, newly identified here as a widespread mechanism for acquisition of chromosomal FQ resistance in E. coli, including ST131, has not affected this particular ST131 strain (sub-clone H30).

Although MLST has become the preferred method for clonal typing of bacterial pathogens, MLST-based clonal lineages (i.e., STs) of E. coli commonly comprise highly heterogeneous strains. For example, ST73, a major ST among extraintestinal pathogenic E. coli, also includes non-pathogenic strains Nissle1917 and ABU83972, which are used as probiotics. Recently, we have shown that STs can be divided into ecotypically distinct sub-clones by sequencing an internal region of fimH. This gene, encoding the type 1 fimbrial adhesin, is subject to more rapid evolution and horizontal gene transfer than the traditional MLST loci, which are expected to evolve neutrally. Our results establish that FQ resistance, a hallmark phenotype of (clonally diverse) ST131, is associated almost exclusively with a single fimH-based sub-clone, H30, carrying a single gyrA and parC allele combination. The close relatedness of H30 isolates on a genome-wide scale, which was more apparent with whole-genome sequencing than with PFGE analysis (which has limited phylogenetic validity), strongly suggests that, remarkably, the H30 sub-clone (and, thus, most current FQ-R E. coli) arose from a single strain as recently as one decade ago.

The finding of a predominantly single-strain origin of FQ resistance within ST131 and E. coli generally is quite surprising. Indeed, FQ resistance can potentially emerge in any E. coli strain by appropriate, analogous point mutations in the QRDR of the ubiquitous housekeeping genes gyrA and parC. Our study confirmed this, and newly documents that FQ resistance-conferring gyrA and parC alleles exhibit extensive horizontal mobility, thereby disseminating FQ resistance rapidly among different E. coli STs. Even within ST131, FQ resistance-conferring parC alleles have entered multiple times via horizontal transfer. Nevertheless, a single allelic combination—gyrA1AB/parC1aAB—has achieved predominance within ST131 and, consequently, the E. coli species overall.

The observed tight linkage between a single gyrA/parC combination and the H30 ST131 sub-clone could conceivably be due to superior FQ resistance, commensal fitness, and/or pathogenicity of this lineage, compared with other E. coli. Greater FQ resistance, if present, could represent an effect of the distinctive Glu-84-Val parC replacement mutation, which occurs in ST131's hallmark parC1aAB allele along with the widespread Ser-80-Leu mutation. Further, although plasmid-borne FQ resistance and up-regulated efflux pumps are uncommon in ST131, other traits of the H30 sub-clone could potentially augment its resistance, e.g., by blocking FQ entry or increasing intracellular FQ inactivation.[5] Although FQ minimum inhibitory concentrations (as assessed for selected isolates by Etest, bioMérieux) were not discernibly higher for the H30 sub-clone than other FQ-R ST131 sub-clones or gyrA/parC combinations (all, >32 mg/L; not shown), such in vitro testing may not reflect resistance phenotypes in vivo.

Regarding commensalism, resistance-conferring mutations in housekeeping genes may decrease overall bacterial fitness when antimicrobial selective pressure is absent, unless compensatory mutations have co-evolved with the resistance. Therefore, if the ST131 H30 sub-clone has compensated for the commensal fitness costs of its resistance mutations more successfully than other FQ-R lineages, it might have a competitive advantage by being more stable. In this regard, the H30 sub-clone's broad host range may also promote dissemination.

Finally, the H30 sub-clone might be more fit in the pathogenic niche, which, in combination with its FQ resistance, could underlie its rapid rise to clinical dominance over other E. coli. Indeed, within our collection of consecutive recent extraintestinal E. coli clinical isolates, the H30 ST131 sub-clone accounted for over 10% of isolates overall, but for nearly a quarter of index urine isolates from patients with sepsis or recurrent UTI. Although previous studies did not appreciate the nearly exclusive single-strain origin of FQ-resistant ST131 isolates, their documented prevalence values suggest that in some patient populations the H30 ST131 sub-clone could constitute up to 30% of all E. coli isolates and two-thirds or more of those resistant to FQs and/or extended-spectrum cephalosporins. The current dominance of the H30 subclone clearly surpasses such common lineages as ST69 ("clonal group A"; associated with trimethoprim-sulfamethoxazole resistance) and the highly pathogenic classic extraintestinal lineages ST95, ST73, and ST127. Heightened pathogenicity of the H30 sub-clone, if present, could be due to gene mutations or mobile genes that confer, for example, greater ability to avoid immune surveillance or to be shed extensively from an infected host.

Discovery of the basis for the H30 ST131 sub-clone's superior fitness should provide further useful insights into mechanisms of FQ resistance and pathogenicity in E. coli. Additionally, recognition of the H30 ST131 sub-clone has direct clinical implications. First, rapid diagnostics that detect this single-strain lineage could guide improved selection of empirical antimicrobial therapy for patients in whom FQ-R E. coli are of concern. Second, identification of relevant reservoirs and transmission pathways of the H30 sub-clone, and development of effective interventions against them, could limit its spread. Third, development of an effective vaccine could help protect at-risk hosts. Thus, the tools and methods provided herein will be useful in preventing and managing FQ-R E. coli infections. The Study was conduct with large and diverse study population for comparison of ST131 and non-ST131 E. coli, the use of advanced molecular modalities to define sub-ST131 clonal structure, the clonal phylogenetic analysis of mutations in gyrA and parC, and the assessment of clinical correlates.

In summary, of the fluoroquinolone-resistant ST131 isolates, 97% represented a single fimH-based H30 sub-clone (among seven total H sub-clones), which we have named H30-Rx. H30-Rx expanded abruptly after the year, 2000, and was highly homogeneous on the genomic level, indicating a single-strain origin. The H30-Rx's fluoroquinolone resistance corresponded with a unique gyrA/parC allele combination. Unlike other ST131 sub-clones, H30-Rx was significantly associated with fluoroquinolone resistance, recurrent urinary tract infections, and clinical sepsis. Moreover, among current E. coli clinical isolates, the H30 sub-clone (H30-Rx) was the most prevalent sub-clone, both overall and within each resistance category.

Most current fluoroquinolone-resistant E. coli clinical isolates, and a plurality of multi-drug-resistant E. coli isolates, are descendants of a single, rapidly expanding and clinically aggressive strain within ST131. Focused attention to this strain is essential to controlling the current epidemic of fluoroquinolone and multi-drug-resistant *E. coli*.

Example 10. FimH30 ST131 Primers

FimH30 Specific ST131 PCR Protocol

Table 2 shows PCR parameters according to some embodiments. A person of ordinary skill in the art would be aware of modifications to these parameters that remain within the scope of this disclosure.

TABLE 2

| Cycles | Degrees (C.) | Time |
|---|---|---|
| 1 | 95 | 8 minutes |
| 30 | 94 | 20 seconds |
|  | 68 | 45 seconds |
| 1 | 72 | 5 minutes |
| 1 | 4 | Extended period |

Table 3 shows controls for the fimH30 specific ST131 protocol according to some embodiments.

TABLE 3

Controls for fimH 30 PCR

| Strain # | fimH allele # | fimH30 PCR (354 bp) | udiA (508 bp) | ST |
|---|---|---|---|---|
| EV-4 | 30 | + | + | 131 |
| EV-56 | 30 | + | − | 131 |
| EV-02 | 148 | − | + | 131 |
| EV-03 | 41 | − | + | 131 |
| EV-26 | 126 | − | + | 131 |
| EV-35 | 22 | − | + | 131 |
| EV-69 | 35 | − | + | 131 |
| EV-72 | 89 | − | + | 131 |
| MG1655 | − | − | + | non-131 |

In certain embodiments, the following primers may be used to amplify the allele 30 of fimH (encoding a variant of the type 1 fimbrial adhesion) corresponding with the main FQ-resistance-associated subset within ST131, the H30 subclone.

```
Forward primer (fimH30F-21):
                                  (SEQ ID NO: 1)
CCGCCAATGGTACCGCTATT Reverse primer (fimH30R-20):
                                  (SEQ ID NO: 2)
CAGCTTTAATCGCCACCCCA
```

Clustal was used to align the Veronika/Evgeni Library of fimH alleles to find 2 ST131 O25b FQ-R fimH30 SNPs. Primers were then developed and are highlighted in the sequences below.

```
fimH30 allele with forward and reverse primers
in lowercase:354 bp product
                                  (SEQ ID NO: 3)
TTCGCCTGTAAAAccgccaatggtaccgctattCCTATTGGCGGTGGCAG

CGCTAATGTTTATGTAAACCTTGCGCCTGCCGTGAATGTGGGGCAAAACC

TGGTCGTAGATCTTTCGACGCAAATCTTTTGCCATAACGATTATCCGGAA

ACCATTACAGACTATGTCACACTGCAACGAGGCTCGGCTTATGGCGGCGT

GTTATCTAATTTTTCCGGGACCGTAAAATATAGTGGCAGTAGCTATCCAT

TTCCGACTACCAGCGAAACGCCGCGGGTTGTTTATAATTCGAGAACGGAT

AAGCCGTGGCCGGTGGCGCTTTATTTGACGCCTGTGAGCAGTGCGGGtg gggtggcgattaaagctgGCTCATTAATTGCCGTGCTTATTTTGCGACAG

ACCAACAACTATAACAGCGATGATTTCCAGTTTGTGTGGAATATTTACGC

CAATAATGATGTGGTGGTGCCTACTGGCGGCTGCGATGTT
```
*Note:
fimH allele sequences that also share both these 2 SNPs are 99, 163-165, 196, and 214.

NA114 ST131 from Genebank Sequence of Full Length fimH Gene:

```
                                  (SEQ ID NO: 4)
ATGAAACGAGTTATTACCCTGTTTGCTGTACTGCTGATGGGCTGGTCGGT

AAATGCCTGGTCATTCGCCTGTAAAACCGCCAATGGTACCGCTATTCCTA

TTGGCGGTGGCAGCGCTAATGTTTATGTAAACCTTGCGCCTGCCGTGAAT

GTGGGGCAAAACCTGGTCGTAGATCTTTCGACGCAAATCTTTTGCCATAA

CGATTATCCGGAAACCATTACAGACTATGTCACACTGCAACGAGGCTCGG

CTTATGGCGGCGTGTTATCTAATTTTTCCGGGACCGTAAAATATAGTGGC

AGTAGCTATCCATTTCCGACTACCAGCGAAACGCCGCGGGTTGTTTATAA

TTCGAGAACGGATAAGCCGTGGCCGGTGGCGCTTTATTTGACGCCTGTGA

GCAGTGCGGGTGGGGTGGCGATTAAAGCTGGCTCATTAATTGCCGTGCTT

ATTTTGCGACAGACCAACAACTATAACAGCGATGATTTCCAGTTTGTGTG

GAATATTTACGCCAATAATGATGTGGTGGTGCCTACTGGCGGCTGCGATG

TTTCTGCTCATGATGTCACCGTTACTCTGCCGGACTACCCTGGTTCAGTG

CCAATTCCTCTTACCGTTTATTGTGCGAAAAGCCAAAACCTGGGGTATTA

CCTCTCCGGCACAACCGCAGATGCGGGCAACTCGATTTTCACCAATACCG

CGTCGTTTTCACCAGCGCAGGGCGTCGGCGTACAGTTGACGCGCAACGGT

ACGATTATTCCAGCGAATAACACGGTATCGTTAGGAGCAGTAGGGACTTC

GGCGGTAAGTCTGGGATTAACGGCAAATTACGCACGTACCGGAGGGCAGG

TGACTGCAGGGAATGTGCAATCGATTATTGGCGTGACTTTTGTTTATCAA

TAA
```

In certain implementations, the primers shown in Table 4 may be used for amplification of the fimH in the assays described herein.

TABLE 4

| PRIMERS | | |
|---|---|---|
| fimH30 allele F | CCGCCAATGGTACCGCTATT | (SEQ ID NO: 1) |
| fimH30 allele R | TGGGGTGGCGATTAAAGCTG | (SEQ ID NO: 5) |
| NA11A ST131F | CCGCCAATGGTACCGCTATT | (SEQ ID NO: 1) |
| NA11A ST131R | TGGGGTGGCGAT | (SEQ ID NO: 6) |

TABLE 4-continued

PRIMERS

| | |
|---|---|
| fimH30F-19 | GCCAATGGTACCGCTATT (SEQ ID NO: 7) |
| fimH30F-17 | CAATGGTACCGCTATT (SEQ ID NO: 8) |
| fimH30R-24 | GAGCCAGCTTTAATCGCCACCCCA (SEQ ID NO: 9) |
| fimH30R-22 | GCCAGCTTTAATCGCCACCCCA (SEQ ID NO: 10) |

The above primers detect the fimH30 gene in whatever strain background it may occur, which could be H30-Rx or a different strain. It is to be appreciated, that typically the identified primers are combined and/or used with known methods that define and identify a strain as being ST131 (of which several are published), thereby specifically identifying the sub-clone as H30-Rx.

Example 11. FQ Resistance Assays

The following is a PCR Protocol for ST131 Subclone multiplex PCR, according to some embodiments. It is able to identify by broad definition the MLST ST131 type *E. coli* with the mdh36/gyr47 specific primers in addition to being able to positively identify the fimH30 subclone, or O16 (fimH41 associated) subclone.

Table 5 describes specific primers used in this assay. An example of the amplification products is shown in FIG. 10.

TABLE 5

| Primer | Primer sequence | SEQ ID NO: | Amplicon size |
|---|---|---|---|
| uidA for | GCGTCTGTTGACTGGCAGGTGGTGG | 11 | 508 bp |
| uidA rev | GTTGCCCGCTTCGAAACCAATGCCT | 12 | |
| gndbis.f (universal O type for) | ATACCGACGACGCCGATCTG | 13 | 450 np |
| O16 specific rev | GGATCATTTATGCTGGTACG | 14 | |
| fimH30For-21 | CCGCCAATGGTACCGCTATT | 1 | 354 bp |
| fimH30Rev-20 | CAGCTTTAATCGCCACCCCA | 2 | |
| mdh36_For Tm53 | TAACGTTAACGCCGGT | 15 | 275 bp |
| mdh36_rev Tm54 | GGTAACACCAGAGTGACCA | 16 | |
| gyrB47 For Tm58.6 | CGCGATAAGCGCGAC | 17 | 130 bp |
| gyrB47rev Tm60.5 | ACCGTCTTTTTCGGTGGAA | 18 | |

Figure 10:
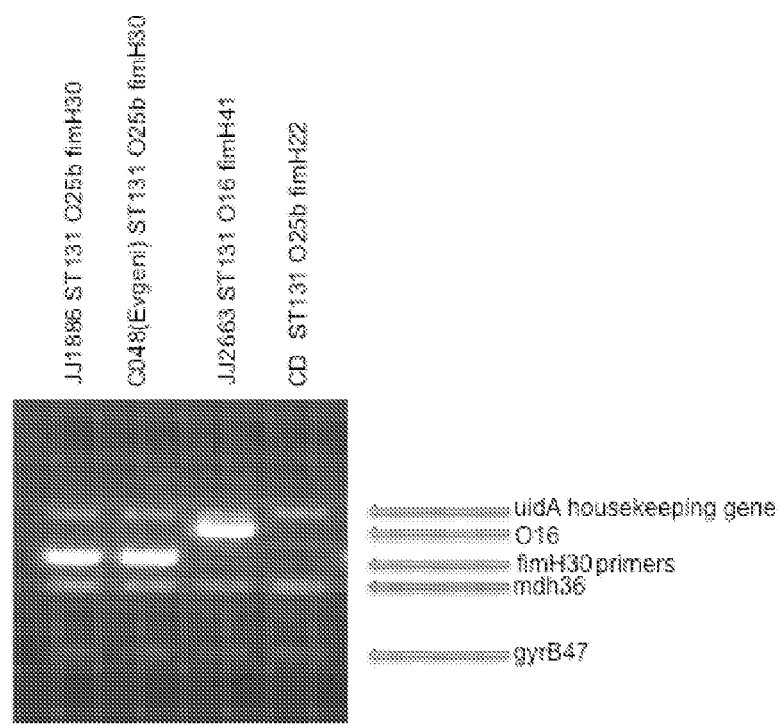
FIG. 10 shows sample results of an FQ resistance assay according to embodiments.

FIG. 10 presents sample results of an FQ resistance assay according to certain embodiments. The uidA band is a generic *E. coli* marker that is used for species confirmation and as an amplification control. The O16 band is for the O16 rfb (O lipopolysaccharide synthesis) variant, which corresponds with a different sub-clone within ST131. The fimH30 primers identify the H30 allele of fimH (as is present in H30-Rx). The mdh36 and gyrB47 bands identify specific alleles of mdh and gyrB that are present jointly only in ST131 and closely related strains. The combined presence of the fimH30 band and the mdh36 and gyrB47 bands identifies it as H30-Rx.

Tables 6 and 7 show PCR mixtures and protocols according to some embodiments. In some embodiments, a BIO-RAD MYCYCLER thermal cycler is used.

TABLE 6

| Master Mix | Volume per sample | Stock Conc. | Working Conc. |
|---|---|---|---|
| 10 × Buffer | 2.5 µl | 10X | 1X |
| MgCl$_2$ | 4.0 µl | 25 mM | 4 mM |
| dNTPs (2.5 mM each) | 2.0 µl | 10 mM | 0.8 mM |
| Amplitaq Gold | 0.25 µl | 5 U/uL | 1.25 U |

TABLE 7

| Cycles | degrees | time |
|---|---|---|
| 1 | 95 | 8 minutes |
| 30 | 94 | 20 sec |
| | 64 | 60 sec |
| 1 | 72 | 5 minutes |
| 1 | 4 | Forever |

In some embodiments, primers are added to have a final concentration of 0.6 uM. For example, in some embodiments, uid A internal control is made up to 0.06 uM so as to not overpower other bands. According to embodiments, 2.0 µL of a DNA sample prepared according to conventional methods is added. Water is added to a final volume of 25 uL. However, in some embodiments, the total volume may be scaled down by as much as 70% without loss of quality.

The samples shown in FIG. 10 were run on a 2% agarose gel at 225V for 55 minutes on a long OWL gel bed for sufficient separation of the O16 band from the uidA band.

Example 12. ST131 Genetic Markers

Tables 8-10 describe 19 sets of primers for genetic markers that are diagnostic for H30-Rx and other important ST131 lineages.

TABLE 8

Primers for genetic markers that are diagnostic for H30-Rx and other ST131 lineages

| Marker Name | Primer sequence | SEQ ID NO: | Product size (bp) | $T_m$ (° C.) |
|---|---|---|---|---|
| RMT12 | CGTGACCTGTCCGTTCATAAGTAGAG | 19 | 720 | 65.7 |
| ST131 | GCGATGGCGAAAACACTGTATGAC | 20 | | 66 |

TABLE 8-continued

Primers for genetic markers that are diagnostic for H30-Rx and other ST131 lineages

| Marker Name | Primer sequence | SEQ ID NO: | Product size (bp) | $T_m$ (° C.) |
|---|---|---|---|---|
| RMT1 H30 | TGGCCTTGTCAGACCTGCTAAC | 21 | 517 | 66.9 |
|  | GAGAGACTCATATCGCGCTCCA | 22 |  | 65.9 |
| O25bF | CTTTCCCATTGCATACGCTCATAG | 23 | 139 | 63.1 |
|  | CAGGTGCGTGTATAGGTAATGGT | 24 |  | 63.5 |
| Flag2Minus | AGGTTGATCGCCAGAATCATCA | 25 | 335 | 64.1 |
|  | AACCCACCACCGTTAAAAATCG | 26 |  | 63.7 |
| Falg2Plus | ATTCTTTGCTGGAATGCGTGC | 27 | 402 | 64.4 |
|  | AACCCACCACCGTTAAAAATCG | 28 |  | 63.7 |
| Flag2 JJ1886-like | GGCAGGTAAGTTTGACGATTTCT | 29 | 637 | 63.9 |
|  | CAGCGATGAATTTGTTTCTTTGTG | 30 |  | 62.6 |
| H4/17 FliC | CAGACGATCAGCATTGGCTTG | 31 | 344 | 63.7 |
|  | GCGGCATCCAGTGCTTTTAAC | 32 |  | 64.4 |
| fimB insertion | TCCTGACCCATAGTGAAATCG | 33 | 538/2428 | 60.7 |
|  | GCTCTATCCCAGATGCCGTA | 34 |  | 62.2 |
| papA F10 | GGCAGTGGTGTCTTTTGGTG | 35 | 312 | 64.4 |
|  | CTCCTCATTATGACCAGAAACCCT | 36 |  | 64.5 |
| PapG II | GGGATGAGCGGGCCTTTGAT | 37 | 190 | 66.8 |
|  | CGGGCCCCCAAGTAACTCG | 38 |  | 66.6 |
| GI2N | CAACATGCTTCCAGCACTCCT | 39 | 582 | 65.6 |
|  | CCCAGAATACGATAACGGAGACG | 40 |  | 66.3 |
| Nissle island | GTGAAACCGTACTGCGTGATGC | 41 | Variable (See Table 9) | 65.8 |
|  | GACCAGCATGTGGGAGACAATG | 42 | 0.5/3/4/7 kb | 65.2 |
| kps K5 | GTCGGTGATGCCAGGTTAAAGA | 43 | 1085 | 65 |
|  | CGCACCTCATGGACGATATGTT | 44 |  | 64.6 |
| kpsM JJ1886-like | GTCGGTGATGCCAGGTTAAAGA | 45 | 803 | 65 |
|  | CTTTCACCGATCATTCCCGACT | 46 |  | 64.3 |
| kpsM SE15-like | GTCGGTGATGCCAGGTTAAAGA | 47 | 560 | 65 |
|  | TTTCACATCGCTCATTTTCTGGA | 48 |  | 63.2 |
| kpsM NA114-like | GTCGGTGATGCCAGGTTAAAGA | 49 | 366 | 65 |
|  | TGGTGAAGACGCAGGTTAATGC | 50 |  | 65.2 |
| kps SE15 | CCGCAAGGTGAAGTGACATCAG | 51 | 189 | 64.9 |
|  | TGGGAGGGTATGCAGCTTGTT | 52 |  | 66.1 |
| papA F9 | GGCAGTGGTGTCTTTTGGTG | 53 | 416 | 64.4 |
|  | AAGGCCCCGTTGACGTTTT | 54 |  | 65.8 |
| O25aF | ATCCTATCTTTCCCAAATCGAAACA | 55 | 221 | 62.4 |
|  | CAGGTGCGTGTATAGGTAATGGT | 56 |  | 63.5 |

TABLE 9

Primers for genetic markers that are diagnostic for H30-Rx and other ST131 lineages

| Marker Name | Primer Sequence | SEQ ID NO: | Specificity/Target |
|---|---|---|---|
| RMT12 ST131 | CGTGACCTGTCCGTTCATAAGTAGAG | 19 | restriction modification system type 1 (specific for ST131) |
|  | GCGATGGCGAAAACACTGTATGAC | 20 | JJ1886, NA114, SE15 |
| RMT1 H30 | TGGCCTTGTCAGACCTGCTAAC | 21 | restriction modification system type 1 |
|  | GAGAGACTCATATCGCGCTCCA | 22 | fim H30-linked |
| O25bF | CTTTCCCATTGCATACGCTCATAG | 23 | targets O25b O-antigen polymerase and flanking sequence |
|  | CAGGTGCGTGTATAGGTAATGGT | 24 | JJ1886, EC958 |

TABLE 9-continued

Primers for genetic markers that are diagnostic for H30-Rx and other ST131 lineages

| Marker Name | Primer Sequence | SEQ ID NO: | Specificity/Target |
|---|---|---|---|
| Flag2 | AGGTTGATCGCCAGAATCATCA | 25 | targets sequences flanking Flag2 locus |
|  | AACCCACCACCGTTAAAAATCG | 26 | SE15 plus other Flag2-minus strains |
| Falg2Plus | ATTCTTTGCTGGAATGCGTGC | 27 | targets a junction of Flag2 locus and its flanking sequence |
|  | AACCCACCACCGTTAAAAATCG | 28 | JJ1886, NA114 plus some other Flag2-positive strains |
| Flag2 JJ1886-like | GGCAGGTAAGTTTGACGATTTCT | 29 | JJ1886-like insertion within Flag2 locus |
|  | CAGCGATGAATTTGTTTCTTTGTG | 30 |  |
| H4/17 FliC | CAGACGATCAGCATTGGCTTG | 31 | targets FliC gene flagellar types H4 and H17 |
|  | GCGGCATCCAGTGCTTTTAAC | 32 | they can be discriminated by a SNP in the sequences |
| fimB insertion | TCCTGACCCATAGTGAAATCG | 33 | fimB insertion primers from reference |
|  | GCTCTATCCCAGATGCCGTA | 34 | targets sequences flanking the insertion |
| papA F10 | GGCAGTGGTGTCTTTTGGTG | 35 | papA allele F10 |
|  | CTCCTCATTATGACCAGAAACCCT | 36 |  |
| PapG II | GGGATGAGCGGGCCTTTGAT | 37 | PapG II |
|  | CGGGCCCCAAGTAACTCG | 38 |  |
| GI2N | CAACATGCTTCCAGCACTCCT | 39 | Nissle island PI junction |
|  | CCCAGAATACGATAACGGAGACG | 40 | Abu, Nissle plus JJ1886 |
| Nissle island | GTGAAACCGTACTGCGTGATGC | 41 | primers target sat and hypothetical genes linking JJ1886 contigs |
|  | GACCAGCATGTGGGAGACAATG | 42 | C34 to C39; ABU size-3030 bp, CFT073-540 bp Nissle1917-4283 |
| kps K5 | GTCGGTGATGCCAGGTTAAAGA | 43 | k5 type capsule |
|  | CGCACCTCATGGACGATATGTT | 44 | ABU, Nissle |
| kpsM JJ1886-like | GTCGGTGATGCCAGGTTAAAGA | 45 | JJ1886-like kps |
|  | CTTTCACCGATCATTCCCGACT | 46 | targets kpsM flanking sequence |
| kpsM SE15-like | GTCGGTGATGCCAGGTTAAAGA | 47 | SE15-like kps |
|  | TTTCACATCGCTCATTTTCTGGA | 48 | targets kpsM flanking sequence |
| kpsM NA114-like | GTCGGTGATGCCAGGTTAAAGA | 49 | NA114-like kps |
|  | TGGTGAAGACGCAGGTTAATGC | 50 | targets kpsM flanking sequence |
| kps SE15 | CCGCAAGGTGAGTGACATCAG | 51 | SE15 kps region 2 |
|  | TGGGAGGGTATGCAGCTTGTT | 52 |  |
| papA F9 | GGCAGTGGTGTCTTTTGGTG | 53 | papA allele F9 |
|  | AAGGCCCCGTTGACGTTTT | 54 |  |
| O25aF | ATCCTATCTTTCCCAAATCGAAACA | 55 | targets O25a O-antigen polymerase and flanking sequence |
|  | CAGGTGCGTGTATAGGTAATGGT | 56 | ABU, ETEC E47a |

TABLE 10

Primers for genetic markers that are diagnostic for H30-Rx and other ST131 lineages

| | ST131 fimH group | | | | | | | | total ST131 | non-ST131 |
|---|---|---|---|---|---|---|---|---|---|---|
| | H0 | H15 | H22 | H27 | H30 | H35 | H41 | H94 | | |
| # clones-> | | | | | | | | | | |
| Marker name | 1 | 1 | 30 | 3 | 85 | 18 | 21 | 1 | 160 | 87 |
| RMTI2 ST131 | 1 | 0 | 27 | 3 | 80 | 16 | 21 | 1 | 149 | 0 |
| RMTI H30 | 1 | 0 | 0 | 0 | 85 | 0 | 0 | 0 | 86 | 7 |
| O25bF | 1 | 1 | 30 | 3 | 83 | 18 | 1 | 1 | 138 | |

TABLE 10-continued

Primers for genetic markers that are diagnostic for H30-Rx and other ST131 lineages

| | ST131 fimH group | | | | | | | | total ST131 | non-ST131 |
|---|---|---|---|---|---|---|---|---|---|---|
| | H0 | H15 | H22 | H27 | H30 | H35 | H41 | H94 | | |
| | | | | | # clones-> | | | | | |
| Marker name | 1 | 1 | 30 | 3 | 85 | 18 | 21 | 1 | 160 | 87 |
| Flag2Minus | 0 | 0 | 4 | 0 | 0 | 0 | 21 | 0 | 25 | |
| Falg2Plus | 1 | 1 | 26 | 3 | 85 | 18 | 0 | 1 | 135 | |
| Flag2 JJ1886-like | 0 | 1 | 26 | 3 | 75 | 18 | 0 | 1 | 124 | |
| H4/17 FliC | 1 | 1 | 30 | 3 | 85 | 17 | 1 | 1 | 139 | |
| fimB insertion | 1 | 0 | 0 | 0 | 84 | 0 | 0 | 0 | 85 | |
| papA F10 | 1 | 1 | 9 | 1 | 79 | 7 | 21 | 1 | 119 | |
| PapG II | 0 | 0 | 3 | 2 | 8 | 1 | 1 | 0 | 15 | |
| G12 N | 1 | 1 | 24 | 2 | 84 | 15 | 21 | 1 | 149 | |
| Nissle island | 1 | 1 | 10 | 0 | 80 | 7 | 18 | 1 | 118 | |
| | 3 kb | 3 kb | 3 kb | | 3 kb | 3 kb | 7 kb | 3 kb | | |
| kps K5 | 0 | 1 | 8 | 0 | 39 | 4 | 0 | 1 | 53 | |
| kpsM JJ1886-like | 0 | 0 | 0 | 0 | 5 | 3 | 0 | 0 | 8 | |
| kpsM SE15-like | 0 | 0 | 0 | 0 | 0 | 0 | 0 | 0 | 0 | |
| kpsM NA114-like | 0 | 0 | 0 | 0 | 0 | 0 | 0 | 0 | 0 | |
| kps SE15 | 0 | 0 | 0 | 0 | 0 | 0 | 0 | 0 | 0 | |
| papA F9 | 0 | 0 | 0 | 0 | 0 | 0 | 0 | 0 | 0 | |
| O25aF | 0 | 0 | 0 | 0 | 0 | 0 | 0 | 0 | 0 | |

Example 13. Experimental Methods

The following experimental methods were used for the analyses discussed in Examples 14-20.

Isolates and Patients

The molecular epidemiological analyses used a large collection (n=1,908) of recent, consecutive, single-patient *E. coli* isolates from 6 clinical microbiology laboratories in the U.S. and Germany. The U.S. isolates (n=1,518) were recovered in 2010-2011 from 5 locations, including Group Health Cooperative, Harborview Medical Center, Seattle Children's Hospital, and University of Washington Medical Center (all in Seattle, Wash.), and the Veterans Affairs Medical Center in Minneapolis, Minn., as described previously (Johnson, J. R., V. Tchesnokova, B. Johnston, C. Clabots, P. L. Roberts, M. Billig, K. Riddell, P. Rogers, X. Qin, S. Butler-Wu, L. B. Price, M. Aziz, M. H. Nicolas-Chanoine, C. Debroy, A. Robicsek, G. Hansen, C. Urban, J. Platell, D. Trott, G. Zhanel, S. J. Weissman, B. T. Cookson, F. C. Fang, A. Limaye, D. Scholes, S. Chattopadhyay, D. C. Hooper, and E. V. Sokurenko. 2013. Abrupt emergence of a single dominant multi-drug-resistant strain of *Escherichia coli*. J Infect Dis.). The German isolates (n=390) were recovered in 2012 at the University Hospital in Muenster, Germany. All isolates underwent fumC-fimH (CH) clonotyping (Weissman, S. J., J. R. Johnson, V. Tchesnokova, M. Billig, D. Dykhuizen, K. Riddell, P. Rogers, X. Qin, S. Butler-Wu, B. T. Cookson, F. C. Fang, D. Scholes, S. Chattopadhyay, and E. Sokurenko. 2012. High-resolution two-locus clonal typing of extraintestinal pathogenic *Escherichia coli*. Appl Environ Microbiol 78:1353-60.) to identify ST131 and its constituent CH clonotypes (i.e., fimH-specific subclones, including H30), and were assessed for ESBL production by disk diffusion as specified by the Clinical and Laboratory Standards Institute. Medical record data regarding presence of clinically diagnosed sepsis at the time of sample collection or during the subsequent 30 days were available for 1,133 (75%) of the 2010-2011 U.S. isolates. Each center's institutional review board approved the study protocol.

Pulsed-Gel Electrophoresis Analysis

The 524 historical and recent ST131 isolates were subjected to standardized XbaI PFGE analysis, as described previously (Johnson, J. R., M. H. Nicolas-Chanoine, C. DebRoy, M. Castanheira, A. Robicsek, G. Hansen, S. Weissman, C. Urban, J. Platell, D. Trott, G. Zhanel, C. Clabots, B. D. Johnston, and M. A. Kuskowski. 2012. Comparison of *Escherichia coli* ST131 pulsotypes, by epidemiologic traits, 1967-2009. Emerg Infect Dis 18:598-607.). The dendrogram was inferred within BioNumerics (Applied Maths) according to the unweighted pair group method based on Dice similarity coefficients.

Strain Selection

Figure 11:
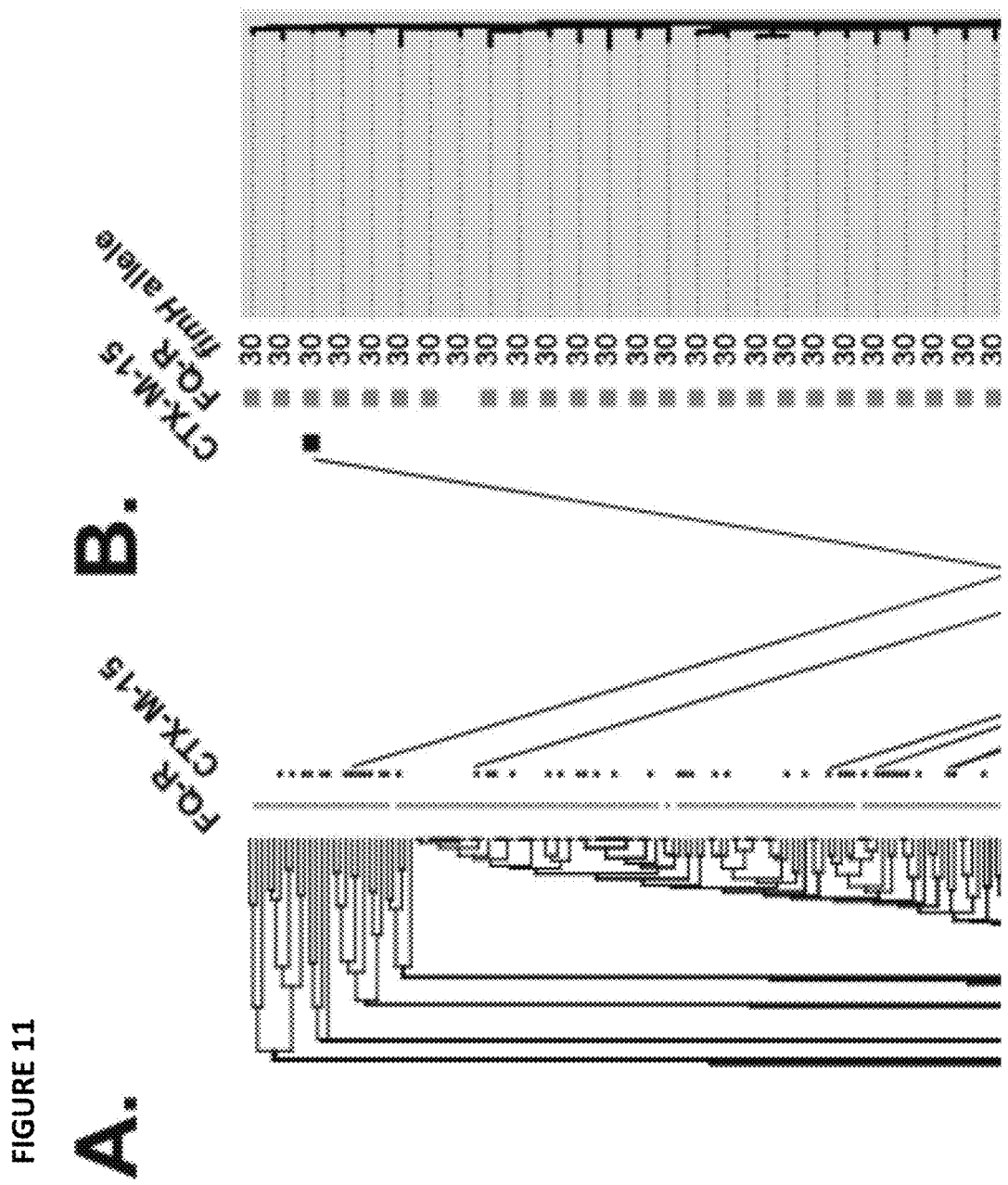
FIG. 11 shows a pulsed-field gel electrophoresis (PFGE)- and whole genome SNP-based phylogeny of Escherichia coli ST131.

Selection of ST131 isolates for genome sequencing was done in successive phases. First, to sample the breadth of phylogenetic diversity within the ST (as reflected in PFGE profiles), 20 isolates were selected to represent widely distributed clusters within a PFGE profile dendrogram based on a published collection of 524 historical and recent ST131 isolates from diverse locales, years of isolation, and hosts (FIG. 11A). In selecting the representative isolate(s) for a given PFGE cluster, priority was given to (i) most recent year of isolation, (ii) human host, and (iii) fluoroquinolone resistance. Next, 28 additional isolates were selected from these same PFGE clusters based on (i) proximity in the dendrogram to the initially selected (index) isolate plus (ii) differences from the index isolate with respect to host and/or fluoroquinolone phenotype. Subsequently, an additional 60 isolates were selected from both this initial collection and a large collection of recent human clinical ST131 isolates from Seattle, Wash., and Minneapolis, Minn., that had undergone sequence analysis of gyrA, parC, and fimH (to define subclones within ST131), plus PFGE analysis. Here, selection criteria included (i) distinctive gyrA, parC, and/or fimH alleles, or combinations thereof; (ii) outliers with respect to fluoroquinolone phenotype, in comparison with other isolates sharing the same PFGE type or gyrA/parC/fimH allele combination; and (iii) distinctive host species, clinical presentations (e.g., published case report isolates), specimen types (e.g., food or environmental), or dates of isolation (e.g., oldest known and oldest published ST131 isolates). Of the 108 total selected isolates, four isolates were subsequently excluded due to questionable authenticity, leaving 104 isolates for genome sequencing.

Genome Sequencing

DNA samples were prepared for multiplexed, paired-end sequencing on an Illumina Genome Analyzer IIx (Illumina, Inc., San Diego, Calif.). For each isolate, 1 to 5 µg DNA in 200 µl was sheared in a 96-well plate with the SonicMAN (part no. SCM1000-3; Matrical BioScience, Spokane, Wash.) to a size range of 200 to 1,000 bp, with the majority of material at ca. 600 bp, using the following parameters: pre-chill, 0° C. for 75 s; cycles, 20; sonication, 10 s; power, 100%; lid chill, 0° C. for 75 s; plate chill, 0° C. for 10 s; post-chill, 0° C. for 75 s. The sheared DNA was purified using the QIAquick PCR Purification kit (catalog no. 28106; Qiagen, Valencia, Calif.). The enzymatic processing (end repair, phosphorylation, A tailing, and adaptor ligation) of the DNA followed the guidelines described in the Illumina protocol (Preparing Samples for Multiplexed Paired-End Sequencing, catalog no. PE-930-1002, part no. 1005361). The enzymes for processing were obtained from New England Biolabs (catalog no. E6000L; New England BioLabs, Ipswich, Mass.), and the oligonucleotides and adaptors were obtained from Illumina (catalog no. PE-400-1001).

After ligation of the adaptors, the DNA was run on a 2% agarose gel for 2 h, after which a gel slice containing 500- to 600-bp fragments of each DNA sample was isolated and purified using the QIAquick Gel Extraction kit (catalog no. 28706; Qiagen, Valencia, Calif.). Individual libraries were quantified by quantitative PCR on an ABI 7900HT (part no. 4329001; Life Technologies Corporation, Carlsbad, Calif.) in triplicate at two concentrations, 1:1,000 and 1:2,000, using the Kapa Library Quantification kit (part no. KK4832 or KK4835; Kapa Biosystems, Woburn, Mass.). Based on the individual library concentrations, equimolar pools of no more than 12 indexed E. coli libraries were prepared at a concentration of at least 1 nM using 10 mM Tris-HCl (pH 8.0)-0.05% Tween 20. To ensure accurate loading onto the flow cell, the same quantification method was used to quantify the final pools. The pooled paired-end libraries were sequenced on an Illumina Genome Analyzer IIx to a read length of at least 76 bp.

Identification of SNPs

Illumina WGS data sets were aligned against the chromosome of a published ST131 reference genome (strain NA114; GenBank accession no. CP002797) (Avasthi, T. S., N. Kumar, R. Baddam, A. Hussain, N. Nandanwar, S. Jadhav, and N. Ahmed. 2011. Genome of multidrug-resistant uropathogenic Escherichia coli strain NA114 from India. J Bacteriol 193:4272-3.) using the short-read alignment component of the Burrows-Wheeler Aligner. Each alignment was analyzed for SNPs using SolSNP (http://sourceforge.net/projects/solsnp/). To avoid false calls due to sequencing errors, SNP loci were excluded if they did not meet a minimum coverage of 10× and if the variant was present in less than 90% of the base calls for that position. SNP calls were combined for all of the sequenced genomes such that, for the locus to be included in the final SNP matrix, it had to be present in all of the genomes. SNPs falling in the duplicated regions on the reference genome were discarded.

Phylogenetic Analysis

Phylogenetic trees were generated using the maximum-parsimony method in PAUP v4.0b10. Using prior knowledge about near neighbors a published E. coli strain belonging to the phylogenetic group B2 genome (strain AA86; GenBank accession no. AFET00000000) was selected as an outgroup to root the ST131 WGST tree (Yi, H., Y. J. Cho, H. G. Hur, and J. Chun. 2011. Genome sequence of Escherichia coli AA86, isolated from cow feces. J Bacteriol 193:3681.). ST131 isolates in the clade nearest to this bifurcation point were used to root subsequent trees.

Detection of H30-Rx-Specific SNPs

The two SNPs that differentiate the CTX-M-15-associated subclone (H30-Rx) within the H30-R subclone from rest of the H30 subclone were detected using Sanger sequencing. SNP-200 was detected as a c-to-t transition at position 299 of the 460-bp PCR product generated using forward primer 5'-GACACCATGCGTTTTGCTTC-3' (SEQ ID NO: 57) and reverse primer 5'-TCGTACCG-GCAACAATTGAC-3' (SEQ ID NO: 58). SNP-264 was detected as g-to-a transition at position 287 of the 462-bp PCR product generated using forward primer 5'-GTGGC-GATTTCACGCTGTTA-3' (SEQ ID NO: 59) and reverse primer 5'-TATCCAGCACGTTCCAGGTG-3' (SEQ ID NO: 60). Isolates that tested positive for both SNPs were regarded as members of the H30-Rx subclone.

These primers were also used to survey 54 non-ST131 strains for the presence of SNP-200 and SNP-264. Only in one was SNP-264 found, but not SNP-200. The particular non-ST131 strain with SNP-264 was a very different and rare sequence type and was ESBL positive.

Detection of Bla$_{CTX-M-15}$

The CTX-M-15-encoding gene bla$_{CTX-M-15}$ was detected by PCR using SNP-specific forward primer 5'-ATAAAAC-CGGCAGCGGTGG-3' (SEQ ID NO: 61) and universal reverse primer 5'-GAATTTTGACGATCGGGG-3' (SEQ ID NO: 62) (Johnson, J. R., C. Urban, S. J. Weissman, J. H. Jorgensen, J. S. Lewis, 2nd, G. Hansen, P. H. Edelstein, A. Robicsek, T. Cleary, J. Adachi, D. Paterson, J. Quinn, N. D. Hanson, B. D. Johnston, C. Clabots, and M. A. Kuskowski. 2012. Molecular epidemiological analysis of Escherichia coli sequence type ST131 (O25:H4) and blaCTX-M-15 among extended-spectrum-beta-lactamase-producing E. coli from the United States, 2000 to 2009. Antimicrob Agents Chemother 56:2364-70.). PCR conditions were: 2 min denaturation at 95° C., then 30 cycles of 30 sec at 94° C., 30 sec at 63° C., and 1 min at 68° C., followed by 7 min at 72° C. elongation. The bla$_{CTX-M-15}$-specific 483-bp PCR product was detected by agarose gel electrophoresis.

fimH Identification

The presence of specific fimH alleles was assessed in all 106 ST131 isolates. 105 isolates were assembled using VelvetOptimiser (Version 2.2.2) and Velvet (Zerbino, D. R., and E. Birney. 2008. Velvet: algorithms for de novo short read assembly using de Bruijn graphs. Genome Res 18:821-9.). An in-house list of fimH genes was compared against each of the assembled genomes and NA114 using Nucleotide-Nucleotide BLAST (Version 2.2.25+). Sequence similarity matches of genes were determined using thresholds of 100% nucleotide identity, 100% coverage of the query sequence length. fimH allele designations were assigned based on an in-house nomenclature.

Virulence Gene Profiling

All isolates were screened by PCR for a panel of 52 virulence genes as described previously (Johnson, J. R., B. Johnston, C. Clabots, M. A. Kuskowski, and M. Castanheira. 2010. Escherichia coli sequence type ST131 as the major cause of serious multidrug-resistant E. coli infections in the United States. Clin Infect Dis 51:286-94.), including: kii (kpsM II subset), kpsM II, K5, fyuA, fimH, usp, malX, ompT, O25b rfb, iutA, traT, sat, iha, sfa/focDE, G allele I, sfaS, focG, bmaE, F17, clpG, pic, vat, kpsM III, rfc, H7, clbB, clbN, afaE8, gafD, K15, astA, ireA, cdtB, papG allele III, papG II-III, papEF, papC, papAH, cnf1, hlyD, papG allele II, hra, iroN, hlyF, iss, cvaC, K1, tsh, K2, O16 rfb, afa/draBC, and ibeA. The uidA gene was included as a control.

gyA/parC Haplotyping

The presence of specific gyrA and parC alleles was assessed in all 106 ST131 isolates. 105 isolate were assembled using VelvetOptimiser (Version 2.2.2) and Velvet (Zerbino, D. R., and E. Bimey. 2008. Velvet: algorithms for de novo short read assembly using de Bruijn graphs. Genome Res 18:821-9.). An in-house list of gyrA and parC genes was compared against each of the assembled genomes and NA114 using Nucleotide-Nucleotide BLAST (Version 2.2.25+). Sequence similarity matches of genes were determined using thresholds of 100% nucleotide identity, 100% coverage of the query sequence length. gyrA/parC haplotypes were assigned based on an in-house nomenclature.

Statistical Methods

Comparisons of proportions were tested using Fisher's exact test or a chi square test (two-tailed), with $P<0.05$ as the criterion for significance.

Example 14. PFGE-Based Phylogenetic Analysis

Analysis of 524 ST131 isolates using PFGE revealed a complex phylogeny where isolates that were fluoroquinolone resistant and/or blaCTX-M-15-positive were intermingled with those that were fluoroquinolone susceptible and/or blaCTX-M-15-negative (FIG. 11A). As such, the PFGE phylogeny affirmed previous reports suggesting frequent horizontal acquisition of blaCTX-M-15 and fluoroquinolone resistance determinants among ST131 subclones.

Example 15. Whole Genome Sequencing

The genomes of 105 E. coli ST131 isolates from five countries, including 23 states and provinces in Canada and the U.S., were sequenced using a multiplexed paired-end sequencing approach on the Illumina GAIIx. The collection comprised isolates cultured from humans and animals between 1967 and 2011, and included a collection of CTX-M-15-producing isolates chosen for their diverse genetic backgrounds based on a PFGE phylogeny of over 500 isolates (FIG. 11A). The genomes were sequenced at an average depth of 60.93× (SD=31.66, using the 4,971,461-base NA114 chromosome as a reference). An average of 4,654,457.54 bases (SD=385629.23) were sequenced at ≥10× coverage.

Example 16. Whole-Genome SNP-Based Phylogenetic Analyses

Figure 25:
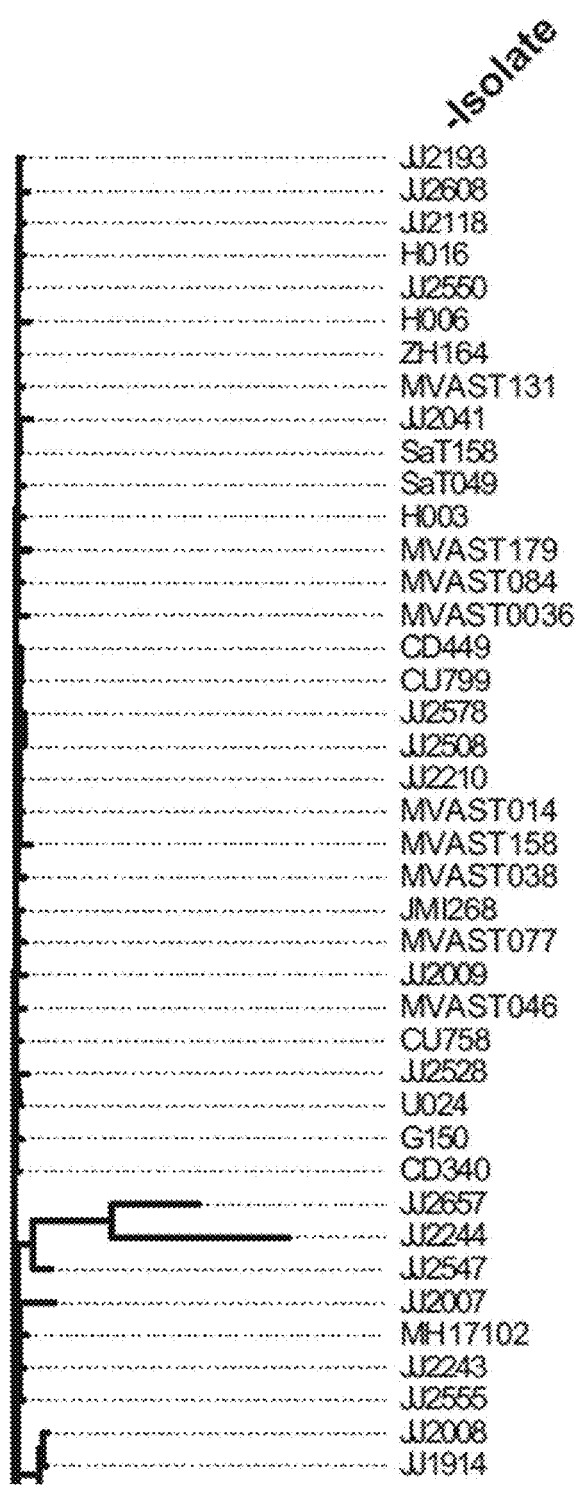
FIG. 25 shows a whole genome SNP-based phylogeny of *Escherichia coli* ST131, including strain AA86 as an outgroup. Phylogeny is based on 4,780 parsimony-informative and 15,978 total SNPs from throughout the genome. Homoplasy Index (HI)=0.351.

Genomic comparisons allowed the identification of SNP loci present in all isolates that could be used for phylogenetic reconstruction. The first phylogenetic tree included strain AA86 (group B2; ST1876) (Yi, H., Y. J. Cho, H. G. Hur, and J. Chun. 2011. Genome sequence of Escherichia coli AA86, isolated from cow feces. J Bacteriol 193:3681) as an outgroup to root the tree and to identify the basal clones within the ST131 phylogeny (FIG. 24). Next, strain AA86 was excluded from comparisons and a new SNP matrix and phylogenetic tree were generated (FIG. 25). Since (distant) strain AA86 lacks some of the genomic regions found within the ST131 clone, exclusion of AA86 increased the number of shared genomic regions in the sequence alignment and the number of SNPs with which to resolve the ST131 phylogeny.

The homoplasy index (HI) for these two initial trees (FIGS. 25 and 26) was exceedingly high (>0.33), indicating substantial recombination. Phylogenetic reconstruction that includes genomic regions that were acquired by horizontal gene transfer will not accurately represent the evolutionary history of clonal organisms. However, the phylogeny can be used to identify the regions acquired horizontally. This was accomplished here by mapping the HI values for individual SNPs to the reference genome, which revealed four large recombinant regions representing nearly 31% percent of the genome.

Figure 26:
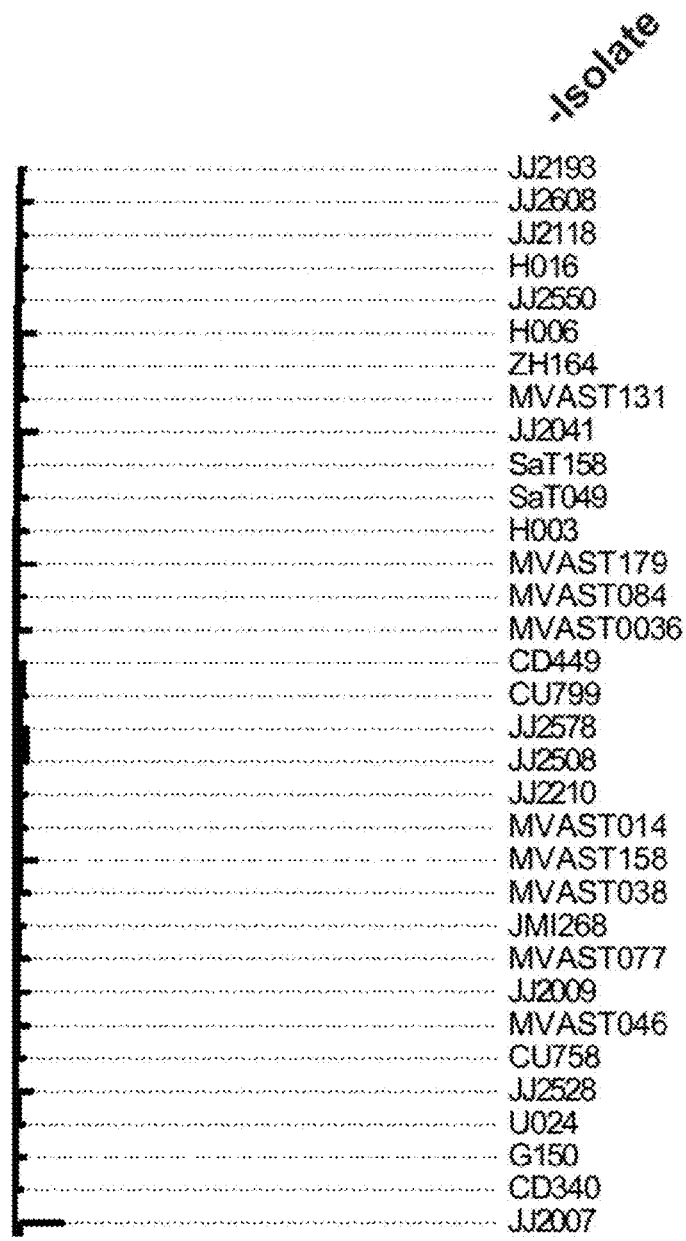
FIG. 26 shows a whole genome SNP-based phylogeny of *Escherichia coli* ST131, excluding strain AA86. Phylogeny is based on 4,770 parsimony-informative and 8,007 total SNPs from throughout the genome. HI=0.328.
Figure 28:
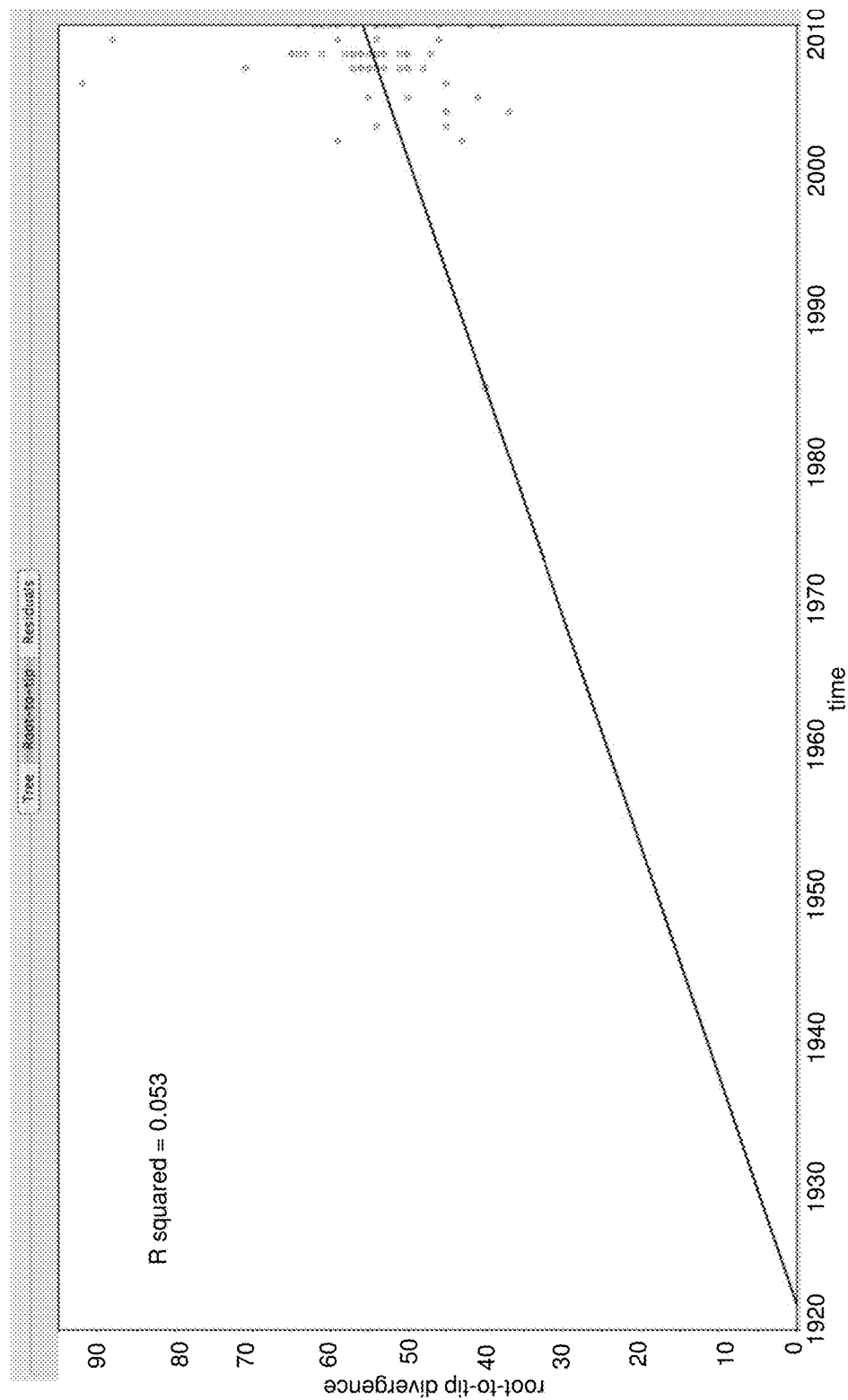
FIG. 28 shows a root-to-tip analysis. The root-to-tip analysis revealed no significant temporal information.
Figure 29:
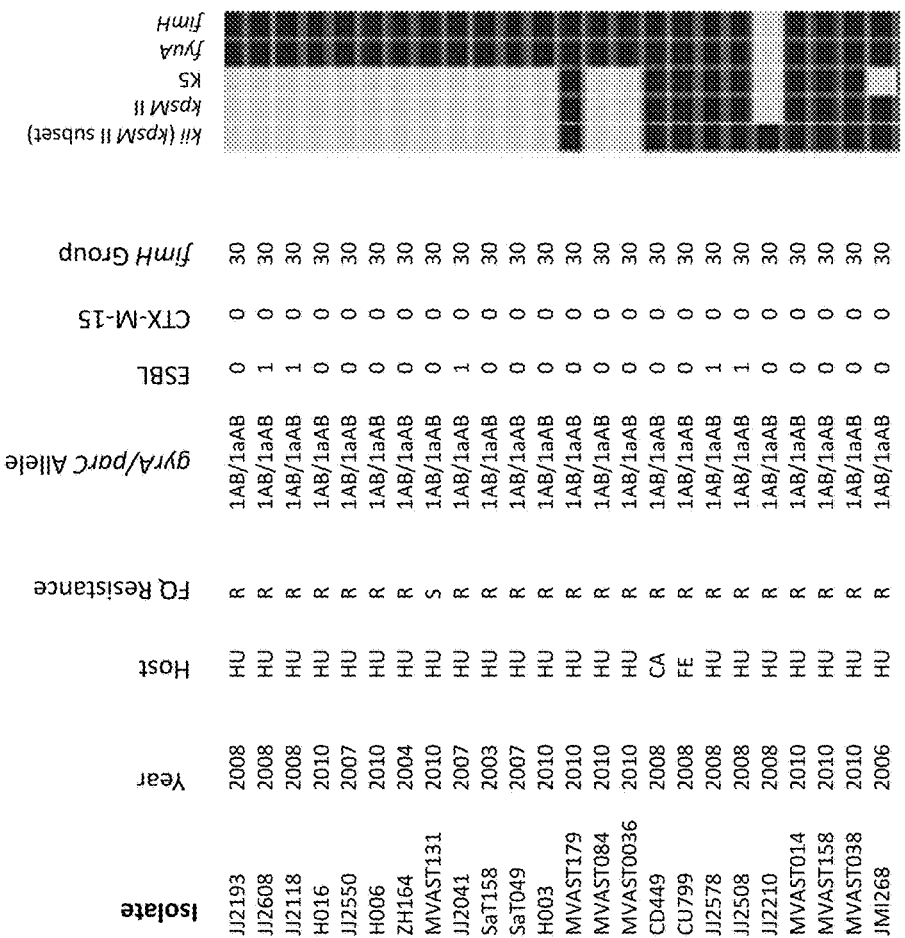
FIG. 29 shows the distribution of virulence factors by subclone. Presence (black box)/absence (gray box) scores for 52 known virulence factors are grouped by hierarchical clustering adjacent to the whole genome SNP-based phylogeny to reveal clonal grouping of these genes.

Excluding SNPs from the four horizontally acquired regions resulted in trees with minimal homoplasy (HI=0.012) (FIG. 11B; FIG. 26), suggestive of highly accurate phylogenies (Pearson, T., R. T. Okinaka, J. T. Foster, and P. Keim. 2009. Phylogenetic understanding of clonal populations in an era of whole genome sequencing. Infect Genet Evol 9:1010-9). FIG. 11B shows the whole genome SNP phylogeny for the 105 ST131 isolates plus the NA114 reference ST131 genome (Avasthi, T. S., N. Kumar, R. Baddam, A. Hussain, N. Nandanwar, S. Jadhav, and N. Ahmed. 2011. Genome of multidrug-resistant uropathogenic Escherichia coli strain NA114 from India. J Bacteriol 193: 4272-3). In this phylogeny there is distinct clustering of gyrA and parC alleles; fluoroquinolone resistance; ESBL and CTX-M-15 production; fimH alleles; and O type (FIG. 29 and Table 11A). This whole genome SNP tree includes the H30 subclone, which accounts for the emergence of the fimH30 allele within ST131 and has as its main constituent the H30-R subclone, which is the predominant fluoroquinolone-resistant and CTX-M-15-positive subclone within ST131. Strikingly, nearly all of the CTX-M-15-producing isolates in the 524-isolate source collection, which appeared to have diverse genetic backgrounds according to the PFGE-based phylogeny (FIG. 11A), collapsed into a single subclone within the whole genome SNP-based tree (FIG. 11B).

Figure 12:
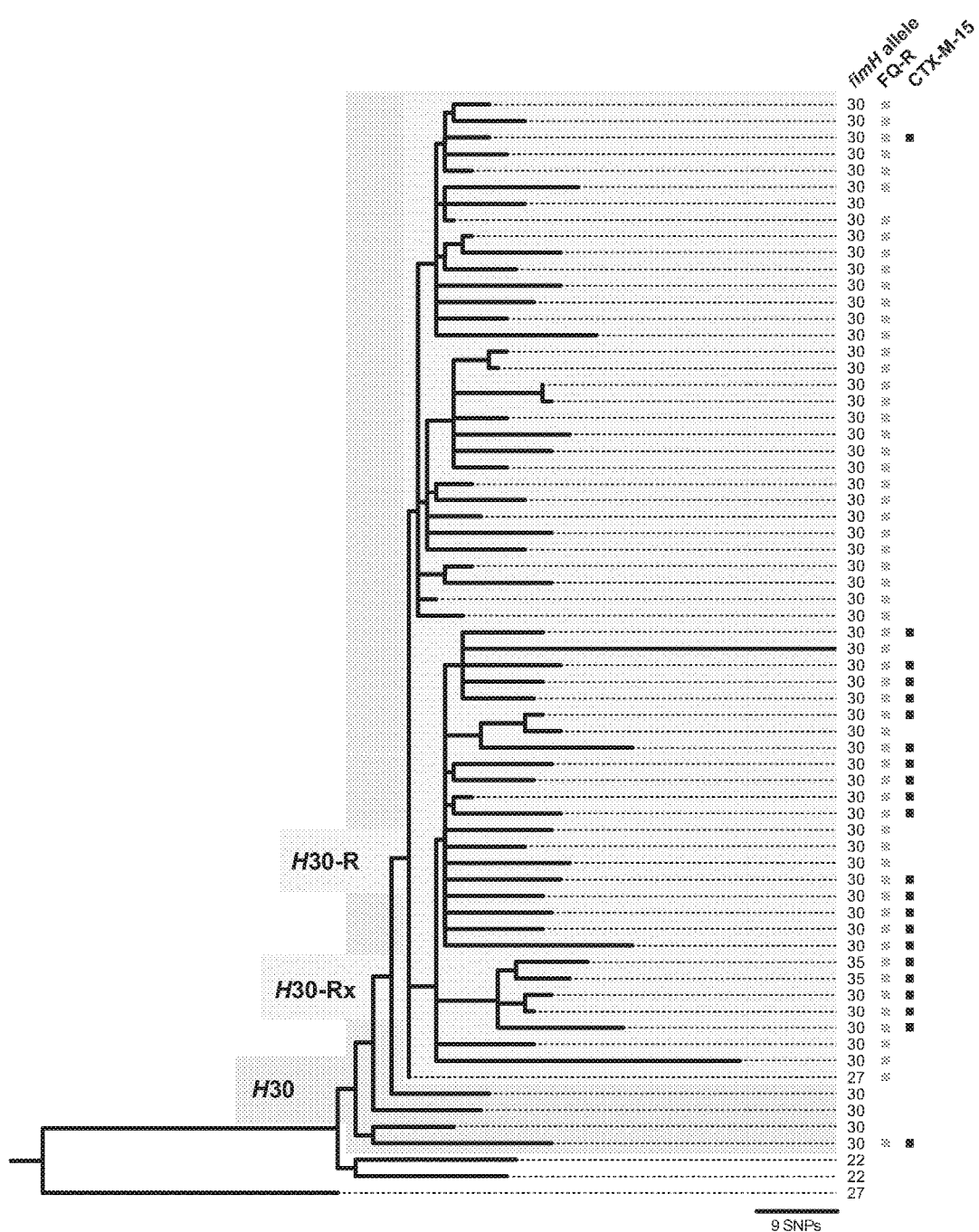
FIG. 12 shows a high-resolution phylogenetic analysis of the emergence of fluoroquinolone resistance and CTX-M-15 production.

To further resolve the evolutionary history of the H30-R subclone, genomic sequences from the H30-R isolates and their nearest neighbors were analyzed separately from the remaining ST131 isolates (FIG. 12). Alignment of these sequences to the finished NA114 reference genome increased the number of shared nucleotides and revealed additional SNPs that were used to generate the high-resolution and highly accurate (HI=0.000) phylogenetic tree shown in FIG. 12. This tree suggests that acquisition of the fimH30 allele likely preceded the acquisition of fluoroquinolone resistance in ST131. In stark contrast to the PFGE phylogeny (FIG. 11A), the whole genome-SNP-based phylogeny also suggests that 90% of the isolates carrying blaCTX-M-15—including isolates from Australia, Korea, Portugal, Canada and the U.S.—formed a distinct subclone, here provisionally labeled H30-Rx, that was derived from a single-common ancestor (FIG. 12).

TABLE 11A

Consensus characteristics of the major subclones within the all-ST131 phylogeny.

| Position in tree | FQ[a] | gyrA/parC alleles | ESBL[b] | bla$_{CTX-M-15}$[c] | predominant fimH allele (minor alleles) | O type |
|---|---|---|---|---|---|---|
| basal | S | 1A/1b | 0/1 | 0 | 41 | 16 |
| intermediate | S | 1/2b | 0 | 0 | 22 (35) | 25b |

TABLE 11A-continued

Consensus characteristics of the major subclones within the all-ST131 phylogeny.

| Position in tree | FQ[a] | gyrA/parC alleles | ESBL[b] | bla$_{CTX-M-15}$[c] | predominant fimH allele (minor alleles) | O type |
|---|---|---|---|---|---|---|
| intermediate | S | 1/1 | 0 | 0 | 22 (13, 30, 31, 35, 94) | 25b |
| most-derived | R | 1AB/1aAB | 0/1 | 0/1 | 30 (22, 27, 35) | 25b |

[a]FQ, fluoroquinolone phenotype; S, susceptible; R, resistant
[b]ESBL, extended-spectrum beta-lactamase production; 0, absent; 1, present
[c]0, absent; 1, present

Example 17. Extended Virulence Gene Profiles

All isolates were screened for 52 known virulence factors. While some phylogenetic clustering was observed, there were no significant differences between the H30-Rx and the H30-R isolates (FIG. 27).

FIG. 27 presents a distribution of virulence factors by subclone. Presence (black box)/absence (gray box) scores for 52 known virulence factors are grouped by hierarchical clustering adjacent to the whole genome SNP-based phylogeny to reveal clonal grouping of these genes. Virulence factors include: kii (kpsM II subset), kpsM II, K5, fyuA, fimH, usp, malX ompT, O25b rb, iutA, traT, sat, iha, sfa/focDE, G allele I, sfaS, focG, bmaE, F17, clpG, pic, vat, kpsM III, rfc, H7, clbB, clbN, afaE8, gaD, K15, astA, ireA, cdtB, papG allele III, papG II-III, papEF, papC, papAH, cnf1, hlyD, papG allele II, hra, iroN, hlyF, iss, cvaC, K1, tsh, K2, O16 rfb, afa/draBC, and ibeA. The uidA gene is included as a control. Other key metadata are presented in columns adjacent to the phylogeny. Host: Avian, AV; CA, canine; DO, dolphin; FE, feline; HU, human; MO, monkey. The significant phylogenetic clustering of most gyrA, parC, and fimH alleles (in text columns), and the O25b vs. O16 rib variants (presence/absence grid), indicate that these traits are inherited primarily vertically within ST131's several subclones, supporting their utility as clonal markers. Notable exceptions included the fimH35 allele and two of the (rare) FQ resistance-associated gyrA/parC allele combinations other 1AB/1aAB; these occurred sporadically, in multiple clades, indicating extensive horizontal gene transfer. The distant clade, characterized by fimH41 and the O16 rfb variant, likely accounts for the (atypical) serogroup O16 ST131 isolates identified in multiple studies. Such isolates are typically FQ-susceptible but often TMP-SMZ-resistant and occasionally ESBL-positive.

Example 18. Molecular Clock

Analysis using the Path-O-Gen tool indicated the presence of insufficient temporal signal to estimate reliably when the H30-R or H30-Rx subclones emerged (FIG. 29) (Rambaut, A. 2010, posting date. Patho-O-Gen v1.3. [Online.]).

Example 19. Association of ESBL Production and BlaCTX-M-15 with the H30-Rx Subclone To assess the generalizability of the observed association of ESBL production and blaCTX-M-15 with the H30-Rx subclone, 261 ST131 isolates identified among 1,908 single-patient recent clinical isolates from Seattle, Wash., Minneapolis, Minn., and Muenster, Germany were assessed for fimH type, H30-Rx subclone membership, ESBL production, and blaCTX-M-15 status (Table 11B). ESBL production and blaCTX-M-15 were moderately prevalent among the ST131 isolates overall (18% and 15%, respectively), but within ST131 were significantly concentrated within the H30-R subclone (25% and 20% prevalence, respectively), as compared with other ST131 isolates (3.4% prevalence for both traits). Moreover, the high prevalence of ESBL production and blaCTX-M-15 among H30-R isolates was due almost entirely to the H30-Rx subclone, which had an extremely high prevalence of both traits (75% and 77%), whereas non-H30-Rx H30-R isolates had a low prevalence of both traits (8% and 1.5%, respectively), similar to the values observed among non-H30-R ST131 isolates (3.4% for both traits) (Table 11B).

TABLE 11B

Prevalence of ESBL production and bla$_{CTX-M-15}$ in relation to major ST131 subclones.

| | No. of isolates | | |
|---|---|---|---|
| Subclones | Total | ESBL-pos. (% of total) | bla$_{CTX-M-15}$-pos. (% of total) |
| All ST131 | 261 | 47 (18) | 38 (15) |
| H30 | 174 | 44 (25)[a] | 35 (20)[e] |
| H30-Rx | 44 | 34 (77)[b, c] | 33 (75)[f, g] |
| H30 non-hr30-Rx | 130 | 10 (8)[b, d] | 2 (1.5)[f, h] |
| other sT131 subclones | 87 | 3 (3.4)[a, c, d] | 3 (3.4)[e, g, h] |

[a, b, c, e, f, g]p < 0.001;
[d, h]p > 0.10

For a sensitivity analysis regarding the association of the H30-R subclone with ESBL production and blaCTX-M-15, the 174 H30-R isolates among the recent U.S. and German clinical isolates were stratified by geography and year (i.e., Germany, 2012, vs. the U.S., 2010-2011) and, within the U.S., by clinical setting (urine isolates from ambulatory patients at GroupHealth, Seattle, vs. hospital laboratory isolates in Seattle and Minneapolis) (Table 12). Several trends emerged from this analysis. First, the prevalence of ESBL production, blaCTX-M-15, and the H30-Rx subclone varied greatly by epidemiologic group, being highest among the 2012 German isolates and lowest among the 2010-2011 GroupHealth isolates. Second, within each epidemiologic group the prevalence of ESBL production and blaCTX-M-15 was significantly greater among H30-Rx subclone isolates (50%-94% and 50%-84%, respectively) than non-H30-Rx isolates (0%-41% and 0%-12%, respectively). Third, regardless of setting, CTX-M-15 accounted for nearly all ESBL-positive isolates within the H30-Rx subclone, with non-CTX-M-15 ESBLs occurring almost exclusively (11/14, 79%) among non-H30-Rx isolates.

TABLE 12

Prevalence of the H30-Rx subclone, ESBL production, and bla$_{CTX-M-15}$, by clinical subgroup, within H30-R.

| Locale (years) | Total no. of isolates | ESBL-pos., bla$_{CTX-M-15}$-pos., and H30-Rx isolates, no. (% of total) | | | Proportion (%) of isolates ESBL-pos., by H30-Rx clade | | P value, f non-H30-Rx vs. non-H30-Rx | Proportion (%) of isolates bla$_{CTX-M-15}$-pos., by H30-Rx status | | P value H30-Rx vs. non-H30-Rx |
|---|---|---|---|---|---|---|---|---|---|---|
| | | SBL-pos. | bla$_{CTX-M-15}$-pos. | H30-Rx | If H30-Rx | H30-Rx | | If H30-Rx | If non-H30-Rx | |
| Germany (2012) | 35 | 24 (69%) | 19 (54%) | 18 (51%) | 17/18 (94%) | 7/17 (41%) | 0.001 | 17/18 (84%) | 2/17 (12%) | <0.001 |
| U.S. (2010-2011) | 139 | 20 (14%) | 16 (11.5%) | 26 (19%) | 17/26 (65%) | 3/113 (3%) | 0.001 | 16/26 (61%) | 0/113 (0%) | <0.001 |
| U.S.— Group Health | 51 | 3 (5.9%) | 3 (5.9%) | 6 (12%) | 3/6 (50%) | 0/45 (0%) | .001 | 3/6 (50%) | 0/45 (0%) | 0.001 |
| U.S.—non Group Health | 88 | 17 (19%) | 13 (14.8%) | 20 (23%) | 14/20 (70%) | 3/68 (4%) | 0.001 | 13/20 (65%) | 0/68 (0%) | <0.001 |

Example 20. Association of Clinical Sepsis with the H30-Rx Subclone

Data regarding presence/absence of clinically diagnosed sepsis were available for 1,133 (75%) of the recent U.S. clinical isolates, for comparison with clonal background (Table 13). Sepsis was diagnosed for 5.2% of the isolates overall, and approximately twice as commonly in association with H30-R (9%) as with other subclones (4.8%), a marginally significant difference (P=0.043). However, an impressive 28% of the H30-Rx subclone isolates were associated with sepsis, as compared with only 5.7% of non-H30-Rx H30-R isolates (hazard ratio 4.9; P=0.012), which was similar to that of non-H30-R isolates, ST131 and non-ST131 combined (4.8% P>0.10) (Table 13). Thus, the association of H30-R with sepsis was attributable entirely to the H30-Rx subclone within H30-R.

TABLE 13

Correlation between sepsis and the H30-Rx subclone among 1,133 U.S. clinical *E. coli* isolates (2010-2011).

| | Total no. of isolates | Sepsis-associated isolates, no. (%) |
|---|---|---|
| All isolates | 1,133 | 59 (5.2) |
| H30 | 106 | 10 (9)[a] |
| H30-Rx | 18 | 5 (28)[b, c] |
| H30 non-H30-Rx | 88 | 5 (5.7)[b, d] |
| All other subclones | 1,027 | 49 (4.8)[a, c, d] |

P values (by Fisher's exact test) are for between-group comparisons regarding the proportion of isolates associated with clinically diagnosed sepsis at the time of specimen collection or within 30 days thereafter.
[a] P = 0.043;
[b] P = 0.012;
[c] P = 0.001;
[d] P > 0.10.

The results of this study provide compelling evidence that clonal expansion was the dominant mechanism for the proliferation of both CTX-M-15 production and fluoroquinolone resistance in *E. coli* ST131. Past studies have shown that the determinants for both of these traits can be acquired through horizontal gene transfer. However, the whole genome SNP-based phylogenies presented here establish that almost all fluoroquinolone-resistant ST131 isolates share a single common ancestor. Moreover, 90% of the CTX-M-15-producing isolates formed an isolated subclone—which we termed H30-Rx—nested within the dominant fluoroquinolone-resistant ST131 subclone, H30-R.

These data may also suggest that antimicrobial resistance is not the sole selective characteristic leading to the proliferation of H30-R and H30-Rx, since other isolates were identified that possessed the same phenotypic resistance traits, but appeared to form unsuccessful subclones. Evaluation of the extended virulence gene profile of the H30-R and H30-Rx subclones identified nothing extraordinary, besides the predominance of the fimH30 allele. However, the fimH30 allele could not explain the striking association of the H30-Rx subclone with sepsis, since this feature was shared among isolates within and outside of this virulent H30-R subclone. Further investigations, including detailed comparative genomic analyses and functional studies, are needed to determine the basis for H30-Rx's strong association with sepsis.

The results of this whole genome SNP-based analysis depicted a considerably different evolutionary history for ST131 as compare to that derived from PFGE analysis. Use of an iterative approach to identify and exclude SNPs from recombinant regions elucidated an evolutionary path marked by clonal expansions rather than frequent lateral gene acquisitions. This underscores one of the major advantages of a whole genome SNP-based approach relative to PFGE. While PFGE uses signatures from throughout the genome, it is highly vulnerable to phylogenetic distortions by horizontal gene transfer, which can lead to false assumptions about the evolutionary history of an organism. PFGE is also limited by subjective interpretation of banding patterns and the (often invalid) presumption that similarly migrating bands represent the same chromosomal region.

The strong association between the H30-Rx subclone and sepsis, its broad multidrug-resistance profile, and its rapid geographic dispersal warrants the attention of the public health and clinical communities. While continued accumulation of antibiotic-resistance determinants may limit therapeutic options in the future, the clonal nature of H30-Rx may facilitate vaccine-based control strategies.

Example 21. Experimental Methods

The following experimental methods were used for the analyses discussed in Examples 22-23.
Specimen Collection We collected and analyzed all non-duplicate extraintestinal E. coli isolates from all specimen types submitted to two Olmsted County laboratories (serving Mayo Clinic and Olmsted Medical Center, the only health care centers in Olmsted County, Minn.) during February and March 2011. We included only 1 isolate per individual, from patients who provided research authorization. Antimicrobial susceptibility testing was performed by the clinical microbiology laboratories [Clinical and Laboratory Standards Institute (CLSI). Performance standards for antimicrobial susceptibility testing; nineteeth informational supplement (M100-S19). Wayne, Pa.: Clinical and Laboratory Standards Institute, 2009.]. Results were interpreted using breakpoints recommended by the Clinical and Laboratory Standards Institute [Clinical and Laboratory Standards Institute Institute (CLSI). Performance Standards for Antimicrobial Susceptibility Testing; Twentieth Informational Supplement. CLSI document M100-S20. Wayne, Pa.: Clinical and Laboratory Standards Institute, 2010.]. Isolates that were resistant or intermediate to a given antimicrobial were considered nonsusceptible. Multidrug-resistant (MDR) isolates were those resistant to ≥3 of the following drug classes: beta-lactams, fluoroquinolones, TMP/SMX, nitrofurantoin, aminoglycosides (Sahm D, Thornsberry C, Mayfield D, Jones M, Karlowsky J. Multidrug-resistant urinary tract isolates of Escherichia coli: prevalence and patient demographics in the United States in 2000. Antimicrob Agents Chemother 2001; 45:402-6.). The Mayo Clinic and Olmsted Medical Center Institutional Review Boards approved this study.
Clinical Data Abstraction We reviewed medical records to abstract demographic and clinical variables. Healthcare-associated isolates were defined as those collected from inpatients >72 hours after hospitalization, or from outpatients who had been hospitalized within 90 days prior to culture collection, were residents of a nursing home or long-term care facility (LTCF), and/or within 30 days prior to culture collection had received home intravenous therapy, wound care, specialized nursing, urinary catheterization, dialysis, or chemotherapy. Community-associated isolates were defined as those recovered from outpatients, or from inpatients hospitalized for <72 hours and who lacked the above healthcare-associated risk factors. An infection was considered uncomplicated if (i) E. coli was cultured from urine and (ii) the patient was treated as an outpatient and was immunocompetent, without genitourinary abnormalities or evidence of upper urinary tract infection. An infection was considered complicated if (i) E. coli was cultured from any extra-intestinal non-urine site or (ii) the patient was immunocompromised or hospitalized, had significant genitourinary abnormalities other than neurogenic bladder, or had upper urinary tract infection.
Molecular Characterization Major E. coli phylogenetic group (A, B1, B2, and D) was determined by triplex PCR [Clermont O, Bonacorsi S, Bingen E. Rapid and simple determination of Escherichia coli phylogenetic group. Appl Environ Microbiol 2000; 66:4555-4558.]. Three resistance-associated E. coli clonal groups—ST131, CGA, and O15:K52:H1—were identified by using PCR-based detection of clonal group-specific single-nucleotide polymorphisms in housekeeping genes [Johnson J, Menard M, Johnston B, Kuskowski M, Nichol K, Zhanel G. Epidemic clonal groups of Escherichia coli as a cause of antimicrobial-resistant urinary tract infections in Canada, 2002-2004. Antimicrob Agents Chemother 2009; 53:2733-2739.]. All isolates were clonally typed using CH typing [Weissman S, Johnson J, Tchesnokova V, et al. High resolution two-locus clonal typing of extraintestinal pathogenic Escherichia coli. Appl Environ Microbiol 2012; 78:1353-60.]. Based on the so-identified fumC and fimH allele combinations (i.e., CH types), sequence types (STs) were inferred with reference to a large private database (VT and EVS) containing CH types for diverse E. coli isolates that had undergone full 7-locus MLST (http://mlst.ucc.ie/mist/dbs/Ecoli). This allowed CH types to be cross-referenced to specific STs and single-locus variants thereof, which were included under the main ST designations. Within ST131, we also discriminated the H30 subclone from non-H30 subclones. The few CH types that mapped to multiple STs were assigned to the numerically most-probable ST.
Statistical Analysis Comparisons between groups were evaluated using Kruskal-Wallis, Wilcoxon rank sum, chi-square, and Fisher exact tests, as appropriate. All tests were two-sided. P values<0.05 were considered statistically significant. Simpson's diversity index was used to analyze genotypic diversity of isolates [Simpson E. Measurement of Diversity. Nature 1949; 163:688; Chattopadhyay S, Feldgarden M, Weissman S, Dykhuizen D, Belle Gv, Sokurenko E. Haplotype diversity in source-sink dynamics of Escherichia coli urovirulence. J Mol Evol 2007; 64:204-214.]. Isolates that could not be assigned a ST were excluded from diversity analyses.

Example 22. ST Distribution

A total of 299 consecutive single-patient E. coli clinical isolates were characterized. Most were from urine (90%), outpatients (68%), and community-associated (CA) infections (61%) (Table 14). The median patient age was 58 years. Isolates overwhelmingly belonged to phylogenetic group B2 (71%), followed distantly by groups D (17%), A (6%), and B1 (6%). Forty-seven different STs were identified, the most common being ST131 (27%), ST95 (11%), ST73 (8%), ST127 (6%), and ST69 (5%). Within the ST131 clonal group, the H30 ST131 subclone accounted for 70 (88%) of 80 isolates. Only 20 isolates (6.6%), which contained novel fimH alleles, could not be assigned to a ST using the CH typing strategy. Clonal group-specific SNP PCR agreed precisely with CH typing for identifying ST131, CGA (ST69), and the O15:K52:H1 (ST393) clonal group.

Figure 13:
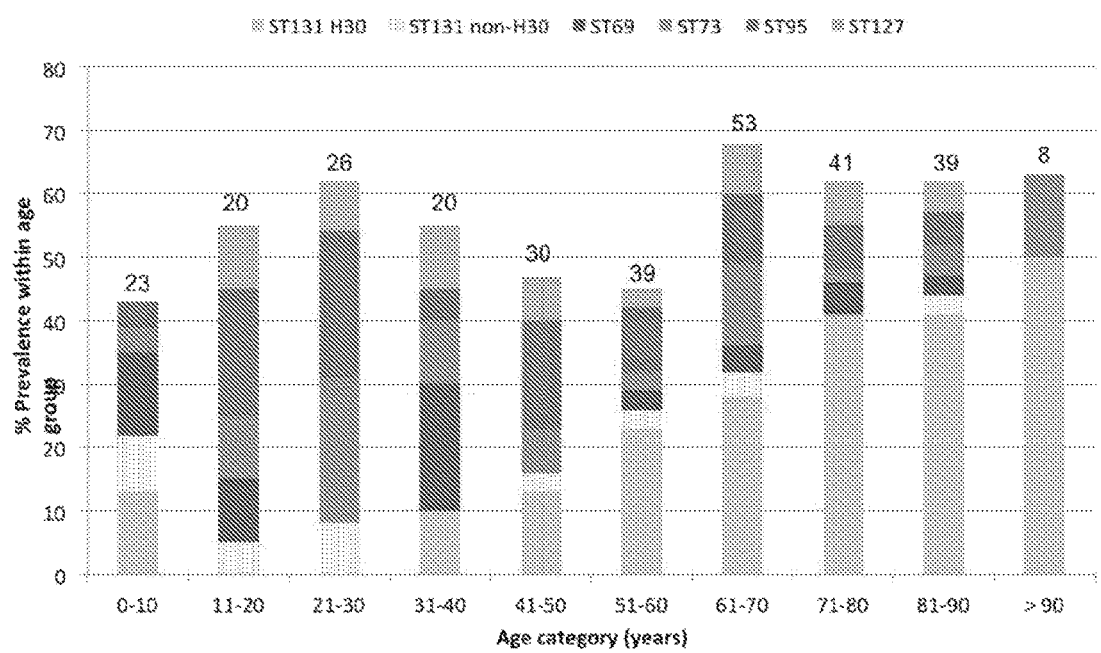
FIG. 13 shows clonal distribution of extraintestinal Escherichia coli isolates according to patient age group.

Although the 5 most common STs accounted collectively for a near majority of isolates within each age group, their distribution varied significantly with decade (p=0.001) (Table 14). ST131, represented almost exclusively by its H30 subclone, was the most common ST among adults >50 years old and increased in prevalence with age, as previously described [Banerjee R, Johnston B, Lohse C, Porter S, Clabots C, Johnson J. *Escherichia coli* sequence type ST131 is a dominant, antimicrobial-resistant clonal group associated with healthcare and elderly hosts. Infect Control Hosp Epidemiol 2013; 34:361-9]. In contrast, among children <10 years old both H30 and non-H30 ST131 isolates were prevalent, and among subjects 11-30 years old non-H30 ST131 isolates were more common than H30 ST131 isolates (FIG. 13). ST distribution did not vary by gender (not shown).

TABLE 14

Clinical and demographic features according to sequence type (ST) among 299 *Escherichia coli* isolates.

| Characteristic | All N = 299 | ST131 N = 80 | ST95 N = 32 | ST73 N = 25 | ST127 N = 18 | ST69 N = 15 | Other[a] N = 129 | P value |
|---|---|---|---|---|---|---|---|---|
| Age (years) | | | | | | | | |
| ≤10 | 23 (8) | 5 (6) | 1 (3) | 1 (4) | 0 | 2 (20) | 13 (10) | <0.01 |
| 11-50 | 96 (32) | 10 (13) | 16 (50) | 12 (48) | 8 (44) | 6 (40) | 44 (34) | |
| >50 | 180 (60) | 65 (81) | 15 (47) | 12 (48) | 10 (56) | 6 (40) | 72 (56) | |
| Sex | | | | | | | | |
| Female | 238 (80) | 63 (79) | 28 (88) | 19 (76) | 14 (78) | 13 (87) | 101 (78) | 0.84 |
| Male | 61 (20) | 17 (21) | 4 (13) | 6 (24) | 4 (22) | 2 (13) | 28 (22) | |
| Race[b] | | | | | | | | |
| White | 243 (91) | 62 (90) | 27 (93) | 23 (100) | 14 (88) | 12 (92) | 105 (91) | 0.68 |
| Non-White | 23 (9) | 7 (10) | 2 (7) | 0 | 2 (13) | 1 (8) | 11 (9) | |
| Acquisition[b] | | | | | | | | |
| CA[c] | 180 (61) | 27 (34) | 21 (68) | 18 (72) | 14 (78) | 11 (73) | 89 (70) | <0.01 |
| HA[d] | 117 (39) | 53 (66) | 10 (32) | 7 (28) | 4 (22) | 4 (27) | 39 (30) | |
| Source | | | | | | | | |
| Urine | 268 (90) | 68 (85) | 28 (88) | 24 (96) | 17 (94) | 13 (87) | 118 (91) | 0.40 |
| Blood | 17 (6) | 5 (6) | 4 (13) | 1 (4) | 1 (6) | 1 (7) | 5 (4) | |
| Other | 14 (5) | 7 (9) | 0 | 0 | 0 | 1 (7) | 6 (5) | |
| Severity[b] | | | | | | | | |
| Colonization | 34 (12) | 7 (9) | 4 (13) | 4 (17) | 3 (18) | 1 (7) | 15 (12) | 0.27 |
| Un-complicated | 211 (72) | 52 (67) | 19 (61) | 19 (79) | 12 (71) | 11 (73) | 98 (77) | |
| Complicated | 48 (16) | 19 (24) | 8 (26) | 1 (4) | 2 (12) | 3 (20) | 15 (12) | |
| Residence[b] | | | | | | | | |
| Non-LTCF[c] | 261 (88) | 52 (65) | 29 (94) | 24 (96) | 17 (94) | 15 (100) | 124 (96) | <0.01 |
| LTCF | 37 (12) | 28 (35) | 2 (6) | 1 (4) | 1 (6) | 0 | 5 (4) | |

[a]Other includes: ST58 (N = 12); ST141 (N = 11); ST10 (N = 10); ST38 (N = 9); ST144 (N = 7); ST372 and ST12 (N = 6 each); ST393 and ST14 (N = 4 each); ST101, ST1193, ST405, ST59, ST62, and ST80 (N = 2 each); and ST10160, ST1146, ST1148, ST117, ST130, ST1670, ST2260, ST2541, ST2556, ST28, ST297, ST349, ST354, ST420, ST448, ST491, ST54, ST625, ST646, ST648, ST681, ST701, ST83, S1929, ST973, and ST11089 (N = 1 each).
[b]Isolates with missing data were excluded, leaving N = 266 for race; N = 297 for acquisition; N = 293 for severity; and N = 298 for residence.
[c]CA, community-associated.
[d]HA, hospital-associated.
[e]LTCF, long-term care facility.

TABLE 15

Antimicrobial resistance according to sequence type (ST) among 299 extraintestinal *Escherichia coli* isolates.

| Antimicrobial | All N = 299 | ST131[a] N = 80 | ST9 N = 32 | ST73 N = 25 | ST127 N = 18 | ST69 N = 15 | Other N = 129 | P value |
|---|---|---|---|---|---|---|---|---|
| Fluoroquinolone | 88 (29) | 71 (89) | 0 | 0 | 0 | 1 (7) | 16 (12) | <0.01 |
| Ampicillin | 156 (52) | 65 (81) | 13 (41) | 10 (40) | 4 (22) | 11 (73) | 3 (41) | <0.01 |
| Ceftriaxone (N = 259)[b] | 16 (6) | 8 (11) | 0 | 0 | 0 | 0 | 8 (7) | 0.28 |
| Gentamicin | 29 (10) | 23 (29) | 0 | 0 | 1 (6) | 0 | 5 (4) | <0.01 |
| TMP/SMX[c] | 88 (29) | 37 (46) | 2 (6) | 3 (12) | 1 (6) | 8 (53) | 37 (29) | <0.01 |

TABLE 15-continued

Antimicrobial resistance according to sequence type (ST)
among 299 extraintestinal *Escherichia coli* isolates.
No. of resistant isolates (column %)

| Anti-microbial | All N = 299 | ST131[a] N = 80 | ST9 N = 32 | ST73 N = 25 | ST127 N = 18 | ST69 N = 15 | Other N = 129 | P value |
|---|---|---|---|---|---|---|---|---|
| Cefazolin (N = 297)[b] | 93 (31) | 45 (57) | 3 (9) | 7 (28) | 3 (17) | 5 (33) | 30 (23) | <0.01 |
| Nitrofur-antoin (N = 274)[b] | 8 (3) | 3 (4) | 1 (3) | 1 (4) | 0 | 0 | 3 (2) | 0.93 |
| Piperacillin/ tazobactam | 6 (2) | 1 (1) | 0 | 2 (8) | 1 (6) | 0 | 2 (2) | 0.20 |
| Imipenem (N = 258)[b] | 3 (1) | 0 | 0 | 0 | 2 (14) | 0 | 1 (1) | 0.03 |
| FQ[d] + TMP/SMX | 46 (15) | 33 (41) | 0 | 0 | 0 | 1 (7) | 12 (9) | <0.01 |
| Any beta-lactam[e] (N = 256)[b] | 141 (55) | 59 (84) | 11 (42) | 8 (38) | 5 (36) | 9 (82) | 49 (43) | <0.01 |
| MDR[f] (N = 233)[b] | 42 (18) | 30 (51) | 0 | 0 | 1 (8) | 0 | 11 (10) | <0.01 |
| None of above[g] (N = 233)[a] | 96 (41) | 1 (2) | 13 (52) | 13 (65) | 9 (69) | 1 (11) | 59 (55) | <0.01 |

[a]Resistance prevalence among H30 (N = 70) vs. non-H30 (N = 10) ST131 was as follows: FQ (100% vs. 10%, P < .01), ampicillin (81% vs. 80%, P = 1), ceftriaxone (9% vs. 29%, P = .18), gentamicin (30 vs. 20%, P = .72), TMP/SMX (47% vs. 40%, P = .75), cefazolin (58% vs. 50%, P = .74), nitrofurantoin (3% vs. 13%, P = .32), piperacillin/tazobactam (1% vs. 0%, P = 1), FQ + TMP/SMX (47% vs. 0%. P < .01), any beta-lactam (86% vs. 71%, P = .30), MDR (52% vs. 40%, P = .67), none of above (0% vs. 20%, P = .08).
[b]Not all isolates were tested against all agents, accounting for the smaller sample size in some rows.
[c]TMP/SMX, trimethoprim-sulfamethoxazole.
[d]FQ, fluoroquinolone.
[e]Beta-lactams: ampicillin, ceftriaxone, cefazolin, piperacillin/tazobactam, and imipenem.
[f]Multidrug-resistant (MDR) isolates were those resistant to ≥3 of the following drug classes: beta-lactams, fluoroquinolones, TMP/SMX, nitrofurantoin, aminoglycosides.
[g]Resistant to none of the tested agents.

Figure 14:
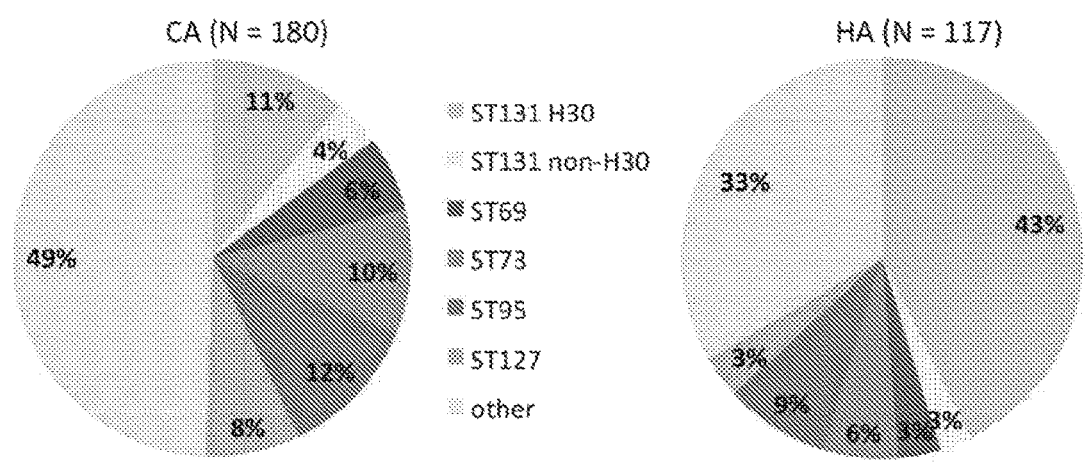
FIG. 14 shows the distribution of Escherichia coli sequence types (STs) among patients with community-associated (CA) or healthcare-associated (HA) extraintestinal E. coli isolates.

ST distribution also differed by site of infection acquisition, complicated vs. uncomplicated infection, and specimen type (FIG. 14, Table 14). Regarding site of acquisition, isolates from the five most common STs comprised two-thirds of HA isolates but only half of CA isolates (FIG. 14). This association was due to ST131, in particular its H30 subclone, since two-thirds of ST131 isolates were HA and one third were CA, whereas for all other STs the majority of isolates were CA (P<0.001) (Table 14). Additionally, ST131 comprised 76% of isolates from LTCF residents, a significantly higher proportion than other STs (0-14%: P<0.001), which in contrast accounted for most isolates from patients who did not reside in LTCFs. ST95 and ST131 accounted jointly for a significantly higher proportion of complicated infections than did other STs (P=0.003). Within each ST, the proportion of non-urine isolates was higher for ST131 (15%), ST69 (14%), and ST95 (13%) than for other STs (0-9%).

ST distribution likewise varied by resistance phenotype (Table 15). ST131 was the most extensively antimicrobial-resistant ST, displaying high prevalence of resistance to fluoroquinolones (89%), any beta-lactam (84%), trimethoprim-sulfamethoxazole (TMP-SMX) (46%), and multidrug-resistance (51%). Within ST131, all 70 (100%) H30 subclone isolates were resistant to fluoroquinolones, as compared with only 1 (10%) of the 10 non-H30 ST131 isolates. Over half of isolates within ST95, ST73, and ST127 were fully antimicrobial-susceptible. ST69 stood out from the other prevalent non-ST131 STs, and more closely resembled ST131, with its high prevalence of resistance to beta-lactams (82%, vs. 81% for ST131) and TMP-SMX (53%, vs. 46% for ST131) (Table 15).

Example 23. CH Type Diversity

To quantify and compare genotypic diversity among isolate groups, we used Simpson's diversity index, with which higher numbers indicate lower diversity (Table 16). Diversity of STs did not differ by gender or specimen type. However, ST diversity was significantly lower among isolates from patients >50 years old than among those from patients 11-50 years old. When we excluded the H30 ST131 subclone, ST diversity increased most dramatically among patients >50 years old, becoming significantly higher than the diversity of entire dataset (P<0.001). This result is consistent with the predominance of the H30 ST131 subclone among patients >50 years old, as depicted in FIG. 13. Also, HA isolates were significantly less diverse than CA isolates. Similarly, isolates resistant to any given antimicrobial agent, or to combinations thereof, were significantly less diverse than isolates with the corresponding susceptible phenotype. The observed difference in clonal diversity was due primarily to the differential distribution of the H30 ST131 subclone. Accordingly, when H30 isolates were excluded from these analyses the estimated diversity among HA and antimicrobial-resistant isolates increased to match that of the CA and susceptible isolates (Table 16).

In this clonal survey we characterized the clonal distribution, clonal diversity, and associated clinical characteristics of consecutively sampled extraintestinal *E. coli* isolates in a region within the upper US Midwest by using CH typing, a novel, rapid, and discriminatory strategy for clonal typing. We determined that different *E. coli* STs varied in prevalence by patient age, type of infection, and resistance phenotype. Specifically, the H30 ST131 subclone was especially common among very young children, older adults, HA infections, and antimicrobial-resistant isolates, whereas non-H30 ST131 and other well-known pathogenic lineages were common among older children, young adults, CA infections, and antimicrobial-susceptible isolates.

Five STs comprised well over half of the isolates in our collection, as in similar recent collections [17, 19]. The most prevalent STs we identified correspond closely with those found in several other geographic regions. However, in the San Francisco Bay area ST12 but not ST127 was noted as a prevalent clonal group. This difference could be related to geographic variation or the fact that the San Francisco study evaluated only blood isolates, while our isolates were primarily from urine. Across all these studies, ST131 was the most common ST identified. Notably, our ST131 prevalence (27%) was higher than found in prior studies (the next highest being 23% [17]), likely due to geographic or host population differences, and/or increasing ST131 prevalence over time.

We found that genotypic diversity was lower among antimicrobial-resistant isolates than among antimicrobial-susceptible isolates, as noted previously, and among HA isolates compared to CA isolates. Furthermore, we found that when the H30 subclone ST131 isolates were excluded the diversity of HA and antimicrobial-resistant isolates increased substantially, to a level matching that of the CA and antimicrobial-susceptible isolates. This suggests that the clonal expansion (and consequent predominance) of the H30 ST131 subclone is responsible for the observed lower diversity of the HA and antimicrobial-resistant subgroups. These findings, together with earlier work by our group and others, support the idea that the H30 ST131 subclone is expanding within healthcare facilities, which emphasizes the need for more effective antimicrobial stewardship and infection prevention efforts in these settings. In contrast, the greater diversity observed among CA isolates suggests that expansion of specific clonal groups has not occurred to nearly the same extent in the community as in healthcare settings.

In conclusion, we found that in the study region within the upper US Midwest, E. coli clonal group distribution and diversity varied by patient age, community vs. hospital-associated status, and resistance phenotype. We conclude that the resistance-associated H30 ST131 subclone, more than other clonal groups, has expanded in healthcare settings, likely in part due to widespread, often inappropriate antimicrobial use, inadequate infection control practices, and a high proportion of elderly patients who serve as reservoirs of this subset within ST131. In addition, we confirmed that CH typing is a rapid clonal typing method, feasible for evaluating large numbers of isolates. Since CH typing is based on sequencing of two loci, it is faster and cheaper than standard MLST, and is likely to become a widely-used strategy in future studies of E. coli molecular epidemiology and clonal group surveillance.

TABLE 16

Simpson diversity indices according to patient characteristics and resistance phenotypes, with and without the H30 ST131 subclone.

| Feature | Including all ST131 isolates | | Excluding H30 ST131 subclone isolates | |
|---|---|---|---|---|
| | Simpson Index (SE$^a$) | P value | Simpson Index (SE$^a$) | P value |
| All | .12 (.01) | | .07 (.01) | <.01$^b$ |
| Age (years) | | | | |
| <10 | .12 (.03) | .53$^c$ | .10 (.02) | 1$^c$ |
| 11-50 | .10 (.01) | .03$^d$ | .10 (.02) | .07$^d$ |
| >50 | .17 (.03) | .18$^e$ | .06 (.01) | .07$^e$ |
| Sex | | | | |
| Female | .12 (.02) | | .07 (.01) | |
| Male | .12 (.03) | 1 | .07 (.01) | |
| Acquisition | | | | |
| CA$^f$ | .08 (.01) | | .07 (.01) | |
| HA$^g$ | .25 (.04) | <.01 | .07 (.01) | .79 |
| Source | | | | |
| Urine | .11 (.01) | | .07 (.01) | |
| Non-urine | .21 (.07) | .13 | .10 (.03) | .31 |
| Fluoroquinolone | | | | |
| susceptible | .08 (.01) | | .08 (.01) | |
| resistant | .69 (.07) | <.01 | .14 (.04) | .11 |
| Ampicillin | | | | |
| susceptible | .08 (.01) | | .08 (.01) | |
| resistant | .22 (.03) | <.01 | .08 (.01) | 1 |
| TMP/SMX$^h$ | | | | |
| susceptible | .10 (.01) | | .08 (.01) | |
| resistant | .23 (.05) | <.01 | .08 (.01) | .35 |
| Cefazolin | | | | |
| susceptible | .09 (.01) | | .08 (.01) | |
| resistant | .28 (.05) | <.01 | .08 (.01) | 1 |
| Beta-lactams$^i$ | | | | |
| susceptible | .07 (.01) | | .08 (.01) | |
| resistant | .22 (.03) | <.01 | .07 (.01) | .13 |
| MDR$^j$ | | | | |
| No | .08 (.01) | | .08 (.01) | |
| Yes | .54 (.10) | <.01 | .11 (.02) | .14 |
| Any resistance | | | | |
| No | .08 (.01) | | .08 (.01) | |
| Yes | .23 (.04) | <.01 | .08 (.01) | .91 |

Note:
20 isolates with unknown ST by CH typing were excluded.
$^a$SE, standard error.
$^b$Compares diversity among all isolates with and without STI 31. All other P values compare diversity between subgroups of each variable within the categories "with ST131" or "without ST131."
$^c$Compares diversity between <10 years and 11-50 years.
$^d$Compares diversity between 11-50 years and >50 years.
$^e$Compares diversity between <10 years and >50 years.
$^f$CA, community-associated.
$^g$HA, healthcare-associated.
$^h$TMP/SMX: trimethoprim-sulfamethoxazole.
$^i$beta-lactam: ampicillin, ceftriaxone, cefazolin, piperacillin/tazobactam, and imipenem.
$^j$MDR: multidrug-resistant (i.e., resistant to ≥3 of t the following classes: fluoroquinolones, beta-lactams, TMP/SMX, gentamicin, nitrofurantoin).

Example 24. Experimental Methods

The following experimental methods were used for the analyses discussed in Examples 25-29.

Patients and Isolates

During 2011 the clinical microbiology laboratories of 24 widely distributed Veteran Affairs Medical Centers (VAMCs) submitted 10 each de-identified FQ-R and FQ-susceptible (FQ-S) extraintestinal clinical E. coli isolates from 2011, plus (because of their comparative rarity) up to 10 archived ESBL-producing E coli isolates from 2010-2011. For the FQ-S and FQ-R isolates, laboratories prospectively saved 10 consecutive FQ-R isolates and, in parallel, 10 arbitrarily selected FQ-S isolates. Isolates were submitted to the research laboratory accompanied by approximate collection date, specimen type, origin (inpatient vs. outpatient), and susceptibility data, plus the source laboratory's current cumulative *E. coli* susceptibility data.

The 24 VAMCs were in the District of Columbia and 17 U.S. states (California, Colorado, Florida, Idaho, Indiana, Iowa, Massachusetts, Michigan, Minnesota, Mississippi, Missouri, New York, Ohio, Tennessee, Texas, Utah, Washington, and Wisconsin). They were assigned to one of four main U.S. census regions (i.e., West, Midwest, South, and Northeast) based on location (Johnson J R, Nicolas-Chanoine M H, DebRoy C, et al. Comparison of *Escherichia coli* ST131 pulsotypes, by epidemiologic traits, 1967-2009. Emerg Infect Dis 2012; 18(4): 598-607). Local institutional review boards and research oversight committees approved the study protocol.

Molecular Methods

Isolates were assessed for ST131 genotype by PCR-based detection of ST131-specific single-nucleotide polymorphism (SNPs) in gyrB and mdh (Johnson J R, Menard M, Johnston B, Kuskowski M A, Nichol K, Zhanel G G. Epidemic clonal groups of *Escherichia coli* as a cause of antimicrobial-resistant urinary tract infections in Canada, 2002 to 2004. Antimicrob Agents Chemother 2009; 53(7): 2733-9), with selective confirmation by multi-locus sequence typing (MLST). ST131 isolates were tested by allele-specific primers for allele 30 of fimH (encoding a variant of the type 1 fimbrial adhesin) corresponding with the main FQ-resistance-associated subset within ST131, the H30 sub-clone (Johnson J R, Tchesnokova V, Johnston B, et al. Abrupt Emergence of a Single Dominant Multidrug-Resistant Strain of *Escherichia coli*. J Infect Dis 2013; Johnson J R, Menard M, Johnston B, Kuskowski M A, Nichol K, Zhanel G G. Epidemic clonal groups of *Escherichia coli* as a cause of antimicrobial-resistant urinary tract infections in Canada, 2002 to 2004. Antimicrob Agents Chemother 2009; 53(7): 2733-9.). Primers fimH30F-21 (CCGCCAATGGTACCGCTATT) (SEQ ID NO: 1) and fimH30R-20 (CAGCTTTAATCGCCACCCCA) (SEQ ID NO: 2) (354 bp product) underwent PCR as follows: 8' at 95o; 30 cycles of (20 s at 94o and 45 s at 68o); 5' at 72o; hold at 4o. Additionally, 20 each randomly selected FQ-S and FQ-R non-ST131 isolates underwent MLST, followed by sub-sequence type (ST) stratification using fumC-fimH (CH) typing, which utilizes a 489-nucleotide (nt) internal fragment of fimH to resolve within-ST sub-clones (Weissman S J, Johnson J R, Tchesnokova V, et al. High-resolution two-locus clonal typing of extraintestinal pathogenic *Escherichia coli*. Appl Environ Microbiol 2012; 78(5): 1353-60).

Major *E. coli* phylogenetic group (A, B1, B2, and D) was determined by triplex PCR (Clermont O, Bonacorsi S, Bingen E. Rapid and simple determination of the *Escherichia coli* phylogenetic group. Appl Environ Microbiol 2000; 66(10): 4555-8). Presence of 54 extraintestinal virulence genes was assessed by multiplex PCR (Johnson J R, Menard M, Johnston B, Kuskowski M A, Nichol K, Zhanel G G. Epidemic clonal groups of *Escherichia coli* as a cause of antimicrobial-resistant urinary tract infections in Canada, 2002 to 2004. Antimicrob Agents Chemother 2009; 53(7): 2733-9; Johnson J R, Johnston B, Kuskowski M A, Nougayrede J P, Oswald E. Molecular epidemiology and phylogenetic distribution of the *Escherichia coli* pks genomic island. J Clin Microbiol 2008; 46(12): 3906-11; Johnson J R, Stell A L. Extended virulence genotypes of *Escherichia coli* strains from patients with urosepsis in relation to phylogeny and host compromise. J Infect Dis 2000; 181(1): 261-72). The virulence factor (VF) score was the total number of virulence genes detected, adjusted for multiple detection of the pap (P fimbriae), sfa/foc (S and F1C fimbriae), and kps (group 2 capsule) operons. Isolates were classified as extraintestinal pathogenic *E. coli* (ExPEC) if positive for ≥2 of: papAH and/or papC (P fimbriae), sfa/focDE, afa/draBC (Dr-family adhesins), iutA (aerobactin receptor), and kpsM II (group 2 capsule synthesis) (Johnson J R, Murray A C, Gajewski A, et al. Isolation and molecular characterization of nalidixic acid-resistant extraintestinal pathogenic *Escherichia coli* from retail chicken products. Antimicrob Agents Chemother 2003; 47(7): 2161-8.).

XbaI pulsed-field gel electrophoresis (PFGE) analysis was used to assign isolates to pulsotypes based on 94% profile similarity to reference strains (Ribot E M, Fair M A, Gautom R, et al. Standardization of pulsed-field gel electrophoresis protocols for the subtyping of *Escherichia coli* O157:H7, *Salmonella*, and *Shigella* for PulseNet. Foodborne Pathog Dis 2006; 3(1): 59-67.). A PFGE dendrogram was inferred within BioNumerics (v. 6.6; Applied Maths, Austin, Tex.) according to the unweighted pair group method based on Dice coefficients (Johnson J R, Nicolas-Chanoine M H, DebRoy C, et al. Comparison of *Escherichia coli* ST131 pulsotypes, by epidemiologic traits, 1967-2009. Emerg Infect Dis 2012; 18(4): 598-607.). Profiles also were compared with a large private PFGE profile reference library (Johnson J R, Nicolas-Chanoine M H, DebRoy C, et al. Comparison of *Escherichia coli* ST131 pulsotypes, by epidemiologic traits, 1967-2009. Emerg Infect Dis 2012; 18(4): 598-607).

Susceptibility Testing

Susceptibility results for nine antimicrobial agents (ampicillin, ampicillin/sulbactam, cefazolin, ceftriaxone, ciprofloxacin, imipenem, gentamicin, nitrofurantoin, and trimethoprim-sulfamethoxazole [TMP-SMZ]) were as provided by participating VAMCs based on local broth microdilution or disk diffusion testing. Reported susceptibility results, if conflicting with the assigned resistance category, were reassessed by disk diffusion, using Clinical Laboratory Standards Institute-specified methods, ATCC reference strains, and interpretive criteria (Clinical and Laboratory Standards Institute. M100-S21 (M100) 2011: performance standards for antimicrobial susceptibility testing: 21st informational supplement), and isolates were reclassified accordingly. Intermediate interpretations were analyzed as resistant. The resistance score was the number of agents to which an isolate exhibited resistance. Multidrug resistance (MDR) was defined using two thresholds, i.e., resistance to ≥3 or ≥5 drug classes (counting penicillins and cephalosporins separately) (Sahm D F, Thornsberry C, Mayfield D C, Jones M E, Karlowsky J A. Multidrug-resistant urinary tract isolates of *Escherichia coli*: prevalence and patient demographics in the United States in 2000. Antimicrob Agents Chemother 2001; 45(5): 1402-6).

Population Estimates

The overall population prevalence of ST131, other clonal groups, and resistance to individual or combined antimicrobial agents were estimated by back calculations based on the observed prevalence of each clonal group or resistance phenotype amongst the FQ-R and FQ-S study isolates, respectively, and the relative sizes of the FQ-R and FQ-S populations, according to the reported prevalence of ciprofloxacin resistance in *E. coli* at the participating laboratories (median 29%; range, 21%-53%) (Table 17). ST131-specific resistance contributions were calculated similarly for each resistance phenotype as the product of (i) the observed prevalence of the particular phenotype amongst FQ-S and FQ-R ST131 isolates, respectively, (ii) the proportion of FQ-S and FQ-R isolates that were ST131 (FIG. 1), and (iii) the relative sizes of the FQ-R and FQ-S populations (determined as above) (Table 17). The overall prevalence of each resistance phenotype among ST131, H30 ST131, and other *E. coli* was estimated similarly (Table 18).

Statistical Analysis

Comparisons of proportions and continuous variables were tested by using Fisher's exact test and the Mann-Whitney U test, respectively (both, 2-tailed). The significance criterion was P<0.05.

TABLE 17

Estimated overall contribution of ST131 to antimicrobial resistance in *Escherichia coli* among U.S. veterans.

| Resistance phenotype | Overall prevalence in population, %[a] | Estimated fraction due to ST131[b] |
|---|---|---|
| Ampicillin | 46 | .46 |
| Ampicillin/sulbactam | 34 | .48 |
| Cefazolin | 17 | .47 |
| Ceftriaxone | 2 | .43 |
| Ciprofloxacin | 29 | .78 |
| Gentamicin | 11 | .76 |
| TMP-SMZ[c] | 22 | .56 |
| Imipenem | 0.25 | .50 |
| Nitrofurantoin | 6 | .36 |
| MDR[d] ≥3 | 24 | .70 |
| MDR[d] ≥5 | 2 | .55 |
| Ciprofloxacin + TMP-SMZ[c] | 15 | .76 |
| Ciprofloxacin + TMP-SMZ[c] + Ampicillin | 14 | .76 |

[a]Based on the median value for cumulative prevalence of fluoroquinolone (FQ) resistance in *E. coli* as reported by the participating VAMC laboratories (29%) and the observed prevalence of the listed resistance phenotypes among FQ-R and EQ-S study isolates, respectively. The calculation was as follows: overall prevalence of phenotype in source population = .29 (prevalence of phenotype among FQ-R study isolates) + .71 (prevalence of phenotype among FQ-S study isolates).
[b]Based on the assumed 29% overall prevalence of FQ resistance (see above), the observed prevalence of ST131 among FQ-R and FQ-S study isolates (FIG. 1), and the observed prevalence of the listed resistance phenotypes amongst the FQ-R and FQ-S ST131 study isolates, respectively.
[c]TMP-SMZ, trimethoprim-sulfamethoxazole.
[d]MDR, multi-drug resistance to ≥3 or ≥5 drug classes.

Example 25. Prevalence of ST131 and the H30 ST131 Sub-Clone

Figure 19:
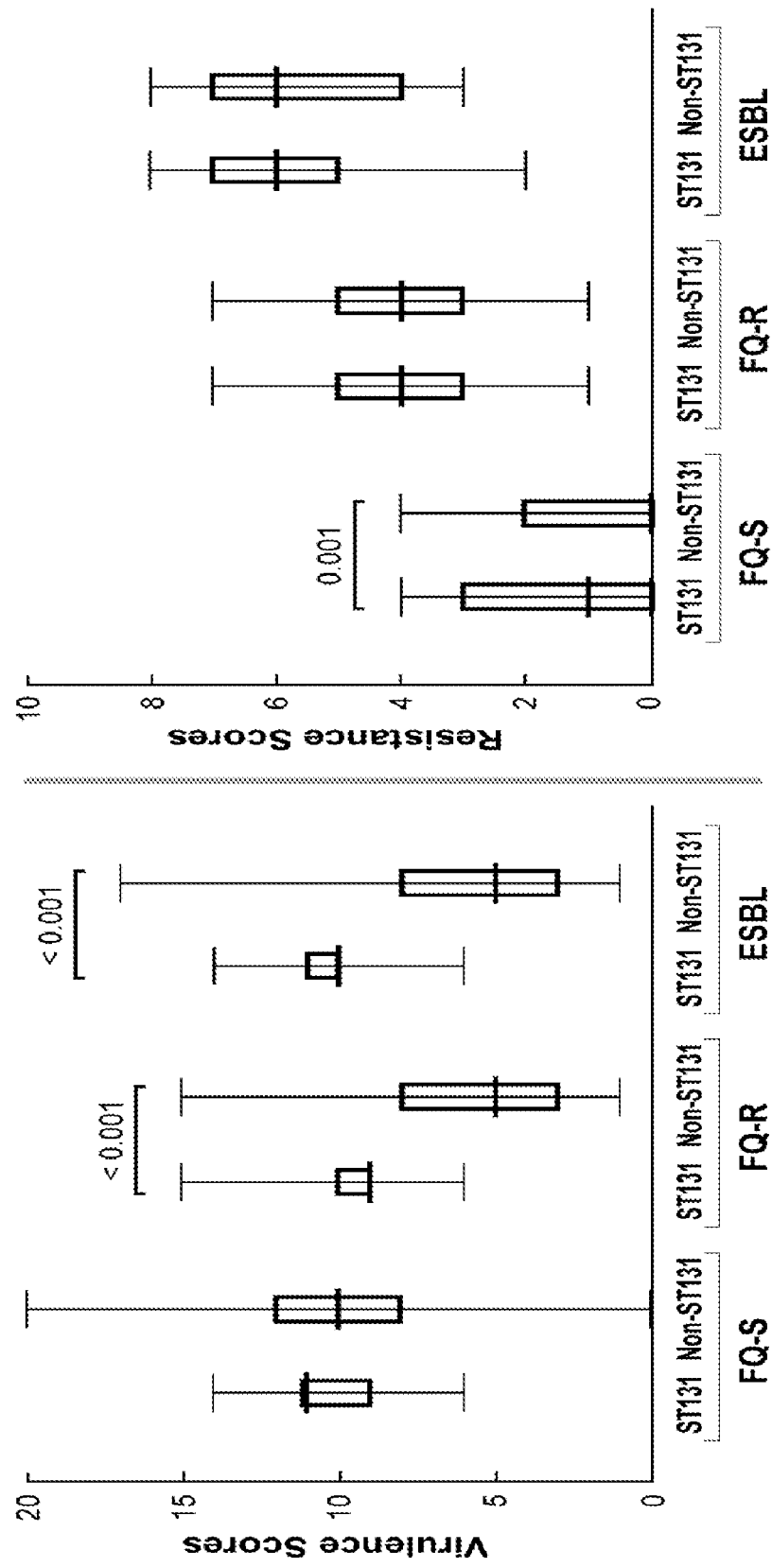
FIG. 19 shows virulence and resistance scores among ST131 and non-ST131 Escherichia coli isolates within three resistance groups.

The 595 *E. coli* study isolates were from 24 widely distributed VAMCs and constituted 3 susceptibility groups, i.e., FQ-S (n=236), FQ-R (n=236), and ESBL (n=123). Although the overall distribution of phylogenetic groups A, B1, B2, and D was fairly similar across the three susceptibility groups, with group B2 consistently predominating, ST131 accounted for 78% of the FQ-R isolates and 64.2% of the ESBL isolates, but only 7.2% of the FQ-S isolates (P<0.001, vs. FQ-R or ESBL) (FIG. 19). Moreover, the H30 ST131 sub-clone—a recently emerged, FQ resistance-associated lineage within ST131 (Johnson J R, Menard M, Johnston B, Kuskowski M A, Nichol K, Zhanel G G. Epidemic clonal groups of *Escherichia coli* as a cause of antimicrobial-resistant urinary tract infections in Canada, 2002 to 2004. Antimicrob Agents Chemother 2009; 53(7): 2733-9; Johnson J R, Stell A L. Extended virulence genotypes of *Escherichia coli* strains from patients with urosepsis in relation to phylogeny and host compromise. J Infect Dis 2000; 181(1): 261-72)—accounted for 95%-97.8% of ST131 isolates within the FQ-R and ESBL groups, but only 12.5% of those within the FQ-S group (P<0.001, vs. FQ-R or ESBL) (FIG. 15).

Figure 15:
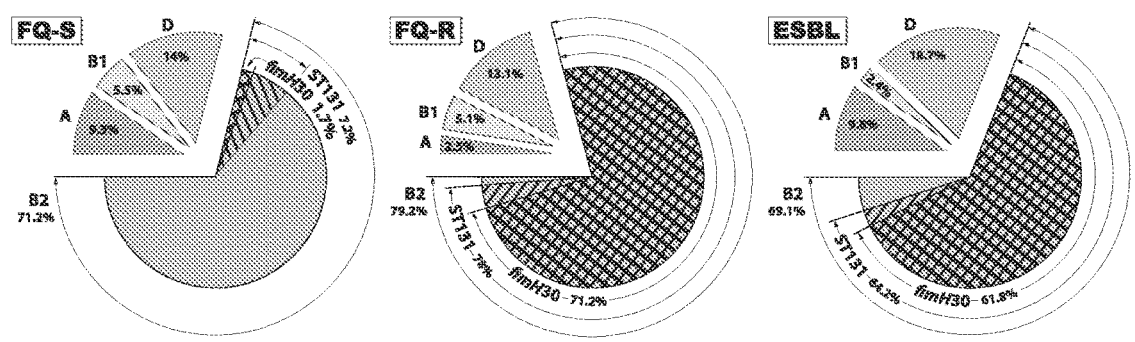
FIG. 15 shows the distribution by resistance group of major Escherichia coli phylogenetic groups, ST131, and the fimH30 sub-clone among 595 E. coli isolates from veterans.

FIG. 15 presents the distribution by resistance group of major *Escherichia coli* phylogenetic groups, ST131, and the fimH30 sub-clone among 595 *E. coli* isolates from veterans. FQ-R and FQ-S indicate fluoroquinolone-resistant and fluoroquinolone susceptible. ESBL, extended-spectrum beta-lactamase. Major phylogenetic groups are: A (pink), B1 (yellow), B2 (blue), and D (green). ST131, fine cross-hatching. fimH30 sub-clone, bold cross-hatching. For prevalence of ST131 and the fimH30 ST131 sub-clone in the FQ-S group vs. the FQ-R or ESBL group, P<0.001.

TABLE 18

Overall prevalence of antimicrobial resistance among ST131 and H30 subclone isolates, compared with other isolates, among *Escherichia coli* clinical isolates from U.S. veterans.

| | | Prevalence of resistance[a] and hazard ratio[b] | | | | | |
|---|---|---|---|---|---|---|---|
| | | ST131 vs. others | | | H30 subclone vs. others | | |
| Resistance phenotype | Total[a] (%) | T131[a] | Others[a] (%) | Hazard ratio[b] | H30 ST131[a] | Others[a] (%) | Hazard ratio[b] |
| Ampicillin | 46 | 77 | 34 | 2.3 | 76 | 36 | 2.1 |
| Ampicillin/sulbactam | 34 | 58 | 24 | 2.4 | 57 | 27 | 2.1 |
| Cefazolin | 17 | 29 | 12 | 2.3 | 27 | 14 | 2.0 |
| Ceftriaxone | 2 | 3 | 2 | 1.9 | 4 | 2 | 2.0 |
| Ciprofloxacin | 29 | 81 | 9 | 9.2 | 90 | 10 | 9.3 |
| Gentamicin | 11 | 29 | 3 | 8.2 | 28 | 5 | 5.4 |
| TMP—SMZ[c] | 22 | 42 | 13 | 2.4 | 47 | 14 | 3.3 |
| Imipenem | 0.25 | 0.4 | 0.2 | 1.4 | 0.5 | 0.2 | 1.4 |
| Nitrofurantoin | 6 | 8 | 5 | 3.2 | 8 | 5 | 3.4 |
| MDR[d] ≥ 3 | 24 | 59 | 10 | 6.2 | 63 | 11 | 5.8 |
| MDR[d] ≥ 5 | 2 | 5 | 1 | 3.2 | 6 | 1 | 3.9 |
| Ciprofloxacin + TMP—SMZ[c] | 15 | 41 | 5 | 8.3 | 46 | 5 | 9.2 |
| Ciprofloxacin + TMP—SMZ[c] + | 14 | 37 | 5 | 8.1 | 42 | 5 | 9.0 |

[a]Prevalence of resistance (overall and within each listed genotype) was calculated based on the median prevalence of fluoroquinolone (FQ) resistance at the participating VA Medical Centers (29%), the observed proportion of FQ-resistant and FQ-susceptible study isolates that represented ST131 or the H30 ST131 subclone (FIG. 1), and the observed prevalence of each resistance phenotype within these subgroups.
[b]Hazard ratio: resistance prevalence among ST131 isolates relative to all other isolates, or among H30 ST131 subclone isolates relative to all other isolates.
[c]TMP—SMZ, trimethoprim-sulfamethoxazole.
[d]MDR, multi-drug resistance to ≥3 or ≥5 drug classes.

ST131 was broadly distributed geographically and exhibited consistent associations with FQ resistance and ESBL production. Among FQ-S isolates ST131 was identified at only 13 VAMCs, and accounted for only 10-20% of FQ-S isolates per VAMC. In contrast, among FQ-R isolates ST131 was identified at all 24 VAMCs, and accounted for 50-100% of FQ-R isolates per VAMC. Similarly, among ESBL isolates ST131 was encountered at each VAMC that provided ≥3 ESBL isolates, and accounted for 33-100% of ESBL isolates per VAMC.

ST131 was similarly prevalent across the four major U.S. census regions among the FQ-S and FQ-R isolates. In contrast, among ESBL isolates its prevalence was significantly lower in the Midwest region, at 37.2%, than in other census regions, which had ST131 prevalence values of 74-84%.

Specimen type was documented for 545 (92%) isolates and included urine (85%), bloodstream (7%), and miscellaneous (8%: 1.8% respiratory, 1.7% wound, <0.8% each for 12 others). Inpatient vs. outpatient source was documented for 414 (70%) isolates, with 304 (73.4%) being from outpatients. ST131 did not vary significantly in prevalence by either variable (not shown).

Example 26. Prevalence of STs

Figure 16:
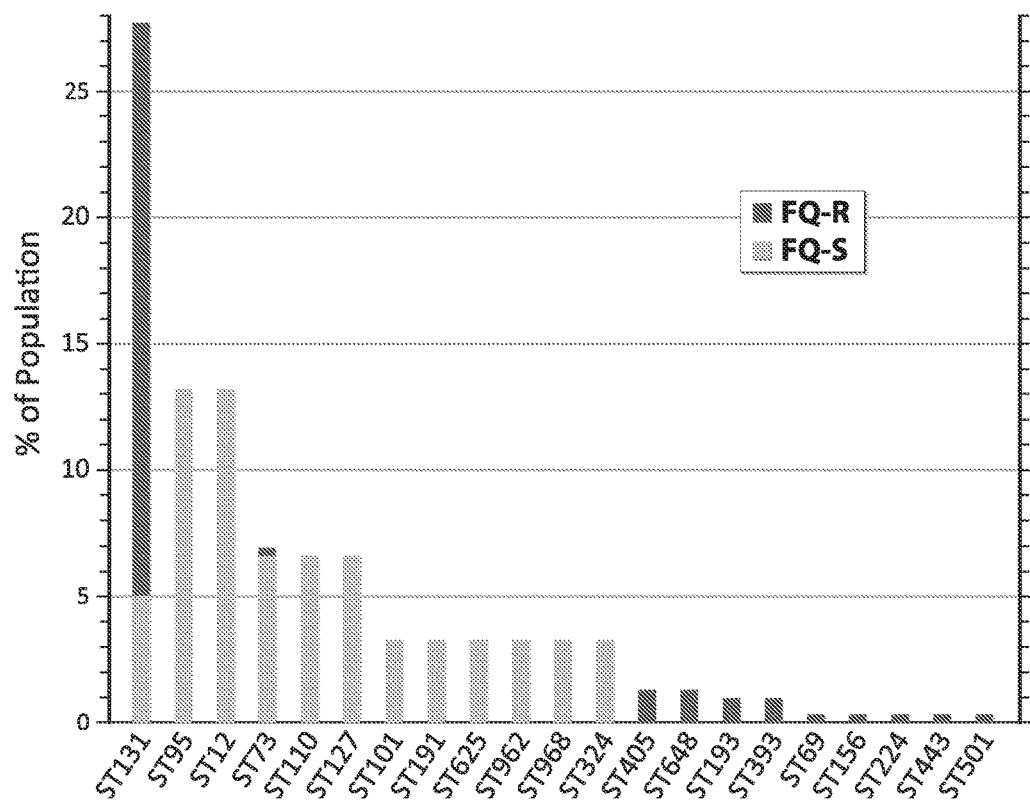
FIG. 16 shows the overall population prevalence of ST131 and other sequence types (STs) among Escherichia coli clinical isolates from veterans.

Based on ST131's proportional contribution to the FQ-R and FQ-S subgroups, plus the respective sizes of these subgroups, ST131 was estimated to account for 27.7% of all VAMC *E. coli* isolates nationwide. Seven-locus MLST of a randomly selected subset of 20 each FQ-S and FQ-R non-ST131 isolates identified a diversity of STs within each resistance group, with minimal overlap across groups. According to back-calculations for total population prevalence, in descending order the most prevalent non-ST131 STs contributing FQ-S isolates were ST95, ST12, ST73, ST10, and ST127 (6.6%-13.2% prevalence each), whereas the most prevalent contributing FQ-R isolates were ST405, ST1193, ST648, and ST393 (0.9%-1.3% prevalence each). Therefore, ST131 was by far the most prevalent ST overall (27.7% total prevalence), far outnumbering the next-most-prevalent STs, ST95 and ST12 (13.2% each) (FIG. 16). Based on similar calculations, the overall prevalence of the H30 ST131 sub-clone was estimated at 22.8%, more than 3-fold greater than the next-most prevalent fimH-based CH sub-clones, 38-18 and 38-41 (from ST95: 6.6% each).

FIG. 16 presents the overall population prevalence of ST131 and other sequence types (STs) among *Escherichia coli* clinical isolates from veterans. The 19 most prevalent STs are shown. Estimated overall prevalence was calculated based on subsamples. FQ-R and FQ-S, fluoroquinolone-resistant and fluoroquinolone-susceptible. Nearly all FQ-R ST131 isolates represented the fimH30 ST131 subclone.

Example 27. PFGE Analysis

Figure 17:
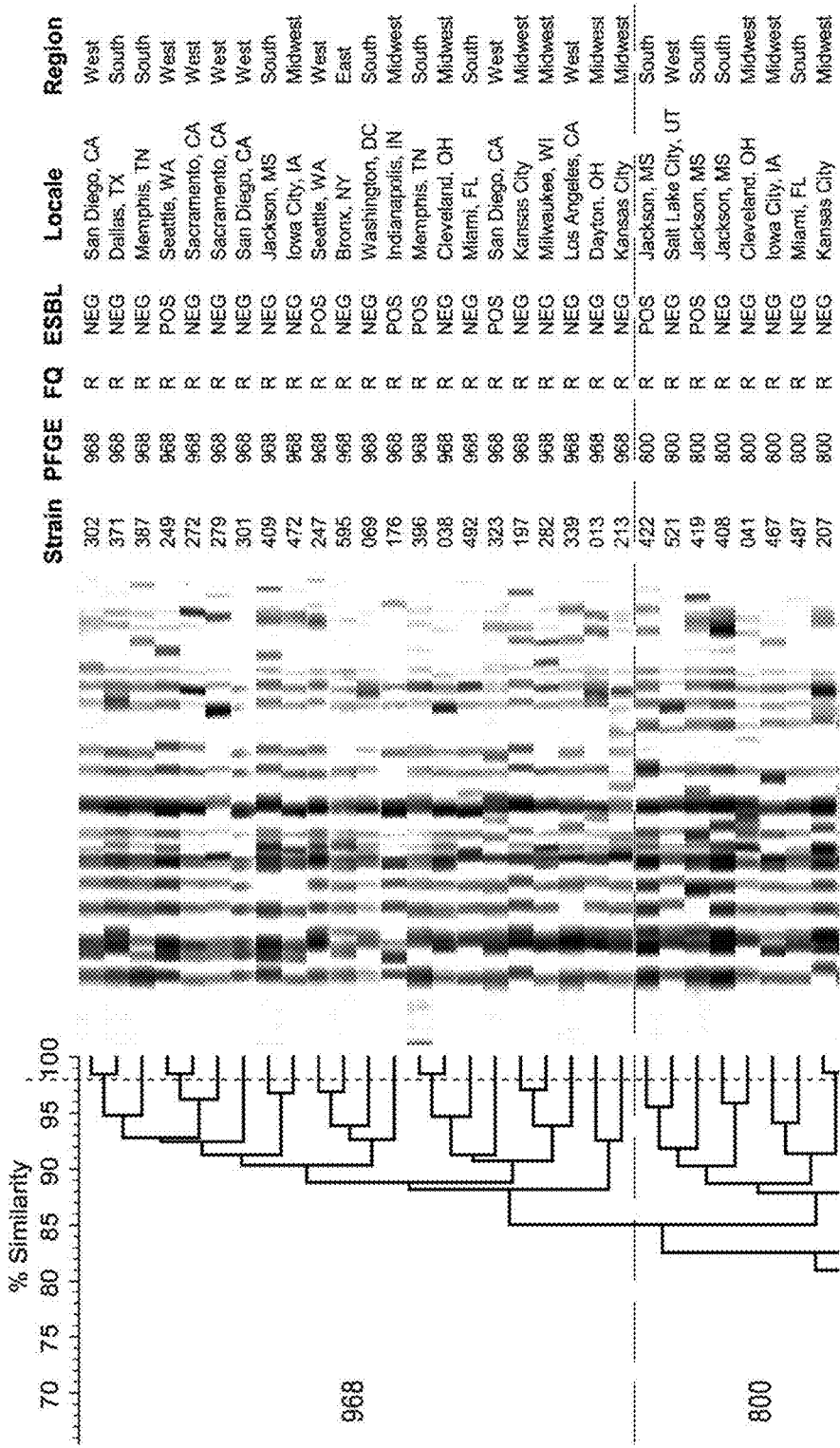
FIG. 17 shows XbaI pulsed-field gel electrophoresis-based dendrogram for 85 ST131 Escherichia coli isolates from veterans.

XbaI PFGE analysis of 85 randomly selected ST131 isolates (FIG. 17) showed a predominance of pulsotypes 968 (26%), 800 (12%), and 812 (4%), as in a recent global survey of ST131 isolates (Johnson J R, Nicolas-Chanoine M H, DebRoy C, et al. Comparison of *Escherichia coli* ST131 pulsotypes, by epidemiologic traits, 1967-2009. Emerg Infect Dis 2012; 18(4): 598-607). Pulsotypes were distributed broadly across VAMCs and census regions. Of the seven profile clusters with ≥98% similarity (2 isolates each), four comprised isolates from widely separated VAMCs.

Example 28. Virulence Genes

Figure 18:
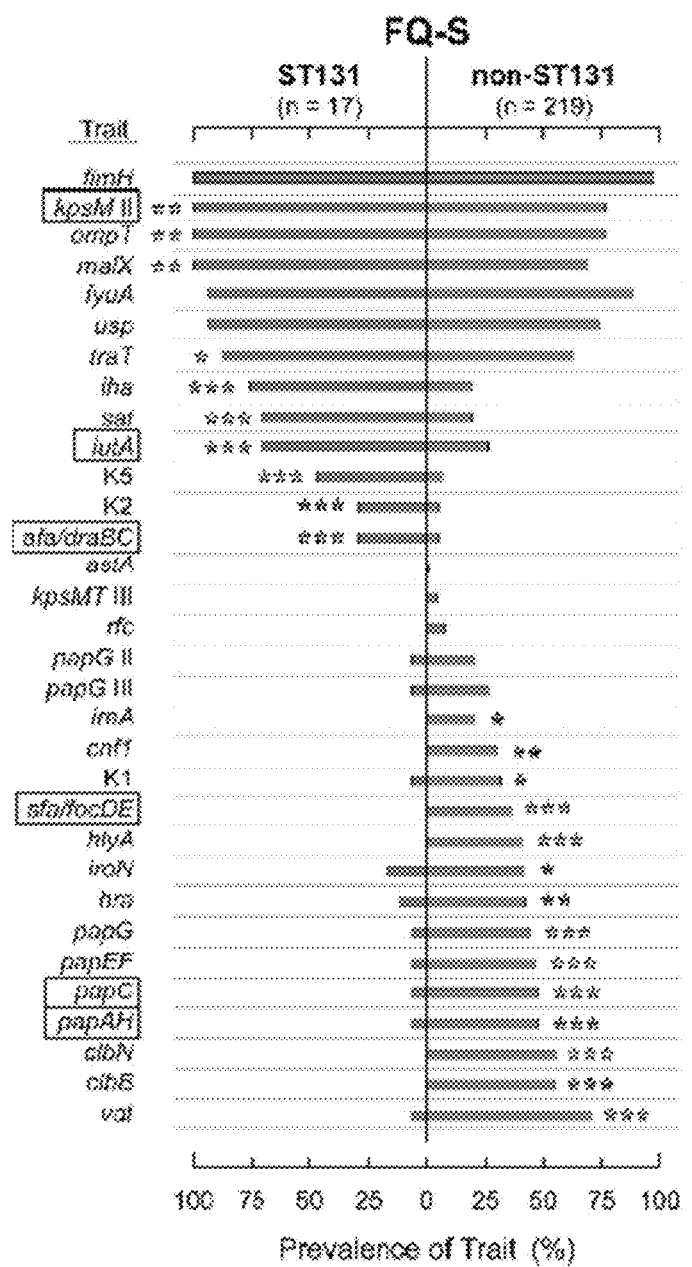
FIG. 18 shows virulence genotypes of 595 Escherichia coli isolates in relation to ST131 genotype, by antimicrobial resistance group.

Virulence traits were assessed as a possible contributor to ST131's high prevalence. Of the studied virulence genes, 57% (31/54) varied significantly in prevalence with ST131 genotype in one or more resistance group (FIG. 18). ST131-associated virulence genes included certain adhesins (afa/dra, iha, fimH), a toxin (sat), siderophore receptors (iutA, fyuA), capsule variants (kpsMT II, K2, K5), and miscellaneous traits (usp, ompT, traT, and malX). Non-ST131-associated genes included other adhesins (papAHCEFG, papG alleles I and II, sfa/focDE), toxins (hlyA, cnf1, hlyF, pic, vat, astA), siderophore receptors (iroN, ireA), protectins (K1 capsule, O4 lipopolysaccharide [rfc]), and microcins/colibactins (clbB, clbN, cvaC).

Virulence profiles among ST131 isolates were fairly consistent across resistance groups, but among non-ST131 isolates varied greatly by resistance group, being much sparser among FQ-R and ESBL isolates than FQ-S isolates (FIG. 18). Within each resistance group a significantly greater proportion of ST131 than non-ST131 isolates qualified molecularly as ExPEC (FQ-S, 83% vs. 57%: P=0.04; FQ-R, 54% vs. 35%: P=0.012; ESBL, 85% vs. 27%: P<0.001). Among FQ-S isolates VF scores were similarly high regardless of ST131 genotype (FIG. 19). In contrast, among FQ-R and ESBL isolates VF scores were much higher among ST131 isolates than non-ST131 isolates.

FIG. 18 presents the virulence genotypes of 595 *Escherichia coli* isolates in relation to ST131 genotype, by antimicrobial resistance group. FQ-R and FQ-S, fluoroquinolone-resistant and fluoroquinolone-susceptible. ESBL, extended-spectrum beta-lactamase. Traits shown are those (among 54 total) that yielded P<0.05 for comparisons of ST131 (pink bars) vs. non-ST131 (blue bars) isolates in at least one resistance group. Traits are arranged, from top to bottom, in order of descending prevalence among the FQ-S ST131 isolates (if positively associated with ST131), then ascending prevalence among the FQ-S non-ST131 isolates (if negatively associated with ST131). P value symbols are shown adjacent to the higher prevalence group when P<0.05, and are as follows: *P<0.05, P<0.01, *P<0.001. Rectangles enclose traits contributing to molecular definition of extraintestinal pathogenic *E. coli* (ExPEC). Trait definitions: afa/draBC, Dr-family adhesins; clbB and clbN, colibactin synthesis; cnf1, cytotoxic necrotizing factor; fimH, type 1 fimbriae; fyuA, yersiniabactin receptor; hlyA, □ hemolysin; hra, heat-resistant agglutinin; iha, adhesin-siderophore; ireA, siderophore receptor; iroN, salmochelin receptor; iutA, aerobactin receptor; kpsM II, group 2 capsule; K1, K2, and K5, group 2 capsule variants; malX, pathogenicity island marker; ompT, outer membrane protease T; papA, papC, papEF, and papG, P fimbrial structural subunit, assembly, tip pilins, and adhesin, respectively; papG allele II, P adhesin variant; sat, secreted autotransporter toxin; sfa/foc, S or F1C fimbriae; traT, serum resistance-associated; usp, uropathogenic-specific protein; vat, vacuolating toxin.

FIG. 19 presents the virulence and resistance scores among ST131 and non-ST131 *Escherichia coli* isolates within three resistance groups. FQ-R and FQ-S, fluoroquinolone-resistant and fluoroquinolone-susceptible. ESBL, extended-spectrum beta-lactamase. Box-whisker plots show group medians (heavy horizontal bar), 25th and 75th percentiles (bottom and top of boxes, respectively), and maximum and minimum values (light horizontal bars). P values, as determined by the Mann-Whitney U test (2-tailed), are shown for ST131 vs. non-ST131 comparisons when P<0.05.

(Left panel) Virulence scores (number of distinct virulence genes) among ST131 versus non-ST131 isolates within each resistance group. (Right panel) Resistance scores (number of resistance markers detected) among ST131 isolates versus on-ST131 isolates within each resistance group.

Example 29. Antimicrobial Resistance

Figure 20:
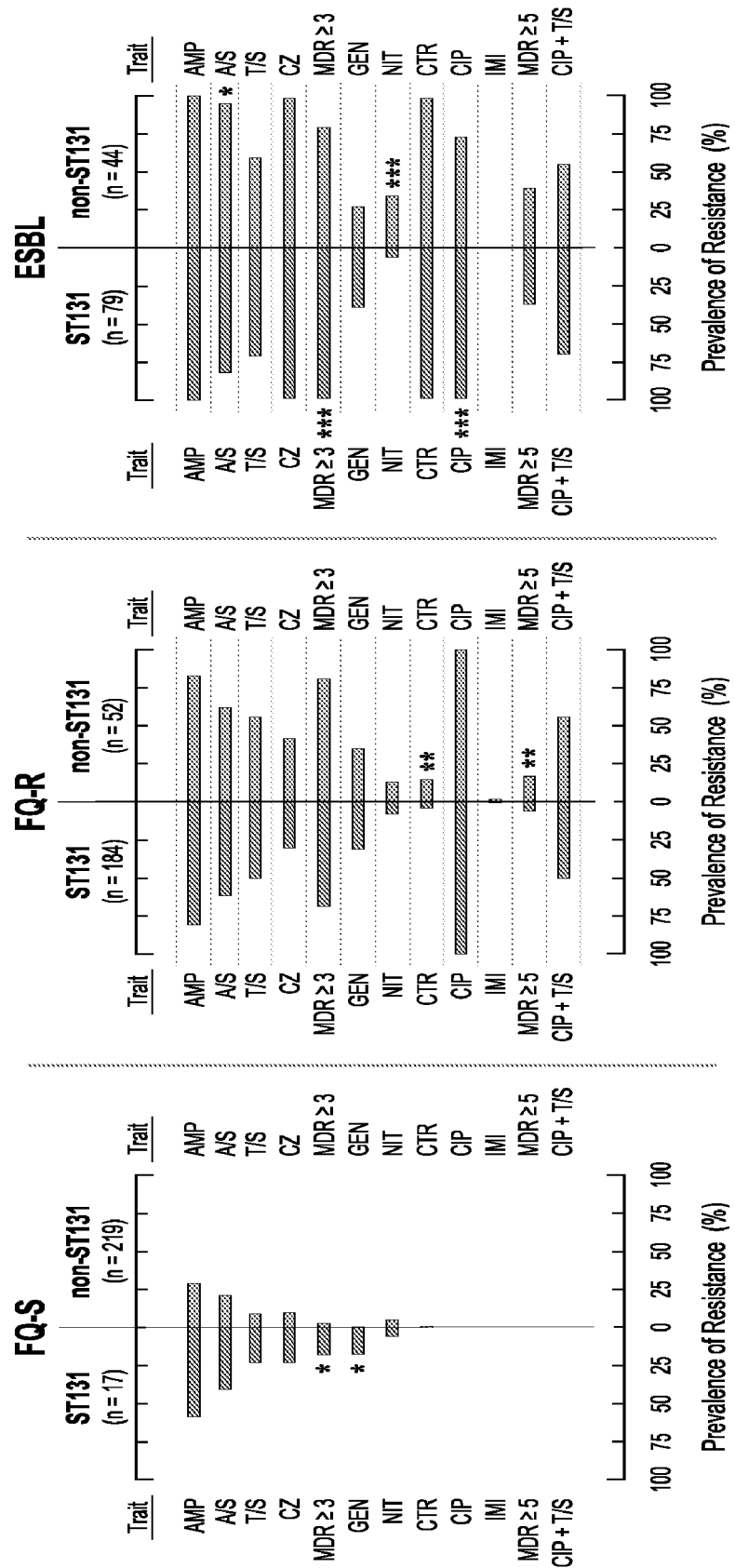
FIG. 20 shows antimicrobial resistance prevalence among 595 E. coli isolates according to ST131 status and resistance group.

Resistance to the studied antimicrobial agents, both individually and combined, varied greatly in prevalence by agent and resistance group, but minimally by ST131 genotype (FIG. 20). Paralleling these trends, aggregate resistance scores increased progressively by resistance group, from FQ-S, through FQ-R, to ESBL isolates (FIG. 19). Within a given resistance group the ST131 isolates had similarly high (FQ-R and ESBL group) or slightly but significantly higher (FQ-S group) scores compared with non-ST131 isolates.

FIG. 20 presents the antimicrobial resistance prevalence among 595 E. coli isolates according to ST131 status and resistance group. FQ-R and FQ-S, fluoroquinolone-resistant and fluoroquinolone-susceptible. P value symbols (from the Mann-Whitney U test) for comparison of ST131 (red bars) vs. non-ST131 (blue bars) isolates within each resistance group, which are shown next to the higher prevalence group if $P<0.05$, are as follows: *$P<0.05$, $P\leq0.01$, *$P\leq0.001$. Resistance trait abbreviations: AMP, ampicillin; A/S, ampicillin-sulbactam; CZ, cefazolin; CTR, ceftriaxone; CIP, ciprofloxacin; GEN, gentamicin; IMI, imipenem; MDR, multidrug resistance (to $\geq3$ or $\geq5$ drug classes); NIT, nitrofurantoin; T/S, trimethoprim-sulfamethoxazole.

Back-calculations suggested that ST131's overall contribution to antimicrobial resistance within the source E. coli population was $\geq40\%$ for each beta-lactam agent, $>50\%$ for TMP-SMZ resistance and multidrug resistance, and $>70\%$ for ciprofloxacin, gentamicin, and combined ciprofloxacin plus TMP-SMZ (or combined ciprofloxacin, TMP-SMZ, and ampicillin) resistance (Table 17).

The estimated overall prevalence of each resistance phenotype (Table 18) was consistently greater among the ST131 and H30 sub-clone isolates than other isolates (median hazard ratios, 3.2-3.4; range, 1.3-9.3). The stratified resistance prevalence values for ST131 or H30 subclone isolates vs. other isolates often straddled a prevalence threshold (e.g., 10%, 15%, 20%) commonly used for selecting empirical antimicrobial therapy (Table 18).

We screened for the ST131 clonal group and its H1130 sub-clone among 595 E. coli clinical isolates, collected systematically in 2011 from 24 VAMCs distributed widely across the US. We found that ST131 was ubiquitous and highly prevalent, especially among antimicrobial-resistant isolates, and differed from other E. coli according to its phylogenetic group B2 background, high prevalence of recognized virulence trait genes, and extensive antimicrobial resistance capabilities. These findings newly identify ST131 and its H30 sub-clone as extremely important pathogens among veterans, which has significant implications for the prevention, diagnosis, and management of E. coli infections in the VA population.

ST131 accounted for only 7.2% of FQ-S isolates, but for a striking 78% of FQ-R isolates and 64.2% of ESBL isolates. Moreover, since the median prevalence of FQ resistance in E. coli at the participating VAMCs was 29%, ST131 presumably accounted for approximately 28% of all clinical E. coli isolates at these VAMCs. These high prevalence values for ST131 exceed those from the most recent general surveys, which have been as high as 17%, 22%, 23% and 27% for overall prevalence, and 24.8%, 52%, and 69% for prevalence among FQ-R isolates. Possible explanations for this finding include further emergence of ST131 since the previous studies, or geographical or host population differences.

Evidence against further emergence and geographical differences is provided by analysis of national surveillance isolates from the SENTRY program, showing that ST131's prevalence in the general U.S. population was similar in 2011 (unpublished, J.R.J.) compared to 2007. Evidence favoring host population differences is that veterans receiving care at VAMCs tend to be elderly men, often with multiple comorbidities and extensive antimicrobial. Older age, antimicrobial use, and health care contact have been identified as risk factors for ST131 infection. Therefore, the VAMC patient population may be especially susceptible to ST131.

In contrast to the ST131 isolates, the non-ST131 isolates were divided amongst multiple STs, none of which contributed more than 13.2% to the total population. Therefore, ST131 was by far the most prevalent clonal group among veterans, with an estimated 28% overall prevalence, exceeding the next-most-prevalent STs by >2-fold. Although several recent studies identified ST131 as the first or second most prevalent clonal group within collections of all E. coli clinical isolates from specific regions, none documented such a great gap between ST131 and traditional high-prevalence ExPEC clonal groups such as ST95, ST73, ST12, and ST127.

Notably, most of the present ST131 isolates, including nearly all within the FQ-R and ESBL groups, represented the H30 ST131 sub-clone, which was recently shown to have a single-strain origin and to account for most FQ-R ST131 isolates, regardless of source and locale. Therefore, this single, remarkably successful sub-clone within ST131 has achieved dominance within the veteran-associated E. coli population, especially the antimicrobial-resistant subset.

ST131 was distributed fairly uniformly across the 24 VAMCs, geographical regions, specimen types, and inpatient vs. outpatient settings. The ubiquity of ST131 among U.S. veterans indicates that the study's findings likely are applicable throughout the VA Health Care system, and in similar non-veteran populations. In this regard, the occurrence across VAMCs of ST131-associated pulsotypes that are common also in the general population suggests ongoing transmission of ST131 among VAMCs and between veterans and non-veterans, and that similar risk factors and transmission pathways for ST131 may apply in veteran and non-veteran populations.

As possible explanations for ST131's emergence and predominance, compared with other E. coli the ST131 isolates more frequently represented phylogenetic group B2, had more extensive virulence genotypes and/or antimicrobial resistance profiles, and more commonly qualified molecularly as ExPEC. This implies that, in ST131, antimicrobial resistance has combined with extraintestinal virulence to an extent not observed previously in E. coli, thereby creating a proverbial "superbug". Although in vivo evidence for hyper-virulence in ST131 from animal models is lacking, such models may not reflect the human situation. Indeed, recent epidemiological data document a prevalence gradient of ST131 in relation to clinical severity, from fecal isolates (low), through cystitis isolates (intermediate), to pyelonephritis isolates (high), implying enhanced clinical virulence for ST131.

Finally, according to back-calculations ST131 accounted for a majority of antimicrobial resistance among clinical isolates, particularly for certain individual agents (FQs, 78%; TMP-SMZ, 56%; gentamicin, 76%), combined TMP-SMZ plus FQ resistance (52%), and multi-drug resistance (≥3 classes, 70%; ≥5 classes, 55%). Therefore, problematical antimicrobial-resistant E. coli infections among veterans are caused predominantly by ST131 and, specifically, its H30 sub-clone, indicating that clonal spread dominates over both horizontal transfer of resistance elements and de novo mutation to resistance in driving the current E. coli resistance epidemic.

These findings have important practical implications. First, given ST131s high overall prevalence and major contribution to antimicrobial-resistant E. coli infections, focused attention to ST131 conceivably could yield substantial reductions in morbidity and costs within the VA health care system. Secondly, given the ubiquity of ST131, such measures should be applicable broadly across VAMCs. They could include preventive interventions (e.g., vaccines or probiotics), infection control strategies (analogous to the current VA-wide screening for methicillin-resistant Staphylococcus aureus colonization), and rapid detection, especially of the H30 sub-clone. Rapid detection could be particularly useful in selecting empirical therapy, since for many agents the ST131 and H30 sub-clone isolates exhibited resistance prevalence values exceeding typical empirical therapy thresholds of 10%, 15%, or 20%, with other isolates falling below these thresholds. Third, a fuller elucidation of why ST131 rose to such striking prominence could provide novel insights into the emergence of new resistant and virulent pathogens generally, thereby enabling more effective responses to future epidemic "superbugs". Ongoing surveillance for such emergent pathogens is needed, to provide an early warning when a new successful lineage begins to expand.

In summary, we documented an impressively high prevalence of ST131 and its fimH30 sub-clone among clinical E. coli isolates from U.S. veterans in 2011. ST131 accounted for more antimicrobial resistance (especially to FQs, TMP-SMZ, gentamicin, and multiple drug classes), and exhibited greater molecularly inferred virulence, than did other E. coli. Focused attention to ST131 and its H30 sub-clone could help reduce infection-related morbidity, mortality, and health care costs among veterans.

Example 30. Experimental Methods

The following experimental methods were used for the analyses discussed in Examples 31-33.

Specimen Collection

As reported elsewhere, the 267 E. coli study isolates were collected between 2007 and 2010 as part of a prospective case-control study conducted at NorthShore University HealthSystem (Banerjee, R J et al. "Predictors and molecular epidemiology of community-onset extended-spectrum beta-lactamase (ESBL) Escherichia coli infection in a Midwestern community," 2013 Infect Control Hosp Epidemiol; in press). Cases were defined as adults with ESBL-producing E. coli cultured from any specimen type. Controls were defined as the 1 or 2 patients with non-ESBL E. coli isolates identified just subsequent to the case isolate, and with the same specimen type and location of collection. Isolates obtained in the outpatient setting or within 48 hours of hospital admission were considered causes of community-associated infection. Further study details are as described (Banerjee, R J et al. "Predictors and molecular epidemiology of community-onset extended-spectrum beta-lactamase (ESBL) Escherichia coli infection in a Midwestern community," 2013 Infect Control Hosp Epidemiol; in press).

Antimicrobial susceptibility was determined using broth microdilution (for all antimicrobials) and disk diffusion (for ESBL phenotype confirmation) using Clinical and Laboratory Standards Institute interpretive criteria (Institute, C. a. L. S. 2009. Performance standards for antimicrobial susceptibility testing; nineteeth informational supplement (M100-S19). Clinical and Laboratory Standards Institute, Wayne, Pa.) Isolates testing as resistant or intermediate to a given antimicrobial were considered resistant. The resistance score was the total number of agents to which an isolate was resistant. This study was approved by the NorthShore and VA Medical Center institutional review boards.

Molecular Characterization

Major E. coli phylogenetic group (A, B1, B2, and D) and presence of the O25b rfb variant were determined by PCR as described (Clermont, O et al. 2000 Appl Environ Microbiol 66:4555-4558; Clermont, O et al. 2007 Diagn Microbiol Infect Dis 57:129-136; Johnson, J R, et al. Clin Infect Dis. (2010) 51(3): 286-294). ST131 and its H30 subclone were identified by PCR-based detection of clonal group-specific single-nucleotide polymorphisms (SNPs) (Johnson, J R, et al. JID 2013; 207:919-928). For the H30-Rx subclone, primers were designed to detect a subclone-specific SNP (ybbW: bp 723: G→A) within the allantoin protein-encoding gene, ybbW. Primers APfor63 (5'-GGTTGCG-GTCTGGGCA-3') (SEQ ID NO: 63) and APrev66 (5'-CAATATCCAGCACGTTCCAGGTG-3') (SEQ ID NO: 64) were used with the following cycling routine (95° C. for 8 minutes; 31 cycles of [94° C. for 20 sec and 72° C. for 40 seconds]; final extension at 72° C. for 5 minutes) to give a 194-bp amplicon. Assay accuracy was confirmed by testing 7 known positive controls and 9 known negative controls, as defined based on whole genome analysis (submitted), all of which yielded the expected results. In addition, from the present study population 5 each randomly selected putative H30-Rx and non-H30-Rx ST131 isolates, based on the above PCR assay, underwent sequence analysis of amplicons spanning the H30-Rx-defining SNP within ybbW. In each instance, this confirmed the presence/absence of this SNP in precise agreement with SNP-based PCR.

ESBL phenotype testing was performed by disk diffusion according to guidelines of the Clinical and Laboratory Standards Institute (Institute, C. a. L. S. 2009. Performance standards for antimicrobial susceptibility testing; nineteeth informational supplement (M100-S19). Clinical and Laboratory Standards Institute, Wayne, Pa.). Major CTX-M groups were identified using multiplex PCR (Xu, L et al. 2005 J Med Microbiol 54:1183-1187). $bla_{CTX-M-15}$-specific PCR was used to detect CTX-M-15 among the group 1 CTX-M-type ESBLs (Johnson, J R, et al. Antimicrob. Agents Chemother. 2012; 56(5):2364-2370); group 9 CTX-M-type ESBLs were not further differentiated.

Fifty ExPEC-associated VF genes were detected using established multiplex PCR methods (Johnson, J R, et al. Clin Infect Dis. (2010) 51(3): 286-294; Johnson, J et al. 2009 Antimicrob Agents Chemother 53:2733-2739; Johnson, J et al. 2000 J Infect. Dis. 181:261-272). The virulence score was the total number of virulence genes detected, adjusted for multiple detection of the pap (P fimbriae), sfa/foc (S and F1C fimbriae), and kps II (group2 capsule) operons. Isolates were classified as ExPEC if positive for ≥2 of the following genes: papA and/or papC (P fimbriae structural subunit and assembly), sfa/foc, afa/dra (Dr-binding adhesins), kpsM II, and iutA (aerobactin receptor) (Johnson, J R, et al. Antimicrob. Agents Chemother. 2003; 47(7):2161-2168).

Statistical Analysis

Proportions were compared using Fischer's exact test. Continuous variables were compared using the Mann-Whitney U test. P<0.05 was considered statistically significant. Principal coordinates analysis (PCoA), a multidimensional scaling method analogous to principle components analysis, was used to collapse the molecular dataset for simplified between-group comparisons (Peakall, R et al. 2006 Mol Ecol Notes 6:288-295). Groups were compared on each of the first 3 coordinates, which capture most of the variance within the dataset, using a 2-tailed t test (Johnson, J R, et al. Clin Infect Dis. (2010) 51(3): 286-294).

Example 31. Prevalence of ST131, Phylogenetic Groups, and ESBL Types

The 267 *E. coli* study isolates, which were predominantly from urine (92%) and community-associated infections (95%), included 100 ESBL-positive (case) isolates and 167 ESBL-negative (control) isolates. ST131 accounted for a much greater proportion of ESBL-positive (49%) than ESBL-negative isolates (13%) (Table 19). Since the ST131 isolates were overwhelmingly O25b-positive, whether ESBL-positive or negative, the high prevalence of ST131 among the ESBL isolates gave a much higher prevalence of O25b among the ESBL-positive than ESBL-negative isolates.

Group B2 was the most common phylogenetic group, both overall and among ESBL-positive and ESBL-negative isolates. However, this varied in relation to ST131 status. That is, whereas among ESBL-negative isolates group B2 predominated even among non-isolates, among ESBL-positive isolates most non-ST131 isolates were from groups A and D, with only a small minority being from group B2 (Table 19).

The most prevalent ESBL type among the ESBL isolates, whether ST131 or non-ST131, was CTX-M. The CTX-M-15 variant dominated (73%), followed by group 9 CTX-M variants (11%). Trends associating CTX-M-15 with ST131 were non-significant.

Example 32. Prevalence and Characteristics of the H30 and H30-Rx ST131 Subclones Among the 49 ESBL-positive ST131 isolates, 48 (98%) belonged to the H30 ST131 subclone, with 44 (92%) of these representing the H30-Rx subclone. In contrast, among the 22 ESBL-negative ST131 isolates, much smaller proportions belonged to the H30 subclone (14, 64%) and H30-Rx subclone (3, 14%); another group (11, 50%) were non-H30 isolates.

H30 ST131 subclone isolates were overwhelmingly fluoroquinolone-resistant (98%) and ESBL producers (77%), as compared with small minorities of non-H30 ST131 isolates (36% and 11%, respectively) (FIG. 21A). Furthermore, within the H30 subclone, ESBL prevalence and subtype varied significantly with H30-Rx status. That is, 94% of H30-Rx isolates, but only 27% of other H30 isolates, were ESBL producers (FIG. 21B), and the corresponding ESBLs were all CTX-M-15 (H30-Rx) vs. CTX-M-9 (other H30 isolates). In contrast, the few non-H30 subclone isolates that were ESBL-positive produced non-CTX-M ESBLs (FIG. 21A).

Example 32. Antimicrobial Resistance to ESBL and ST131 Isolates

When compared with ESBL-negative isolates, ESBL-positive isolates had a significantly higher prevalence of resistance to each tested antimicrobial agent (Table 20), and significantly higher aggregate resistance scores (median 6 vs. 0: P<0.001). Resistance also varied significantly in relation to ST131 status, but in opposite directions within the two ESBL subsets. That is, among ESBL-positive isolates, resistance scores were subtly but significantly lower among ST131 isolates than non-ST131 isolates (median 6 vs. 6: p=0.002). In contrast, among ESBL-negative isolates, resistance scores were substantially greater among ST131 isolates (median, 3 vs. 0: p<0.001).

Among the ST131 isolates, the H30 subclone isolates, as compared to the non-H30 isolates, had a higher prevalence of resistance to beta-lactams and ciprofloxacin (Table 21) and higher resistance scores (median, 5 vs. 3: p<0.001). Similarly, within the H30 ST131 subclone, the H30-Rx isolates, as compared to other H30 isolates, had a higher

TABLE 19

Characteristics of 267 *Escherichia* clinical isolates in relation to ESBL phenotype and ST131 status.

| | | Prevalence of trait, no. of isolates (column %) | | | | | |
|---|---|---|---|---|---|---|---|
| | | ESBL-positive | | | ESBL-negative | | |
| | | | | Non- | | | |
| Trait category | Specific trait | Total (N = 100) | ST131 (N = 49) | ST131 (N = 51) | Total (N = 167) | ST131 (N = 22) | Non-ST131 (N = 145) |
| Phylo. group | A | 17 (7) | 0 | 17 (33) | 15 (9) | 0 | 15 (10) |
| | B1 | 3 (3) | 0 | 3 (6) | 11 (7) | 0 | 11 (8) |
| | B2 | 54 (54) | 49 (100) | 5 (10) | 100 (60) | 22 (100) | 88 (61) |
| | D | 26 (26) | 0 | 26 (51) | 31 (19) | 0 | 31 (21) |
| O25b | NA | 49 (490) | 49 (100) | 0 | 23 (14) | 19 (86) | 4 (3) |
| ExPEC | NA | 60 (60) | 41 (84) | 19 (37) | 126 (75) | 14 (64) | 102 (70) |
| ESBL type | CTX-M-15 | 73 (73) | 40 (82) | 33 (65) | NA | NA | NA |
| | Gp. 9 CTX-M | 11 (11) | 4 (8) | 7 (14) | NA | NA | NA |
| | Non-CTX-M | 16 (16) | 5 (10) | 11 (22) | NA | NA | NA | prevalence of resistance to cephalosporins (Table 21) and higher resistance scores (6 vs. 3, p=0.01).

TABLE 20

Antimicrobial resistance of 267 ESBL-positive and negative *Escherichia coli* isolates by ST131 status.

| | ESBL[a]-positive isolates | | | | ESBL[a]-negative isolates | | | |
|---|---|---|---|---|---|---|---|---|
| | No. resistant (column %) | | | | No. resistant (column %) | | | |
| Anti-microbial[b] | All (N = 100) | ST131 (N = 49) | Non-ST131 (N = 51) | P value[c] | All (N = 167) | ST131 (N = 22) | Non-ST131 (N = 145) | P value[c] |
| Ampicillin | 100 (100) | 49 (100) | 51 (100) | | 73 (44) | 19 (86) | 54 (37) | <.001 |
| Cefazolin | 99 (99) | 48 (98) | 51 (100) | | 10 (6) | 1 (5) | 9 (6) | |
| Ceftriaxone | 98 (98) | 47 (96) | 51 (100) | | 1 (1) | 0 (0) | 1 (1) | |
| Ceftazidime | 92 (92) | 45 (92) | 47 (92) | | 1 (1) | 0 (0) | 1 (1) | |
| Gentamicin | 48 (48) | 18 (37) | 30 (59) | .03 | 12 (7) | 10 (45) | 2 (1) | <.001 |
| Ciprofloxacin | 95 (95) | 48 (98) | 47 (92) | | 24 (15) | 15 (68) | 9 (6) | <.001 |
| TMP—SMZ | 63 (63) | 24 (49) | 39 (76) | .007 | 31 (19) | 13 (59) | 18 (12) | <.001 |

[a]ESBL, extended spectrum beta-lactamase
[b]All isolates (N = 183) tested against carbapenems were susceptible
[c]P values (by Fisher's exact test, for comparisons of ST131 vs. non-ST131 isolates within a given ESBL-positive or negative group) are shown where P < .05. For all other comparisons, P > .10.
[d]TMP—SMZ, trimethoprim-sulfamethoxazole

TABLE 21

Antimicrobial resistance by sT13 1 subclone among 71 *Escherichia coli* ST131 isolates.

| | No. of resistant isolates (column %) | | | No. of resistant isolates (column %) | | |
|---|---|---|---|---|---|---|
| Anti-microbial | H30 (N = 62) | Non-H30 (N = 9) | P value, H30 vs. non-H30 | H30-Rx (N = 47) | H30, non-Rx (N = 15) | P value, H30-Rx vs. H30 non-Rx |
| Ampicillin | 61 (98) | 7 (78) | .04 | 46 (98) | 15 (100) | |
| Cefazolin | 48 (77) | 1 (11) | <.001 | 43 (91) | 5 (33) | <.001 |
| Ceftriaxone | 46 (74) | 1 (11) | <.001 | 42 (89) | 4 (27) | <.001 |
| Ceftazidime | 44 (71) | 1 (11) | .001 | 40 (85) | 4 (27) | <.001 |
| Gentamicin | 23 (37) | 5 (56) | | 15 (32) | 8 (53) | |
| Ciprofloxacin | 61 (98) | 2 (22) | <.001 | 46 (98) | 15 (100) | |
| TMP—SMZ | 31 (50) | 6 (67) | | 21 (45) | 10 (67) | |

Note:
TMP—SMZ, trimethoprim-sulfamethoxazole. P values (by Fisher's exact test) are shown where P < .05. For all other comparisons, P > .10.

Example 33. Virulence Gene Profiles

Virulence factor gene distribution varied significantly in relation to both ESBL phenotype and ST131 genotype (Supplemental table 1). Overall, nearly all VF genes that were significantly associated with ESBL status were more prevalent among ESBL-negative isolates; only iha, sat, iutA, traT, and malX were more prevalent among ESBL-positive isolates. Additionally, within the ESBL-positive and negative groups, many VF genes differed significantly in prevalence between the ST131 and non-ST131 isolates. The consensus VF gene profile (>90% prevalence) of the ST131 isolates (ESBL-positive and negative alike) included fimH, fyuA, usp, ompT, and malX. Additionally, >90% of ESBL-positive ST131 isolates also contained iha, sat, kpsM II, and traT.

The proportion of all isolates qualifying as ExPEC was similar among ESBL-positive and ESBL-negative isolates (60% vs. 67%), and, among ESBL-negative isolates, did not differ by ST131 status. However, among ESBL-positive isolates, a significantly greater proportion of ST131 than non-ST131 isolates qualified as ExPEC (85% vs. 37%, P<0.001) (Table 19).

Virulence scores were significantly lower overall among ESBL-positive isolates compared to ESBL-negative isolates (median, 9 vs. 11: p<0.001). This was due entirely to the non-ST131 isolates, among which, for ESBL-positive vs. ESBL-negative isolates, the median virulence score was 6 vs. 12 (p<0.001), whereas ST131 isolates had similar scores (median, 10) regardless of ESBL status. Within the ESBL-positive group, virulence scores were much greater among ST131 isolates than non-ST131 isolates (median, 10 vs 6: p<0.001). In contrast, within the ESBL-negative group, virulence scores were slightly but significantly lower among ST131 isolates than non-ST131 isolates (median, 10 vs. 12: p=0.03).

Within ST131, the prevalence of several VF genes differed significantly by H30 subclone status, with iha, sat, and iutA being more prevalent among H30 than non-H30 subclone isolates, but iroN, K1, and ibeA being more prevalent among non-H30 isolates (Table 22). In contrast, within the H30 subclone, only two protectin genes, kpsM II and its K5 variant, differed in prevalence between the H30-Rx and other H30 subclone isolates (Table 21). Virulence scores did not differ significantly by ST131 subclone, being similar among the non-H30, H30, H30-Rx, and other H30 isolates (median for all, 10).

Figure 22:
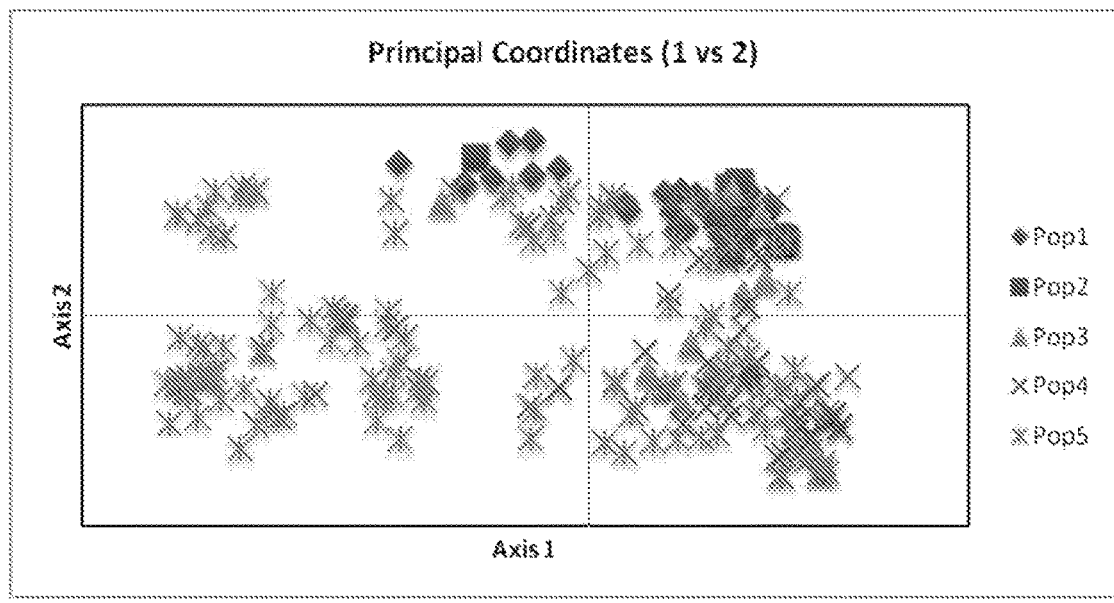
FIG. 22 shows a principal coordinates analysis (PCoA) of virulence gene profiles among 267 Escherichia coli isolates.

Principal coordinate analysis of VF profiles showed that ST131-associated virulence profiles were distinct from those of the non-ST131 isolates, and that within ST131 the three ST131 subclone groups (H30-Rx, other H30, and non-H30) each had characteristic profiles (FIG. 22). The profiles of the H30-Rx isolates were the most homogeneous, whereas those of the non-H30 ST131 isolates were the most diverse, and overlapped most with those of non-ST131 isolates. Among the non-ST131 isolates, the ESBL-negative isolates were distributed quite broadly and were well removed from the ST131 isolates. In contrast, the ESBL-positive non-ST131 isolates were distributed more compactly and in closer proximity to the ST131 isolates (FIG. 22).

In this study we characterized the molecular epidemiology of 267 E. coli clinical isolates collected in 2007-2010 as part of a study regarding risk factors for ESBL-positive E. coli infection in the Chicago, Ill. region. Here, we determined the prevalence of the ST131 clonal group as a whole and of two recently identified subgroups within ST131, i.e., the H30 and H30-Rx subclones, and explored associations of these entities with resistance phenotypes, ESBL types, and virulence profiles.

With ST131 considered as a whole, we confirmed the now well-established association between ST131 and ESBL production, in that ST131 accounted for neary half of ESBL-positive isolates but only 13% of ESBL-negative isolates. At a more discriminating level of clonal analysis, we found that the recently identified H30 subclone within ST131, which has been shown to account for the greatest share of antimicrobial resistance within E. coli, has expanded in the study region to a greater extent than non-H30 ST131 subclones, comprising nearly all ESBL-positive and two-thirds of ESBL-negative ST131 isolates, plus nearly all fluoroquinolone-resistant ST131 isolates.

At an even more discriminating level of clonal analysis, we used a novel SNP-based PCR assay to resolve, among the H30 ST131 isolates, the H30-Rx subclone, a recently evolved sublineage first identified through whole genome sequencing that appears to be the main repository of CTX-M-15 within ST131. Consistent with previous results, we found that within ST131 CTX-M-15 was confined almost exclusively to the H30-Rx subclone, whereas other ESBLs occurred almost exclusively among non-Rx H30 isolates (CTX-M-9 group) or non-H30 isolates (non-CTX-M ESBLs), most of which were ESBL-negative. These findings support that within ST131 $bla_{CTX-M-15}$ is transmitted mainly vertically within the H30-Rx lineage, after what probably was a single ancestral acquisition event, rather than horizontally through multiple gene acquisition events. They also document a continuum of increasingly broad antimicrobial resistance within ST131, from non-H30 isolates (fluoroquinolone and cephalosporin-susceptible), through (non-Rx) H30 isolates (usually fluoroquinolone-resistant but cephalosporin-susceptible), to H30-Rx isolates (usually dually fluoroquinolone and cephalosporin-resistant). In this regard, it is striking that within ST131 both fluoroquinolone and extended-spectrum cephalosporin resistance appear to have a predominantly single-cell origin, the former involving the ancestor of the H30 subclone, the latter the (H30 subclone-derived) ancestor of the H30-Rx subclone Regarding virulence genotypes, we confirmed that among ESBL-positive isolates, ST131 isolates (mostly representing the H30-Rx subclone) have higher virulence scores than non-ST131 isolates, implying greater virulence and possibly contributing to their high prevalence. Moreover, unlike most other studies of ST131 virulence genotypes, ours allowed a comparison of virulence gene profiles among ESBL-positive vs. ESBL-negative ST131 isolates. We found that ESBL-positive ST131 isolates typically contained more virulence genes than did ESBL-negative ST131 isolates. This conflicts with the conventional notion that virulence and resistance are mutually exclusive within E. coli, as does the extensive virulence gene content of ST131 isolates generally. The successful dissemination and expansion of ESBL-positive ST131 strains suggests that carriage of additional virulence and antimicrobial resistance genes is not associated with a significant net fitness cost.

Novel also to this study is the analysis of VF gene profiles associated with subclones within ST131. We identified three VF genes (iha, sat, and iutA) that are more prevalent among H30 than non-H30 ST131 isolates. These genes, which, respectively, encode an adhesin, a toxin, and a siderophore, may contribute to the successful colonization ability, transmissibility, or infectivity of the H30 subclone. We also found the capsule-encoding gene kpsM II, and specifically its K5 variant, to be more common among H30-Rx than other H30 isolates, which supports that these virulence genes, in the H30 genetic background, also may enhance fitness in the commensal and/or pathogenic niche. How specific accessory traits facilitate the epidemiologic success of ST131 and its principal subclones is undefined and deserves further study.

In the study region the H30 subclone of E. coli ST131 has expanded to a greater extent than other subclones and comprises almost half of ESBL-positive E. coli infections. Furthermore, CTX-M-15, the most common ESBL type, is carried almost exclusively by the H30-Rx subset within the H30 ST131 subclone. Within ST131, both the H30 subclone and its H30-Rx variant carry more virulence and antimicrobial-resistance genes than do non-H30 subclones. Elucidation of the molecular and ecologic basis for the success of ST131, especially its H30 and H30-Rx components, are needed to guide the development of interventions against further spread of this highly antimicrobial-resistant clonal group.

TABLE 22

Virulence gene distribution by ST131 subclone among 71 ST131 Escherichia coli isolates.

| Functional category | Specific gene[a] | Gene prevalence within ST131 by H30 subclone status, no. (column %) | | P value[b], H30 vs. non-H30 | Gene prevalence within H30 subclone by H30-Rx status, no. (column %) | | non-P value[b], H30-Rx vs. H30 non-Rx |
|---|---|---|---|---|---|---|---|
| | | H30 (N = 62) | Non-H30 (N = 9) | | H30-Rx (N = 47) | H30, Rx (N = 15) | |
| Adhesin | iha | 60 (97) | 5 (56) | .002 | 45 (96) | 15 (100) | |
| Toxin | sat | 61 (98) | 3 (33) | <.001 | 46 (98) | 15 (100) | |
| Siderophores | iroN | 1 (2) | 2 (22) | .04 | 1 (2) | 0 | |
| | iutA | 56 (90) | 5 (56) | .02 | 42 (89) | 14 (93) | |

TABLE 22-continued

Virulence gene distribution by ST131 subclone among 71 ST131 *Escherichia coli* isolates.

| Functional category | Specific gene[a] | Gene prevalence within ST131 by H30 subclone status, no. (column %) | | P value[b], H30 vs. non-H30 | Gene prevalence within H30 subclone by H30-Rx status, no. (column %) | | non-P value[b], H30-Rx vs. H30 non-Rx |
|---|---|---|---|---|---|---|---|
| | | H30 (N = 62) | Non-H30 (N = 9) | | H30-Rx (N = 47) | H30, Rx (N = 15) | |
| Protectins | kpsMII | 53 (85) | 8 (89) | | 44 (94) | 9 (60) | .004 |
| | K1 | 2 (3) | 3 (33) | .01 | 1 (2) | 1 (7) | |
| | K5 | 17 (27) | 1 (11) | | 9 (19) | 8 (53) | .02 |
| Misc. | ibeA | 0 | 6 (67) | <.001 | 0 | 0 | |

[a]Virulence genes listed are those that yielded P < .05 in at least one comparison.
[b]P values (by Fisher's exact test) are shown only when P < .05; all others, non-significant.

Example 34. Additional SNPs Present in the H30-Rx Subclone

Additional SNPs were identified that are present in the H30-Rx subclone (see Table 23). In some embodiments, these SNPs may be used alternatively or in addition to those shown in Table 1 for the detection of H30-Rx in a sample.

TABLE 23

SNPs present in the H30-Rx subclone

| SNP Position* | SNP Number | SNP type | CI | Change | Node Path |
|---|---|---|---|---|---|
| 525676 | 422 | nSNP | 1.0 | G→A | 145 to 146 |
| 1388265 | 1261 | nSNP | 1.0 | A→T | 145 to 146 |
| 2521116 | 2689 | nSNP | 1.0 | G→A | 145 to 146 |
| 4616159 | 7250 | sSNP | 1.0 | C→T | 145 to 146 |
| 4616228 | 7252 | sSNP | 1.0 | A→G | 145 to 146 |
| 4617419 | 7263 | sSNP | 1.0 | C→A | 145 to 146 |
| 4624528 | 7328 | sSNP | 1.0 | G→A | 145 to 146 |
| 4624566 | 7330 | sSNP | 1.0 | G→A | 145 to 146 |
| 4624997 | 7341 | sSNP | 1.0 | A→T | 145 to 146 |
| 4631170 | 7371 | sSNP | 1.0 | C→T | 145 to 146 |
| 4639802 | 7412 | sSNP | 1.0 | C→T | 145 to 146 |
| 4639859 | 7413 | sSNP | 1.0 | T→C | 145 to 146 |
| 4639881 | 7415 | sSNP | 1.0 | C→A | 145 to 146 |
| 4640549 | 7416 | sSNP | 1.0 | C→T | 145 to 146 |
| 4713742 | 7483 | sSNP | 1.0 | C→T | 146 to 147 |
| 4740639 | 7531 | sSNP | 1.0 | A→G | 146 to 147 |
| 4741970 | 7541 | sSNP | 1.0 | C→G | 146 to 147 |
| 4742207 | 7543 | sSNP | 1.0 | A→G | 146 to 147 |
| 4751068 | 7573 | sSNP | 1.0 | C→T | 146 to 147 |
| 4751944 | 7580 | sSNP | 1.0 | G→A | 146 to 147 |
| 4756917 | 7656 | nSNP | 1.0 | T→C | 146 to 147 |
| 4757321 | 7669 | sSNP | 1.0 | T→C | 146 to 147 |
| 4757369 | 7670 | sSNP | 1.0 | A→G | 146 to 147 |
| 4757415 | 7671 | nSNP | 1.0 | G→A | 146 to 147 |
| 4763949 | 7739 | sSNP | 1.0 | C→A | 146 to 147 |

*These positions are based on the *Escherichia coli* NA114 (CP002797).

Example 34. Further Characterization of SNP-200, SNP-264, and SNP-3729

SNP-200, SNP-264, and SNP-3729 were further characterized as shown in Tables 24A, 24B, and 24C.

TABLE 24A

Additional characteristics of SNP-200, SNP-264, and SNP-3729

| SNP number | SNP Type | Gene Pos | Gene Start | Gene End | Ref Codon | Derived Codon | Ref AA | Derived AA | Locus Tag |
|---|---|---|---|---|---|---|---|---|---|
| SNP200 | nSNP | 877 | 392073 | 393293 | GTG | GCG | V | A | ECNA114_0352 |
| SNP264 | sSNP | 722 | 530272 | 531726 | GCA | GCG | A | A | ECNA114_0488 |
| SNP3729 | iSNP | | | | | | | | |

TABLE 24B

Additional characteristics of SNP-200, SNP-264, and SNP-3729

| SNP number | SNP distance | position | SNP Strand | Gene Strand | steps | CI | Change from | Change to | Range |
|---|---|---|---|---|---|---|---|---|---|
| SNP200 | | 392950 | + | + | 1 | 1 | C | T | 1 |
| SNP264 | 138044 | 530994 | + | + | 1 | 1 | G | A | 1 |
| SNP3729 | 1463724 | 1994718 | | | 1 | 1 | G | A | |

TABLE 24C

Additional characteristics of SNP-200, SNP-264, and SNP-3729

| SNP number | Min Steps | Tree Steps | Max Steps | CI | RI | RC | Hi | G-fit | Ref seq |
|---|---|---|---|---|---|---|---|---|---|
| SNP200 | 1 | 1 | 27 | 1 | 1 | 1 | 0 | 1 | + |
| SNP264 | 1 | 1 | 27 | 1 | 1 | 1 | 0 | 1 | + |
| SNP3729 | 1 | 1 | 27 | 1 | 1 | 1 | 0 | 1 | iSNP |

Abbreviations

AA: amino acid; Ref: reference; Pos: position; seq: sequence

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of detecting the presence of *Escherichia coli* sequence type 131 (ST131) in a sample, comprising detecting the presence of an allelic combination of gyrA1AB/parC1aAB, wherein detection of the allelic combination confirms the presence of ST131 in the sample and the absence of the allelic combination indicates the absence of ST131 in the sample.

2. The method of claim 1, wherein the ST131 is subclone H30-R or subclone H30-Rx.

3. The method of claim 2, further comprising sequencing an allele 30 of a fimH gene in the sample to confirm the presence of subclone H30-R or subclone H30-Rx.

4. The method of claim 3, wherein sequencing the fimH gene comprises PCR amplification of the fimH gene with at least one primer selected from the group consisting of a primer comprising the nucleic acid sequence of SEQ ID NO: 1, a primer comprising the nucleic acid sequence of SEQ ID NO: 2, a primer comprising the nucleic acid sequence of SEQ ID NO: 5, a primer comprising the nucleic acid sequence of SEQ ID NO: 7, a primer comprising the nucleic acid sequence of SEQ ID NO: 8, a primer comprising the nucleic acid sequence of SEQ ID NO: 9, and a primer comprising the nucleic acid sequence of SEQ ID NO: 10.

5. The method of claim 3, wherein detecting the presence of the allelic combination of gyrA1AB/parC1aAB comprises sequencing gyrA and parC genes in the sample.

6. A method of detecting the presence of *E. coli* sequence type 131 (ST131) subclone H30-Rx in a sample comprising detecting the presence of an allelic combination of fimH30, mdh36, and gyrB47, wherein detection of the allelic combination confirms the presence of H30-Rx in the sample and the absence of the allelic combination indicates the absence of H30-Rx in the sample.

7. The method of a claim 6, wherein detection of the allelic combination comprises PCR amplification of fimH30 with primers comprising the nucleotide sequences of SEQ ID NO: 1 and SEQ ID NO: 2, PCR amplification of mdh36 with primers comprising the nucleotide sequences of SEQ ID NO: 15 and SEQ ID NO: 16, and PCR amplification of gyrB47 with primers comprising the nucleotide sequences of SEQ ID NO: 17 and SEQ ID NO: 18.

8. A method of detecting the presence of a CTX-M-15-associated E. coli subclone H30-Rx within a population of H30 subclones in a sample comprising detecting single nucleotide polymorphism 200 (SNP-200) and single nucleotide polymorphism 264 (SNP-264) in a fimH30 gene, wherein the presence of both SNP-200 and SNP-264 confirms the presence of H30-Rx.

9. The method of claim 8, wherein SNP-200 is a C-to-T transition at position 299 of a 460-bp PCR product generated using a forward primer comprising the nucleic acid sequence of SEQ ID NO: 57 and reverse primer comprising the nucleic acid sequence of SEQ ID NO: 58 and wherein SNP-264 is a G-to-A transition at position 287 of a 462-bp PCR product generated using a forward primer comprising the nucleic acid sequence of SEQ ID NO: 59 and reverse primer comprising the nucleic acid sequence of SEQ ID NO: 60.

10. The method according to claim 6, further comprising detecting single nucleotide polymorphism 3729 (SNP-3729), wherein the presence of SNP-3729 confirms the presence of H30-Rx.

11. The method according to claim 6, wherein H30-Rx is fluoroquinolone-resistant (FQ-R), blaCTX-M-15-positive, and associated with sepsis in human subjects.

12. The method of claim 1, wherein the sample is a biological sample from a human subject between newborn and 10-years-old or 50-years-old and older.

13. A method of treating a subject with a bacterial infection comprising:
a) detecting the presence of an E. coli ST131 subclone H30 or an E. coli subclone H30-Rx according to the method of claim 1 in a sample from the subject; and b) treating the subject with an antimicrobial agent that is not fluoroquinolone (FQ), gentamicin, or trimethoprim-sulfamethoxazole (TMP/SMX).

14. The method of claim 13, further comprising:
c) treating the subject with an antimicrobial agent selected from the group consisting of nitrofurantoin, fosfomycin, carbapenem, colistin, tigecycline, and amikacin.

15. A method of identifying the presence of E. coli H30-R and/or H30-Rx, comprising:
providing DNA from an E. coli sample; and
detecting in the DNA from the E. coli sample whether the DNA has one or more single nucleotide polymorphisms (SNP) selected from the group consisting of SNP3446, SNP3500, SNP4907, and SNP10603, wherein detection of one or more of the SNPs indicating the presence of E. coli H30-R and/or H30-Rx in the E. coli sample; or selected from the group consisting of one or more single nucleotide polymorphisms (SNP) selected from the group consisting of SNP200, SNP264, and SNP3729, wherein detection of one or more of the SNPs indicating the presence of E. coli H30-Rx in the E. coli sample.

16. The method of claim 15, further comprising:
detecting in the DNA from the E. coli sample whether the DNA has an SNP of G723A in an allantoin protein-encoding ybbW gene, wherein detection of the SNP of G723A in ybbW indicating the presence of E. coli H30-Rx in the E. coli sample and the SNP is detected with PCR amplification of the ybbW gene using primers comprising the sequences of SEQ ID NO: 63 and/or SEQ ID NO: 64.

17. The method of claim 15, wherein a primer or probe comprising a labeled nucleic acid sequence having a nucleic acid sequence consisting of any one of SEQ ID NO: 1, SEQ ID NO: 2, SEQ ID NO: 5, SEQ ID NO: 7, SEQ ID NO: 8, SEQ ID NO: 9, SEQ ID NO: 10, SEQ ID NO: 15, SEQ ID NO: 16, SEQ ID NO: 17, SEQ ID NO: 18, NO: 57, SEQ ID NO: 58, SEQ ID NO: 59, SEQ ID NO: 60, SEQ ID NO: 63, SEQ ID NO: 64, a labeled fragment or derivative thereof, a labeled complementary sequence thereof, wherein the sequences have at least 90% nucleic acid sequence identity thereto is used to confirm the presence of E. coli H30-R and/or H30-Rx in the sample.

* * * * *

UNITED STATES PATENT AND TRADEMARK OFFICE
CERTIFICATE OF CORRECTION

PATENT NO. : 9,834,823 B2  
APPLICATION NO. : 14/412667  
DATED : December 5, 2017  
INVENTOR(S) : Lance B. Price, Evgeni V. Sokurenko and James R. Johnson Page 1 of 1

It is certified that error appears in the above-identified patent and that said Letters Patent is hereby corrected as shown below:

In the Specification

Column 1, Line 23, before "TECHNICAL FIELD" insert:
--STATEMENT REGARDING FEDERALLY SPONSORED RESEARCH
This invention was made with government support under grant number AI092828 awarded by the National Institutes of Health. The government has certain rights in the invention.--

Signed and Sealed this
Twenty-fifth Day of June, 2019

Andrei Iancu
*Director of the United States Patent and Trademark Office*

```
SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccgccaatgg taccgctatt                                                   20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cagctttaat cgccacccca                                                   20

<210> SEQ ID NO 3
<211> LENGTH: 489
<212> TYPE: DNA
<213> ORGANISM: Escherichia coli

<400> SEQUENCE: 3
ttcgcctgta aaaccgccaa tggtaccgct attcctattg gcggtggcag cgctaatgtt       60
tatgtaaacc ttgcgcctgc cgtgaatgtg gggcaaaacc tggtcgtaga tctttcgacg      120
caaatctttt gccataacga ttatccggaa accattacag actatgtcac actgcaacga      180
ggctcggctt atggcggcgt gttatctaat ttttccggga ccgtaaaata tagtggcagt      240
agctatccat ttccgactac cagcgaaacg ccgcgggttg tttataattc gagaacggat      300
aagccgtggc cggtggcgct ttatttgacg cctgtgagca gtgcgggtgg ggtggcgatt      360
aaagctggct cattaattgc cgtgcttatt ttgcgacaga ccaacaacta taacagcgat      420
gatttccagt ttgtgtggaa tatttacgcc aataatgatg tggtggtgcc tactggcggc      480
tgcgatgtt                                                             489
```

```
<210> SEQ ID NO 4
<211> LENGTH: 903
<212> TYPE: DNA
<213> ORGANISM: Escherichia coli

<400> SEQUENCE: 4
atgaaacgag ttattaccct gtttgctgta ctgctgatgg gctggtcggt aaatgcctgg      60
tcattcgcct gtaaaaccgc caatggtacc gctattccta ttggcggtgg cagcgctaat    120
gtttatgtaa accttgcgcc tgccgtgaat gtggggcaaa acctggtcgt agatctttcg    180
acgcaaatct tttgccataa cgattatccg gaaaccatta cagactatgt cacactgcaa    240
cgaggctcgg cttatggcgg cgtgttatct aattttccg ggaccgtaaa atatagtggc     300
agtagctatc catttccgac taccagcgaa acgccgcggg ttgtttataa ttcgagaacg    360
gataagccgt ggccggtggc gctttatttg acgcctgtga gcagtgcggg tggggtggcg    420
attaaagctg gctcattaat tgccgtgctt attttgcgac agaccaacaa ctataacagc    480
gatgatttcc agtttgtgtg gaatatttac gccaataatg atgtggtggt gcctactggc    540
ggctgcgatg tttctgctca tgatgtcacc gttactctgc cggactaccc tggttcagtg    600
ccaattcctc ttaccgttta ttgtgcgaaa agccaaaacc tggggtatta cctctccggc    660
acaaccgcag atgcgggcaa ctcgattttc accaataccg cgtcgttttc accagcgcag    720
ggcgtcggcg tacagttgac gcgcaacggt acgattattc cagcgaataa cacggtatcg    780
ttaggagcag tagggacttc ggcggtaagt ctgggattaa cggcaaatta cgcacgtacc    840
ggagggcagg tgactgcagg gaatgtgcaa tcgattattg gcgtgacttt tgtttatcaa    900
taa                                                                   903

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tggggtggcg attaaagctg                                                  20

<210> SEQ ID NO 6
<211> LENGTH: 12
<212> TYPE: DNA
<213> ORGANISM: Artificial Sequence
<220> FEATURE:
<223> OTHER INFORMATION: Primer

<400> SEQUENCE: 6
tggggtggcg at                                                          12

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gccaatggta ccgctatt                                                    18
```

```
<210> SEQ ID NO 8
<211> LENGTH: 16
<212> TYPE: DNA
<213> ORGANISM: Artificial Sequence
<220> FEATURE:
<223> OTHER INFORMATION: Primer

<400> SEQUENCE: 8
caatggtacc gctatt                                                    16

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
gagccagctt taatcgccac ccca                                           24

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gccagcttta atcgccaccc ca                                             22

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
gcgtctgttg actggcaggt ggtgg                                          25

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
gttgcccgct tcgaaaccaa tgcct                                          25

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ataccgacga cgccgatctg                                                20

<210> SEQ ID NO 14
<211> LENGTH: 20
<212> TYPE: DNA
<213> ORGANISM: Artificial Sequence
<220> FEATURE:
<223> OTHER INFORMATION: Primer
```

```
<400> SEQUENCE: 14
ggatcattta tgctggtacg                                          20

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
taacgttaac gccggt                                              16

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
ggtaacacca gagtgacca                                           19

<210> SEQ ID NO 17
<211> LENGTH: 15
<212> TYPE: DNA
<213> ORGANISM: Artificial Sequence
<220> FEATURE:
<223> OTHER INFORMATION: Primer

<400> SEQUENCE: 17
cgcgataagc gcgac                                               15

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
accgtctttt tcggtggaa                                           19

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
cgtgacctgt ccgttcataa gtagag                                   26

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
gcgatggcga aaacactgta tgac                                     24
```

```
<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tggccttgtc agacctgcta ac                                              22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gagagactca tatcgcgctc ca                                              22

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ctttcccatt gcatacgctc atag                                            24

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
caggtgcgtg tataggtaat ggt                                             23

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
aggttgatcg ccagaatcat ca                                              22

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
aacccaccac cgttaaaaat cg                                              22

<210> SEQ ID NO 27
<211> LENGTH: 21
<212> TYPE: DNA
<213> ORGANISM: Artificial Sequence
<220> FEATURE:
<223> OTHER INFORMATION: Primer
```

```
<400> SEQUENCE: 27
attctttgct ggaatgcgtg c                                            21

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
aacccaccac cgttaaaaat cg                                           22

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
ggcaggtaag tttgacgatt tct                                          23

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
cagcgatgaa tttgtttctt tgtg                                         24

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
cagacgatca gcattggctt g                                            21

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
gcggcatcca gtgcttttaa c                                            21

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
tcctgaccca tagtgaaatc g                                            21
```

-continued

```
<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gctctatccc agatgccgta                                              20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggcagtggtg tcttttggtg                                              20

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
ctcctcatta tgaccagaaa ccct                                         24

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gggatgagcg ggcctttgat                                              20

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
cgggccccca agtaactcg                                               19

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
caacatgctt ccagcactcc t                                            21

<210> SEQ ID NO 40
<211> LENGTH: 23
<212> TYPE: DNA
<213> ORGANISM: Artificial Sequence
<220> FEATURE:
<223> OTHER INFORMATION: Primer
```

<400> SEQUENCE: 40
cccagaatac gataacggag acg					23

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
gtgaaaccgt actgcgtgat gc					22

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
gaccagcatg tgggagacaa tg					22

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
gtcggtgatg ccaggtttaa aga					23

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
cgcacctcat ggacgatatg tt					22

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
gtcggtgatg ccaggtttaa aga					23

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
ctttcaccga tcattcccga ct					22

```
<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
gtcggtgatg ccaggtttaa aga                                              23

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
tttcacatcg ctcattttct gga                                              23

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
gtcggtgatg ccaggtttaa aga                                              23

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
tggtgaagac gcaggttaat gc                                               22

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
ccgcaaggtg agtgacatca g                                                21

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
tgggagggta tgcagcttgt t                                                21

<210> SEQ ID NO 53
<211> LENGTH: 20
<212> TYPE: DNA
<213> ORGANISM: Artificial Sequence
<220> FEATURE:
<223> OTHER INFORMATION: Primer
```

```
<400> SEQUENCE: 53
ggcagtggtg tcttttggtg                                               20

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
aaggccccgt tgacgtttt                                                19

<210> SEQ ID NO 55
<211> LENGTH: 25
<212> TYPE: DNA
<213> ORGANISM: Artificial Sequence
<220> FEATURE:
<223> OTHER INFORMATION: Primer

<400> SEQUENCE: 55
atcctatctt tcccaaatcg aaaca                                         25

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
caggtgcgtg tataggtaat ggt                                           23

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
gacaccatgc gttttgcttc                                               20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
tcgtaccggc aacaattgac                                               20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gtggcgattt cacgctgtta                                               20
```

```
<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
tatccagcac gttccaggtg                                                    20

<210> SEQ ID NO 61
<211> LENGTH: 19
<212> TYPE: DNA
<213> ORGANISM: Artificial Sequence
<220> FEATURE:
<223> OTHER INFORMATION: Primer

<400> SEQUENCE: 61
ataaaaccgg cagcggtgg                                                     19

<210> SEQ ID NO 62
<211> LENGTH: 18
<212> TYPE: DNA
<213> ORGANISM: Artificial Sequence
<220> FEATURE:
<223> OTHER INFORMATION: Primer

<400> SEQUENCE: 62
gaattttgac gatcgggg                                                      18

<210> SEQ ID NO 63
<211> LENGTH: 16
<212> TYPE: DNA
<213> ORGANISM: Artificial Sequence
<220> FEATURE:
<223> OTHER INFORMATION: Primer

<400> SEQUENCE: 63
ggttgcggtc tgggca                                                        16

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
caatatccag cacgttccag gtg                                                23
```